US008889639B2

(12) United States Patent
Spiegelman et al.

(10) Patent No.: US 8,889,639 B2
(45) Date of Patent: Nov. 18, 2014

(54) COMPOSITIONS AND METHODS FOR MODULATING PGC-1β TO TREAT LIPID-RELATED DISEASES AND DISORDERS

(75) Inventors: Bruce M. Spiegelman, Waban, MA (US); Jiandie Lin, Ann Arbor, MI (US); Christopher B. Newgard, Chapel Hill, NC (US)

(73) Assignees: Dana-Farber Cancer Institute, Inc., Boston, MA (US); Duke University, Durham, NC (US)

( * ) Notice: Subject to any disclaimer, the term of this patent is extended or adjusted under 35 U.S.C. 154(b) by 1636 days.

(21) Appl. No.: 11/577,614

(22) PCT Filed: Oct. 21, 2005

(86) PCT No.: PCT/US2005/037952
§ 371 (c)(1), (2), (4) Date: Apr. 11, 2008

(87) PCT Pub. No.: WO2006/047312
PCT Pub. Date: May 4, 2006

(65) Prior Publication Data
US 2008/0206232 A1 Aug. 28, 2008

Related U.S. Application Data

(60) Provisional application No. 60/621,488, filed on Oct. 22, 2004.

(51) Int. Cl.
C12N 15/11 (2006.01)
C07H 21/02 (2006.01)
C07H 21/04 (2006.01)
A61K 48/00 (2006.01)

(52) U.S. Cl.
USPC ..................... 514/44 A; 536/24.5

(58) Field of Classification Search
USPC .................................................. 514/44
See application file for complete search history.

(56) References Cited

U.S. PATENT DOCUMENTS 6,165,786 A * 12/2000 Bennett et al. ............... 435/366

FOREIGN PATENT DOCUMENTS

| WO | WO-97/07668 | 3/1997 |
| WO | WO-97/07669 | 3/1997 |
| WO | WO-03/042362 | 5/2003 |

OTHER PUBLICATIONS

Nagai et al. Cell Metab, 2009 vol. 9:252-264.*
Hammond et al. (Nature Reviews Genetics 2001, vol. 2:110-119).*
Auboeuf et al., "Tissue distribution and quantification of the expression of mRNAs of peroxisome proliferator-activated receptors and liver X receptor-alpha in humans: no alteration in adipose tissue of obese and NIDDM patients," Diabetes 46:1319-1327 (1997).
Betteridge, D.J., "Diabetic dyslipidaemia," Eur. J. Clin. Invest 29 Suppl. 2:12-16 (1999).

(Continued)

Primary Examiner — Terra Cotta Gibbs
(74) Attorney, Agent, or Firm — Foley Hoag LLP

(57) ABSTRACT

The present invention provides methods for treating lipid-related diseases and disorders, e.g., hyperlipidemia, hypertriglyceridemia, hypercholesterolemia, cardiovascular disease, obesity, and type II diabetes, and for modulating lipid biosynthesis, lipid transport, plasma triglyceride levels and/or plasma cholesterol levels, by modulating the expression or activity of PGC-1β. Methods for identifying compounds which are capable of treating or preventing a lipid-related disease or disorder are also described.

38 Claims, 10 Drawing Sheets

(56) References Cited

OTHER PUBLICATIONS

Breslow, J.L., "Genetics of lipoprotein abnormalities associated with coronary heart disease susceptibility," Annu. Rev. Genet. 34:233-254 (2000).

Brown and Goldstein, "The SREBP Pathway: Regulation of Cholesterol Metabolism by Proteolysis of a Membrane-Bound Transcription Factor," Cell 89:331-340 (1997).

Chatterjee et al., "Targeted overexpression of androgen receptor with a liver-specific promoter in transgenic mice," Proc. Natl. Acad. Sci. USA 93(2):728-733 (1996).

Chawla et al., "A PPARγ-LXR-ABCA1 Pathway in Macrophages Is Involved in Cholesterol Efflux and Atherogenesis," Mol. Cell 7:161-171 (2001).

Flier, J.S., "Obesity Wars: Molecular Progress Confronts an Expanding Epidemic," Cell 116:337-350 (2004).

Foretz et al., "Sterol regulatory element binding protein-1c is a major mediator of insulin action on the hepatic expression of glucokinase and lipogenesis-related genes," Proc. Natl. Acad. Sci USA 96:12737-12742 (1999).

GenBank Accession No. NM_133263 (GI: 31543391).

Girard et al., "Mechanisms by which carbohydrates regulate expression of genes for glycolytic and lipogenic enzymes," Annu. Rev. Nutr. 17:325-352 (1997).

Goldberg, I., "Diabetic Dyslipidemia: Causes and Consequences," J Clin. Endocrinol. Metab. 86, 965-971 (2001).

Grefhorst et al., "Stimulation of Lipogenesis by Pharmacological Activation of the Liver X Receptor Leads to Production of Large, Triglyceride-rich Very Low Density Lipoprotein Particles," J. Biol. Chem. 277:34182-34190 (2002).

Hannah et al., "Unsaturated Fatty Acids Down-regulate SREBP Isoforms 1a and 1c by Two Mechanisms in HEK-293 Cells," J Biol. Chem. 276:4365-4327 (2001).

Hellerstein, M.K., "Regulation of Hepatic De Novo Lipogenesis in Humans," Annu. Rev. Nutr. 16:523-557 (1996).

Horton et al., "Activation of Cholesterol Synthesis in Preference to Fatty Acid Synthesis in Liver and Adipose Tissue of Transgenic Mice Overproducing Sterol Regulatory Element-binding Protein-2," J. Clin. Invest. 101, 2331-2339 (1998).

Horton et al., "Combined analysis of oligonucleotide microarray date from transgenic and knockout mice identifies direct SREBP target genes," Proc. Natl. Acad. Sci. USA 100:12027-12032 (2003).

Horton et al., "SREBPs: activators of the complete program of cholesterol and fatty acid synthesis in the liver," J. Clin. Invest. 109, 1125-1131 (2002).

Hua et al., "SREBP-2, a second basic-helix-loop-helix-leucine zipper protein that stimulates transcription by binding to a sterol regulatory element," Proc. Natl. Acad. Sci. USA 90:11603-11607 (1993).

Joseph et al., "Direct and Indirect Mechanisms for Regulation of Fatty Acid Synthase Gene Expression by Liver X Receptors," J Biol. Chem. 277, 11019-11025 (2002).

Kamei et al., "PPARγ coactivator 1β/ERR ligand 1 is an ERR protein ligand, whose expression induces a high-energy expenditure and antagonizes obesity," Proc. Natl. Acad. Sci. USA 100:12378-12383 (2003).

Kim and Spiegelman, "ADD1/SREBP1 promotes adipocyte differentiation and gene expression linked to fatty acid metabolism," Genes Dev. 10, 1096-1107 (1996).

Kim et al., "Nutritional and Insulin Regulation of Fatty Acid Synthetase and Leptin Gene Expression through ADD1/SREBP1," J. Clin. Invest. 101:1-9 (1998).

Kressler et al., "The PGC-1-related Protein PERC Is a Selective Coactivator of Estrogen Receptor α," J. Biol. Chem. 277, 13918-13925 (2002).

Li and Wong, "Model-based analysis of oligonucleotide arrays: Expression index computation and outlier detection," Proc. Natl. Acad. Sci. USA 98:31-36 (2001).

Lin et al., "Peroxisome Proliferator-activated Receptor γ Coactivator 1β (PGC-1β), A Novel PGC-1-related Transcription Coactivator Associated with Host Cell Factor," J. Biol. Chem. 277:1645-1648 (2002).

Lin et al., "PGC-1β in the Regulation of Hepatic Glucose and Energy Metabolism," J. Biol. Chem. 278:30843-30848 (2003).

Lin et al., "Transcriptional co-activator PGC-1α drives the formation of slow-twitch muscle fibres," Nature 418:797-801 (2002).

Magana and Osborne, "Two Tandem Binding Sites for Sterol Regulatory Element Binding Proteins Are Required for Sterol Regulation of Fatty-acid Synthase Promoter," J. Biol. Chem. 271:32689-32694 (1996).

Murthy et al., "LXR/RXCR activation enhances basolateral efflux of cholesterol in CaCo-2 cells," J. Lipid Res. 43:1054-1064 (2002).

"NHLBI High Blood Cholesterol: What you need to know" www.nhlbi.nih.gov/health/public/heart/chol/wyntk.htm (2004).

Pai et al., "Differential Stimulation of Cholesterol and Unsaturated Fatty Acid Biosynthesis in Cells Expressing Individual Nuclear Sterol Regulatory Element-binding Proteins," J. Biol. Chem. 273:26138-26148 (1998).

Puigserver and Spiegelman, "Peroxisome Proliferabor-Activated Receptor-γ Coactivator 1α (PGC-1α): Transcriptional Coactivator and Metabolic Regulator," Endocr. Rev. 24:78-90 (2003).

Reaven et al., "Obesity, Insulin Resistance, and Cardiovascular Disease," Recent Prog. Horm. Res. 59:207-223 (2004).

Repa et al., "Regulation of mouse sterol regulatory element-binding protein-1c gene (SREBP-1c) by oxysterol receptors, LXRα and LXRβ," Genes Dev 14, 2819-2830 (2000).

Sacks and Katan, "Randomized Clinical Trials on the Effects of Dietary Fat and Carbohydrate on Plasma Lipoproteins and Cardiovascular Disease," Am. J Med. 113(9B):13S-24S (2002).

Sakai et al., "Sterol-Regulated Release of SREBP-2 from Cell Membranes Requires Two Sequential Cleavages, One Within a Transmembrane Segment," Cell 85:1037-1046 (1996).

Schultz et al., "Role of LXRs in control of lipogenesis," Genes Dev. 14:2831-2838 (2000).

Shimano et al., "Isoform 1c of Sterol Regulatory Element Binding Protein Is Less Active Than Isoform 1a in Livers of Transgenic Mice and in Cultured Cells," J Clin: Invest. 99:846-854 (1997).

Shimano et al., "Overproduction of Cholesterol and Fatty Acids Causes Massive Liver Enlargement in Transgenic Mice Expressing Truncated SREBP-1a," J Clin. Invest. 98:1575-1584 (1996).

Shimomura et al., "Differential Expression of Exons 1a and 1c in mRNAs for Sterol Regulatory Element Binding Protein-1 in Human and Mouse Organs and Cultured Cells," J. Clin. Invest. 99, 838-845 (1997).

Shimomura et al., "Insulin selectively increases SREBP-1c mRNA in the livers of rats with streptozotocin-induced diabetes," Proc. Natl. Acad. Sci. USA 96:13656-13661 (1999).

Spady et al., "Regulationof Plasma LDL-Cholesterol Levels by Dietary Cholesterol and Fatty Acids," Annu. Rev. Nutr. 13:355-381 (1993).

St-Pierre et al., "Bioenergetic Analysis of Peroxisome Proliferator-activated Receptor γ Coactovators 1α and 1β (PGC-1α and PGC-1β) in Muscle Cells," J Biol. Chem. 278:26597-26603 (2003).

Tontonoz et al., "ADD1: a Novel Helix-Loop-Helix Transcription Factor Associated with Adipocyte Determination and Differentiation," Mol. Cell Biol. 13(8):4753-4759 (1993).

Wilmut et al., "Viable offspring derived from fetal and adult mammalian cells," Nature 385:810-813 (1997).

Yokoyama et al., "SREBP-1, a Basic-Helix-Loop-Helix-Leucine Zipper Protein That Controls Transcription of the Low Density Lipoprotein Receptor Gene," Cell 75:187-197 (1993).

Zimmet et al., "Global and societal implications of the diabetes epidemic," Nature 414:782-787 (2001).

Knutti et al., "A tissue-specific coactivator of steroid receptors, identified in a functional genetic screen," Mol. Cell. Biol. 20:2411-2422 (2000).

Meirhaeghe et al., "Characterization of the human, mouse and rat PGC1β (peroxisome-proliferator-activated receptor-γ co-activator 1β) gene in vitro and in vivo," Biochem. J. 373:155-165 (2003).

International Search Report dated Aug. 14, 2008 from PCT/US05/037952.

* cited by examiner

SEQUENCE LISTING

```
<160> NUMBER OF SEQ ID NOS: 61

<210> SEQ ID NO 1
<211> LENGTH: 3277
<212> TYPE: DNA
<213> ORGANISM: Homo sapiens

<400> SEQUENCE: 1
ctcggcgttg actccgccgc acgctgcagc cgcggctgga agatggcggg gaacgactgc      60
ggcgcgctgc tggacgaaga gctctcctcc ttcttcctca actatctcgc tgacacgcag     120
ggtggagggt ccggggagga gcaactctat gctgactttc agaacttga cctctcccag     180 ctggatgcca gcgactttga ctcggccacc tgctttgggg agctgcagtg gtgcccagag     240
aactcagaga ctgaacccaa ccagtacagc cccgatgact ccgagctctt ccagattgac     300
agtgagaatg aggccctcct ggcagagctc accaagaccc tggatgacat ccctgaagat     360
gacgtgggtc tggctgcctt cccagccctg gatggtggag acgctctatc atgcacctca     420
gcttcgcctg cccctcatc tgcaccccc agccctgccc cggagaagcc ctcggcccca     480
gcccctgagg tggacgagct ctcactgctg cagaagctcc tcctggccac atcctaccca     540
acatcaagct ctgacaccca gaaggaaggg accgcctggc gccaggcagg cctcagatct     600
aaaagtcaac ggccttgtgt taaggcggac agcacccaag acaagaaggc tcccatgatg     660
cagtctcaga gccgaagttg tacagaacta cataagcacc tcacctcggc acagtgctgc     720
ctgcaggatc ggggtctgca gccaccatgc ctccagagtc cccggctccc tgccaaggag     780
```

```
gacaaggagc cgggtgagga ctgcccgagc ccccagccag ctccagcctc tccccaggac    840
tccctagctc tgggcagggc agaccccggt gccccggttt cccaggaaga catgcaggcg    900
atggtgcaac tcatacgcta catgcacacc tactgcctcc cccagaggaa gctgccccca    960
cagacccctg agccactccc caaggcctgc agcaacccct cccagcaggt cagatcccgg   1020
ccctggtccc ggcaccactc caaagcctcc tgggctgagt tctccattct gagggaactt   1080
ctggctcaag acgtgctctg tgatgtcagc aaacccctacc gtctggccac gcctgtttat   1140
gcctccctca cacctcggtc aaggcccagg cccccaaag acagtcaggc ctcccctggt    1200
cgcccgtcct cggtggagga ggtaaggatc gcagcttcac ccaagagcac cgggcccaga   1260
ccaagcctgc gcccactgcg gctggaggtg aaaagggagg tccgccggcc tgccagactg   1320
cagcagcagg aggaggaaga cgaggaagaa gaggaggagg aagaggaaga agaaaaagag   1380
gaggaggagg agtgggcag gaaaaggcca ggccgaggcc tgccatggac gaagctgggg    1440
aggaagctgg agagctctgt gtgccccgtg cggcgttctc ggagactgaa ccctgagctg   1500
ggccctggc tgacatttgc agatgagccg ctggtcccct cggagcccca aggtgctctg    1560
ccctcactgt gcctggctcc caaggcctac gacgtagagc gggagctggg cagccccacg   1620
gacgaggaca gtgccaaga ccagcagctc ctacggggac cccagatccc tgccctggag    1680
agccctgtg agagtgggtg tggggacatg gatgaggacc ccagctgccc gcagctccct   1740
cccagagact ctcccaggtg cctcatgctg gcccttgtcac aaagcgaccc aacttttggc   1800
aagaagagct ttgagcagac cttgacagtg gagctctgtg gcacagcagg actcacccca   1860
cccaccacac caccgtacaa gcccacagag gaggatccct tcaaaccaga catcaagcat   1920
agtctaggca aagaaatagc tctcagcctc ccctcccctg agggcctctc actcaaggcc   1980
accccagggg ctgcccacaa gctgccaaag aagcacccag agcgaagtga gctcctgtcc   2040
cacctgcgac atgccacagc ccagccagcc tcccaggctg gccagaagcg tcccttctcc   2100
tgttcctttg agaccatga ctactgccag gtgctccgac cagaaggcgt cctgcaaagg   2160
aaggtgctga ggtcctggga gccgtctggg gttcaccttg aggactggcc ccagcagggt   2220
gcccttggg ctgaggcaca ggcccctggc agggaggaag acagaagctg tgatgctggt    2280
gcccaccca aggacagcac gctgctgaga gaccatgaga tccgtgctag cctcaccaaa   2340
cactttgggc tgctggagac cgccctggag gaggaagacc tggcctcctg caagagccct   2400
gagtatgaca ctgtctttga agacagcagc agcagcagcg gcgagagcag cttcctccca   2460
gaggaggaag aggaagaagg ggaggaggag gaggaggacg atgaagaaga ggactcaggg   2520
gtcagcccca cttgctctga ccactgcccc taccagagcc accaagcaa ggccaaccgg    2580
cagctctgtt cccgcagccg ctcaagctct ggctcttcac cctgccactc ctggtcacca   2640
gccactcgaa ggaacttcag atgtgagagc agagggccgt gttcagacag aacgccaagc   2700
atccggcacg ccaggaagcg gcgggaaaag gccattgggg aaggccgcgt ggtgtacatt   2760
caaaatctct ccagcgacat gagctcccga gagctgaaga ggcgctttga agtgtttggt   2820
gagattgagg agtgcgaggt gctgacaaga aataggagag gcgagaagta cggcttcatc   2880
acctaccggt gttctgagca cgcggccctc tctttgacaa agggcgctgc cctgaggaag   2940
cgcaacgagc cctccttcca gctgagctac ggagggctcc ggcacttctg ctggcccaga   3000
tacactgact acgattccaa ttcagaagag gcccttcctg cgtcagggaa aagcaagtat   3060
gaagccatgg attttgacag cttactgaaa gaggcccagc agagcctgca ttgataacag   3120
ccttaaccct cgaggaatac ctcaataacct cagacaaggc ccttccaata tgtttacgtt   3180
```

-continued

```
ttcaaagaaa tcaagtatat gaggagagcg agcgagcgtg agagaacacc cgtgagagag    3240
acttgaaact gctgtccttt aaaaaaaaaa aaaaaaa                             3277
```

<210> SEQ ID NO 2
<211> LENGTH: 1023
<212> TYPE: PRT
<213> ORGANISM: Homo sapiens

<400> SEQUENCE: 2

```
Met Ala Gly Asn Asp Cys Gly Ala Leu Leu Asp Glu Leu Ser Ser
 1               5                  10                  15

Phe Phe Leu Asn Tyr Leu Ala Asp Thr Gln Gly Gly Ser Gly Glu
                20                  25                  30

Glu Gln Leu Tyr Ala Asp Phe Pro Glu Leu Asp Leu Ser Gln Leu Asp
            35                  40                  45

Ala Ser Asp Phe Asp Ser Ala Thr Cys Phe Gly Glu Leu Gln Trp Cys
        50                  55                  60

Pro Glu Asn Ser Glu Thr Glu Pro Asn Gln Tyr Ser Pro Asp Asp Ser
65                  70                  75                  80

Glu Leu Phe Gln Ile Asp Ser Glu Asn Glu Ala Leu Leu Ala Glu Leu
                85                  90                  95

Thr Lys Thr Leu Asp Asp Ile Pro Glu Asp Asp Val Gly Leu Ala Ala
            100                 105                 110

Phe Pro Ala Leu Asp Gly Gly Asp Ala Leu Ser Cys Thr Ser Ala Ser
        115                 120                 125

Pro Ala Pro Ser Ser Ala Pro Ser Pro Ala Pro Glu Lys Pro Ser
130                 135                 140

Ala Pro Ala Pro Glu Val Asp Glu Leu Ser Leu Leu Gln Lys Leu Leu
145                 150                 155                 160

Leu Ala Thr Ser Tyr Pro Thr Ser Ser Asp Thr Gln Lys Glu Gly
                165                 170                 175

Thr Ala Trp Arg Gln Ala Gly Leu Arg Ser Lys Ser Gln Arg Pro Cys
            180                 185                 190

Val Lys Ala Asp Ser Thr Gln Asp Lys Lys Ala Pro Met Met Gln Ser
        195                 200                 205

Gln Ser Arg Ser Cys Thr Glu Leu His Lys His Leu Thr Ser Ala Gln
    210                 215                 220

Cys Cys Leu Gln Asp Arg Gly Leu Gln Pro Cys Leu Gln Ser Pro
225                 230                 235                 240

Arg Leu Pro Ala Lys Glu Asp Lys Glu Pro Gly Glu Asp Cys Pro Ser
                245                 250                 255

Pro Gln Pro Ala Pro Ala Ser Pro Gln Asp Ser Leu Ala Leu Gly Arg
            260                 265                 270

Ala Asp Pro Gly Ala Pro Val Ser Gln Glu Asp Met Gln Ala Met Val
        275                 280                 285

Gln Leu Ile Arg Tyr Met His Thr Tyr Cys Leu Pro Gln Arg Lys Leu
    290                 295                 300

Pro Pro Gln Thr Pro Glu Pro Leu Pro Lys Ala Cys Ser Asn Pro Ser
305                 310                 315                 320

Gln Gln Val Arg Ser Arg Pro Trp Ser Arg His His Lys Ala Ser
                325                 330                 335

Trp Ala Glu Phe Ser Ile Leu Arg Glu Leu Leu Ala Gln Asp Val Leu
            340                 345                 350

Cys Asp Val Ser Lys Pro Tyr Arg Leu Ala Thr Pro Val Tyr Ala Ser
```

-continued

```
                355                 360                 365
Leu Thr Pro Arg Ser Arg Pro Arg Pro Pro Lys Asp Ser Gln Ala Ser
370                 375                 380
Pro Gly Arg Pro Ser Ser Val Glu Glu Val Arg Ile Ala Ala Ser Pro
385                 390                 395                 400
Lys Ser Thr Gly Pro Arg Pro Ser Leu Arg Pro Leu Arg Leu Glu Val
                405                 410                 415
Lys Arg Glu Val Arg Arg Pro Ala Arg Leu Gln Gln Gln Glu Glu Glu
            420                 425                 430
Asp Glu Glu Glu Glu Glu Glu Glu Glu Glu Lys Glu Glu Glu
            435                 440                 445
Glu Glu Trp Gly Arg Lys Arg Pro Gly Arg Gly Leu Pro Trp Thr Lys
450                 455                 460
Leu Gly Arg Lys Leu Glu Ser Ser Val Cys Pro Val Arg Arg Ser Arg
465                 470                 475                 480
Arg Leu Asn Pro Glu Leu Gly Pro Trp Leu Thr Phe Ala Asp Glu Pro
                485                 490                 495
Leu Val Pro Ser Glu Pro Gln Gly Ala Leu Pro Ser Leu Cys Leu Ala
                500                 505                 510
Pro Lys Ala Tyr Asp Val Arg Glu Leu Gly Ser Pro Thr Asp Glu
            515                 520                 525
Asp Ser Gly Gln Asp Gln Gln Leu Leu Arg Gly Pro Gln Ile Pro Ala
530                 535                 540
Leu Glu Ser Pro Cys Glu Ser Gly Cys Gly Asp Met Asp Glu Asp Pro
545                 550                 555                 560
Ser Cys Pro Gln Leu Pro Arg Asp Ser Pro Arg Cys Leu Met Leu
                565                 570                 575
Ala Leu Ser Gln Ser Asp Pro Thr Phe Gly Lys Lys Ser Phe Glu Gln
                580                 585                 590
Thr Leu Thr Val Glu Leu Cys Gly Thr Ala Gly Leu Thr Pro Pro Thr
            595                 600                 605
Thr Pro Pro Tyr Lys Pro Thr Glu Glu Asp Pro Phe Lys Pro Asp Ile
            610                 615                 620
Lys His Ser Leu Gly Lys Glu Ile Ala Leu Ser Leu Pro Ser Pro Glu
625                 630                 635                 640
Gly Leu Ser Leu Lys Ala Thr Pro Gly Ala Ala His Lys Leu Pro Lys
                645                 650                 655
Lys His Pro Glu Arg Ser Glu Leu Leu Ser His Leu Arg His Ala Thr
                660                 665                 670
Ala Gln Pro Ala Ser Gln Ala Gly Gln Lys Arg Pro Phe Ser Cys Ser
                675                 680                 685
Phe Gly Asp His Asp Tyr Cys Gln Val Leu Arg Pro Glu Gly Val Leu
                690                 695                 700
Gln Arg Lys Val Leu Arg Ser Trp Glu Pro Ser Gly Val His Leu Glu
705                 710                 715                 720
Asp Trp Pro Gln Gln Gly Ala Pro Trp Ala Glu Ala Gln Ala Pro Gly
                725                 730                 735
Arg Glu Glu Asp Arg Ser Cys Asp Ala Gly Ala Pro Pro Lys Asp Ser
            740                 745                 750
Thr Leu Leu Arg Asp His Glu Ile Arg Ala Ser Leu Thr Lys His Phe
            755                 760                 765
Gly Leu Leu Glu Thr Ala Leu Glu Glu Glu Asp Leu Ala Ser Cys Lys
770                 775                 780
```

Ser Pro Glu Tyr Asp Thr Val Phe Glu Asp Ser Ser Ser Ser Gly
785                 790                 795                 800

Glu Ser Ser Phe Leu Pro Glu Glu Glu Glu Glu Gly Glu Glu Glu
            805                 810                 815

Glu Glu Asp Asp Glu Glu Glu Asp Ser Gly Val Ser Pro Thr Cys Ser
        820                 825                 830

Asp His Cys Pro Tyr Gln Ser Pro Pro Ser Lys Ala Asn Arg Gln Leu
        835                 840                 845

Cys Ser Arg Ser Arg Ser Ser Gly Ser Ser Pro Cys His Ser Trp
    850                 855                 860

Ser Pro Ala Thr Arg Arg Asn Phe Arg Cys Glu Ser Arg Gly Pro Cys
865                 870                 875                 880

Ser Asp Arg Thr Pro Ser Ile Arg His Ala Arg Lys Arg Arg Glu Lys
                885                 890                 895

Ala Ile Gly Glu Gly Arg Val Val Tyr Ile Gln Asn Leu Ser Ser Asp
            900                 905                 910

Met Ser Ser Arg Glu Leu Lys Arg Arg Phe Glu Val Phe Gly Glu Ile
    915                 920                 925

Glu Glu Cys Glu Val Leu Thr Arg Asn Arg Arg Gly Glu Lys Tyr Gly
    930                 935                 940

Phe Ile Thr Tyr Arg Cys Ser Glu His Ala Ala Leu Ser Leu Thr Lys
945                 950                 955                 960

Gly Ala Ala Leu Arg Lys Arg Asn Glu Pro Ser Phe Gln Leu Ser Tyr
                965                 970                 975

Gly Gly Leu Arg His Phe Cys Trp Pro Arg Tyr Thr Tyr Asp Ser
            980                 985                 990

Asn Ser Glu Glu Ala Leu Pro Ala Ser Gly Lys Ser Lys Tyr Glu Ala
    995                 1000                1005

Met Asp Phe Asp Ser Leu Leu Lys Glu Ala Gln Gln Ser Leu His
    1010                1015                1020

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
agccgtgacc actgacaacg ag                                          22

<210> SEQ ID NO 4
<211> LENGTH: 23
<212> TYPE: DNA
<213> ORGANISM: Artificial Sequence
<220> FEATURE:
<223> OTHER INFORMATION: Synthetic construct

<400> SEQUENCE: 4
gctgcatggt tctgagtgct aag                                         23

<210> SEQ ID NO 5
<211> LENGTH: 22
<212> TYPE: DNA
<213> ORGANISM: Artificial Sequence
<220> FEATURE:
<223> OTHER INFORMATION: Synthetic construct

<400> SEQUENCE: 5

-continued ctccaggaga ctgaatccag ag					22

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
cttgactact gtctgtgagg c					21

<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
cgccatggac gagctggcct tc					22

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
gggaagtcac tgtcttggtt g					21

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
atcggcgcgg aagctgtcgg g					21

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
tcagcaccgc tccgcagacg ag					22

<210> SEQ ID NO 11
<211> LENGTH: 22
<212> TYPE: DNA
<213> ORGANISM: Artificial Sequence
<220> FEATURE:
<223> OTHER INFORMATION: Synthetic construct

<400> SEQUENCE: 11
taccgtctgc acctgctgct gg					22

<210> SEQ ID NO 12
<211> LENGTH: 22
<212> TYPE: DNA

```
<213> ORGANISM: Artificial Sequence
<220> FEATURE:
<223> OTHER INFORMATION: Synthetic construct

<400> SEQUENCE: 12
ggttacactg tgctaggtgt tg                                              22

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
tccaggcgca tgaggctcag c                                               21

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
gcaaagcctc gtgacatcct                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tgtggtgtag cgactgtctg                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
tctctgcctg actgtggttc                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
ttcccagact cctcaaacag                                                 20

<210> SEQ ID NO 18
<211> LENGTH: 22
<212> TYPE: DNA
<213> ORGANISM: Artificial Sequence
<220> FEATURE:
<223> OTHER INFORMATION: Synthetic construct

<400> SEQUENCE: 18
cacgctcaca gtcgctggat ag                                              22
```

<210> SEQ ID NO 19
<211> LENGTH: 22
<212> TYPE: DNA
<213> ORGANISM: Artificial Sequence
<220> FEATURE:
<223> OTHER INFORMATION: Synthetic construct

<400> SEQUENCE: 19
cacttgctcg atgtccatgc tg                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic construct

<400> SEQUENCE: 20
gttgtcagaa gtcctgctgg tg                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic construct

<400> SEQUENCE: 21
ggccacatcc cagacctgct ta                                              22

<210> SEQ ID NO 22
<211> LENGTH: 22
<212> TYPE: DNA
<213> ORGANISM: Artificial Sequence
<220> FEATURE:
<223> OTHER INFORMATION: Synthetic construct

<400> SEQUENCE: 22
gctgcagagc agacttggag gt                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic construct

<400> SEQUENCE: 23
ttccggcaga agaagcctgg gt                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic construct

<400> SEQUENCE: 24
tgaacggtcg tgaggaggac gt                                              22

<210> SEQ ID NO 25
<211> LENGTH: 22
<212> TYPE: DNA
<213> ORGANISM: Artificial Sequence
<220> FEATURE:

<223> OTHER INFORMATION: Synthetic construct

<400> SEQUENCE: 25
caaggtatag gctaggcagg cg                                           22

<210> SEQ ID NO 26
<211> LENGTH: 22
<212> TYPE: DNA
<213> ORGANISM: Artificial Sequence
<220> FEATURE:
<223> OTHER INFORMATION: Synthetic construct

<400> SEQUENCE: 26
cagattatca ttgaagtgac tg                                           22

<210> SEQ ID NO 27
<211> LENGTH: 22
<212> TYPE: DNA
<213> ORGANISM: Artificial Sequence
<220> FEATURE:
<223> OTHER INFORMATION: Synthetic construct

<400> SEQUENCE: 27
gcttcactgc atctgggtga tc                                           22

<210> SEQ ID NO 28
<211> LENGTH: 22
<212> TYPE: DNA
<213> ORGANISM: Artificial Sequence
<220> FEATURE:
<223> OTHER INFORMATION: Synthetic construct

<400> SEQUENCE: 28
cagattatca ttgaagtgac tg                                           22

<210> SEQ ID NO 29
<211> LENGTH: 22
<212> TYPE: DNA
<213> ORGANISM: Artificial Sequence
<220> FEATURE:
<223> OTHER INFORMATION: Synthetic construct

<400> SEQUENCE: 29
gcttcactgc atctgggtga tc                                           22

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
gctcctgtta cagcagagat cg                                           22

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
gctccgcctt taagcgcttc tg                                           22

```
<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
gtgatcgctg acatctgtca c                                              21

<210> SEQ ID NO 33
<211> LENGTH: 23
<212> TYPE: DNA
<213> ORGANISM: Artificial Sequence
<220> FEATURE:
<223> OTHER INFORMATION: Synthetic construct

<400> SEQUENCE: 33
gaataggcga gaaaggccga ttc                                            23

<210> SEQ ID NO 34
<211> LENGTH: 22
<212> TYPE: DNA
<213> ORGANISM: Artificial Sequence
<220> FEATURE:
<223> OTHER INFORMATION: Synthetic construct

<400> SEQUENCE: 34
cctaccgctg tcgccatcga aa                                             22

<210> SEQ ID NO 35
<211> LENGTH: 22
<212> TYPE: DNA
<213> ORGANISM: Artificial Sequence
<220> FEATURE:
<223> OTHER INFORMATION: Synthetic construct

<400> SEQUENCE: 35
ccgttaacgt cgtctctgac ag                                             22

<210> SEQ ID NO 36
<211> LENGTH: 22
<212> TYPE: DNA
<213> ORGANISM: Artificial Sequence
<220> FEATURE:
<223> OTHER INFORMATION: Synthetic construct

<400> SEQUENCE: 36
aagttctggc tggctgtcct ga                                             22

<210> SEQ ID NO 37
<211> LENGTH: 22
<212> TYPE: DNA
<213> ORGANISM: Artificial Sequence
<220> FEATURE:
<223> OTHER INFORMATION: Synthetic construct

<400> SEQUENCE: 37
cacttagccg agtggcgtag ca                                             22

<210> SEQ ID NO 38
<211> LENGTH: 22
<212> TYPE: DNA
<213> ORGANISM: Artificial Sequence
<220> FEATURE:
<223> OTHER INFORMATION: Synthetic construct
```

```
<400> SEQUENCE: 38
atcgcctgcg ccttcacgct ta                                        22

<210> SEQ ID NO 39
<211> LENGTH: 22
<212> TYPE: DNA
<213> ORGANISM: Artificial Sequence
<220> FEATURE:
<223> OTHER INFORMATION: Synthetic construct

<400> SEQUENCE: 39
gttgtcagcc gaccgtagac ct                                        22

<210> SEQ ID NO 40
<211> LENGTH: 22
<212> TYPE: DNA
<213> ORGANISM: Artificial Sequence
<220> FEATURE:
<223> OTHER INFORMATION: Synthetic construct

<400> SEQUENCE: 40
cctggcttcc tgacttctgc ca                                        22

<210> SEQ ID NO 41
<211> LENGTH: 22
<212> TYPE: DNA
<213> ORGANISM: Artificial Sequence
<220> FEATURE:
<223> OTHER INFORMATION: Synthetic construct

<400> SEQUENCE: 41
caggatgttg gcacaccata gc                                        22

<210> SEQ ID NO 42
<211> LENGTH: 21
<212> TYPE: DNA
<213> ORGANISM: Artificial Sequence
<220> FEATURE:
<223> OTHER INFORMATION: Synthetic construct

<400> SEQUENCE: 42
cctgcatgag gcagctggag a                                         21

<210> SEQ ID NO 43
<211> LENGTH: 24
<212> TYPE: DNA
<213> ORGANISM: Artificial Sequence
<220> FEATURE:
<223> OTHER INFORMATION: Synthetic construct

<400> SEQUENCE: 43
tcagtgcctc gcagccttgc agat                                      24

<210> SEQ ID NO 44
<211> LENGTH: 22
<212> TYPE: DNA
<213> ORGANISM: Artificial Sequence
<220> FEATURE:
<223> OTHER INFORMATION: Synthetic construct

<400> SEQUENCE: 44
cgagtgcccg gatggctccg at                                        22

<210> SEQ ID NO 45
<211> LENGTH: 22
```

```
<212> TYPE: DNA
<213> ORGANISM: Artificial Sequence
<220> FEATURE:
<223> OTHER INFORMATION: Synthetic construct

<400> SEQUENCE: 45
catccgagcc attttcacag tc                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic construct

<400> SEQUENCE: 46
gttctgcaga ggatcttcag gc                                              22

<210> SEQ ID NO 47
<211> LENGTH: 22
<212> TYPE: DNA
<213> ORGANISM: Artificial Sequence
<220> FEATURE:
<223> OTHER INFORMATION: Synthetic construct

<400> SEQUENCE: 47
gtcctccaga tgcctgtcgc tt                                              22

<210> SEQ ID NO 48
<211> LENGTH: 22
<212> TYPE: DNA
<213> ORGANISM: Artificial Sequence
<220> FEATURE:
<223> OTHER INFORMATION: Synthetic construct

<400> SEQUENCE: 48
cctcatcatt gccaacacca tg                                              22

<210> SEQ ID NO 49
<211> LENGTH: 22
<212> TYPE: DNA
<213> ORGANISM: Artificial Sequence
<220> FEATURE:
<223> OTHER INFORMATION: Synthetic construct

<400> SEQUENCE: 49
tgtttgcgca caagcagcca ac                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic construct

<400> SEQUENCE: 50
caggaactga acggcattac tc                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic construct

<400> SEQUENCE: 51
```

```
cattttctag ggataacagc ac                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic construct

<400> SEQUENCE: 52
agtctgcgct ggagtctctg gc                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic construct

<400> SEQUENCE: 53
caacagtgac gaagcctgca tg                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic construct

<400> SEQUENCE: 54
gccatcagtt cattcctgaa tg                                              22

<210> SEQ ID NO 55
<211> LENGTH: 21
<212> TYPE: DNA
<213> ORGANISM: Artificial Sequence
<220> FEATURE:
<223> OTHER INFORMATION: Synthetic construct

<400> SEQUENCE: 55
acctccgaga gctgctgctt g                                               21

<210> SEQ ID NO 56
<211> LENGTH: 20
<212> TYPE: DNA
<213> ORGANISM: Artificial Sequence
<220> FEATURE:
<223> OTHER INFORMATION: Synthetic construct

<400> SEQUENCE: 56
actgcagcat cgtgtactgg                                                 20

<210> SEQ ID NO 57
<211> LENGTH: 20
<212> TYPE: DNA
<213> ORGANISM: Artificial Sequence
<220> FEATURE:
<223> OTHER INFORMATION: Synthetic construct

<400> SEQUENCE: 57
gggatggtgt caaagctgac                                                 20

<210> SEQ ID NO 58
<211> LENGTH: 21
<212> TYPE: DNA
<213> ORGANISM: Artificial Sequence
```

```
<220> FEATURE:
<223> OTHER INFORMATION: Synthetic construct

<400> SEQUENCE: 58
atgcgcctgc ccaagacctt c                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic construct

<400> SEQUENCE: 59
ccgatgctca ctcttcggcg c                                              21

<210> SEQ ID NO 60
<211> LENGTH: 19
<212> TYPE: DNA
<213> ORGANISM: Artificial Sequence
<220> FEATURE:
<223> OTHER INFORMATION: Synthetic construct

<400> SEQUENCE: 60
gatatcctct gtgatgtta                                                 19

<210> SEQ ID NO 61
<211> LENGTH: 19
<212> TYPE: DNA
<213> ORGANISM: Artificial Sequence
<220> FEATURE:
<223> OTHER INFORMATION: Synthetic construct

<400> SEQUENCE: 61
gtacggaact gcataagca                                                 19
```

COMPOSITIONS AND METHODS FOR MODULATING PGC-1β TO TREAT LIPID-RELATED DISEASES AND DISORDERS

GOVERNMENT RIGHTS

This invention was made at least in part with support by a grant awarded from the National Institutes of Health, grant number 5R01DK54477. The U.S. government may have certain rights in the invention.

BACKGROUND OF THE INVENTION

Obesity and type 2 diabetes are associated with an increased risk of developing cardiovascular disease, a leading cause of morbidity and mortality in developed countries (Flier (2004) *Cell* 116, 337-350; Reaven et al., (2004) *Recent Prog. Horm. Res.* 59, 207-223; Zimmet et al., (2001) *Nature* 414, 782-787). The predisposition of developing atherosclerosis appears to be the consequence of pathogenic dyslipidemia in insulin-resistant states, which is characterized by hypertriglyceridemia, as well as increased concentrations of low-density lipoprotein (LDL) cholesterol and reduced levels of high-density lipoprotein (HDL) cholesterol (Betteridge (1999) *Eur. J. Clin. Invest* 29 Suppl. 2, 12-16; Goldberg (2001) *J. Clin. Endocrinol. Metab.* 86, 965-971). Genetic and epidemiological studies have provided compelling evidence that plasma LDL cholesterol correlates positively with the risk of developing cardiovascular disease (Breslow (2000) *Annu. Rev. Genet.* 34, 233-254; Sacks and Katan (2002) *Am. J. Med.* 113 Suppl. 9B, 13S-24S). In addition, increased plasma triglyceride levels have been shown to be an independent risk factor for coronary heart disease. Although genetic factors, environmental influences, and importantly, the interaction of the two all contribute to the progression of cardiovascular disease, it is now understood that dietary intake of saturated and trans fats significantly raises plasma LDL cholesterol while lowering HDL cholesterol (Sacks and Katan (2002) *Am. J. Med.* 113 Suppl. 9B, 13S-24S; Spady et al. (1993) *Annu. Rev. Nutr.* 13, 355-381). In fact, dietary intake of saturated and trans fats have a greater hyperlipidemic effect than the intake of cholesterol itself. Despite the strong connection between dietary intake of saturated and trans fats and atherogenic lipid profiles the metabolic pathways and mechanistic basis leading from these lipids to elevated cholesterol levels have been unclear.

The liver plays a central role in the maintenance of systemic lipid homeostasis. Hepatocytes are responsible for the synthesis and secretion of very low-density lipoprotein (VLDL), a precursor for the atherogenic LDL particles. The role of VLDL is to redistribute lipids, primarily triglycerides, for storage and utilization by peripheral tissues. In humans, the liver is also the primary site of de novo lipid synthesis. Hepatic lipogenesis is controlled mainly at the level of gene transcription (Girard et al. (1997) *Annu. Rev. Nutr.* 17, 325-352; Hellerstein et al. (1996) *Annu. Rev. Nutr* 16, 523-557). Several transcription factors in the sterol responsive element binding protein (SREBP) family have been shown to be key regulators of the transcriptional activation of lipogenic genes (Horton et al. (2002) *J. Clin. Invest.* 109, 1125-1131). All SREBP isoforms are synthesized as precursor proteins in the endoplasmic reticulum membrane and undergo two steps of proteolytic cleavage (Brown and Goldstein (1997) *Cell* 89, 331-340). This leads to release of the N-terminal active forms which subsequently translocate into nucleus and stimulate the expression of target genes. SREBP1a and 1c isoforms (also known as ADD1) are derived from a single gene by alternative usage of transcription start sites, resulting in two proteins with different amino termini (Shimlomura et al. (1997) *J. Clin. Invest.* 99, 838-845; Tontonoz et al. (1993) Mol. *Cell. Bio.* 13, 4753-4759); Yokoyama et al. (1993) *Cell* 75, 187-197), while SREBP2 is encoded by a different gene (Hua et al. (1993) *Proc. Natl. Acad. Sci.* USA 90, 11603-11607). The activity of SREBPs is regulated by several mechanisms. For example, SREBP 1c mRNA is highly inducible in both fat cells and liver by insulin (Kim et al. (1998) *J. Clin. Invest.* 101, 1-9; Shimomura et al. (1999) *Proc. Natl. Acad. Sci.* USA 96, 13656-13661), whereas the proteolytic processing of SREBP2 in cells is stimulated in response to sterol-depletion (Brown and Goldstein (1997) *Cell* 89, 331-340; Sakai et al. (1996) *Cell* 85, 1037-1046). Studies in cell culture or mouse liver revealed that SREBP1c and SREBP2 preferentially regulate the expression of genes involved in fatty acid and cholesterol synthesis, respectively (Horton et al. (1998) *J. Clin. Invest.* 101, 2331-2339; Kim and Spiegelman (1996) *Genes Dev.* 10, 1096-1107). In contrast, SREBP1a appears to activate both pathways (Horton et al. (2003) *Proc. Natl. Acad. Sci.* USA 100, 12027-12032; Pai et al. (1998) *J. Biol. Chem.* 273, 26138-26148). Notably, all three SREBPs induce a severe fatty liver phenotype in transgenic mice with abundant accumulation of triglycerides and cholesterol, suggestive of an imbalance between lipid synthesis and secretion in the transgenic hepatocytes (Horton et al. (1998) *J. Clin. Invest.* 101, 2331-2339; Shimano et al. (1996) *J. Clin. Invest.* 98, 1575-1584; Shimano et al. (1997) *J. Clin. Invest.* 99, 846-854). In addition, hepatic lipogenesis in healthy animals and humans is correlated to lipoprotein secretion causing hepatic steatosis not to develop.

Transcription factors function via docking of coactivator proteins. The coactivators that function with the SREBPs in hepatic lipogenesis have been largely unexplored. Recent studies indicate that the PGC-1 family of coactivators play an important role in liver metabolism (Puigserver and Spiegelman (2003) *Endocr. Rev.* 24, 78-90).

PGC-1β is a recently identified transcriptional coactivator closely related to PGC-1a whose biological activities have been unknown (Kressler et al. (2002) *J. Biol. Chem.* 277, 13918-13925; Lin et al. (2002a) *J. Biol. Chem.* 277, 1645-1648). Although PGC-1β shares a similar tissue distribution with PGC-1β, these two coactivators appear to be differentially regulated during development and in response to changes in nutritional status (Kamei et al. (2003) *Proc. Natl. Acad. Sci. USA* 100, 12378-12383; Lin et al. (2002a) *J. Biol. Chem.* 277, 1645-1648; Lin et al. (2003) *J. Biol. Chem.* 278, 30843-30848). Like PGC-1a, PGC-1β strongly activates mitochondrial biogenesis and cellular respiration in differentiated myotubes and hepatocytes (Lin et al. (2003) *J. Biol. Chem.* 278, 30843-30848; St-Pierre et al. (2003) *J. Biol. Chem.* 278, 26597-26603). However, PGC-1β has no apparent effects on the expression of gluconeogenic genes, probably reflecting its lack of ability to coactivate HNF4β and FOXO1, key regulators of hepatic gluconeogenesis.

SUMMARY OF THE INVENTION

The present invention is based, at least in part, on the discovery that PGC-1β is involved in the regulation of lipid biosynthesis and lipid transport, and therefore regulates biosynthesis and transport of triglycerides and cholesterol, e.g., VLDL cholesterol and LDL cholesterol, e.g., in the liver. The present invention is also based on the discovery that PGC-1β is induced in liver and isolated hepatocytes by saturated fats and trans fatty acids, but not by cholesterol and unsaturated fatty acids.

Accordingly, in one aspect, the present invention provides a method for treating and/or preventing a lipid-related disease or disorder in a subject, e.g., a mammal, e.g., a human, dog, cat, horse, cow, or sheep, by administering a PGC-1β modulator. In one embodiment, the lipid-related disease or disorder is indicated by elevated levels of VLDL cholesterol, LDL cholesterol, or triglycerides. Examples of lipid-related diseases or disorders include, e.g., hyperlipidemia, hypertriglyceridemia, hypercholesterolemia, cardiovascular disease, obesity, and type II diabetes.

In one embodiment, a PGC-1β modulator used in the methods of the invention is capable of modulating PGC-1β, e.g., decreasing the expression or activity of PGC-1β. In another embodiment, a PGC-1β modulator is capable of modulating PGC-1β polypeptide activity. In yet another embodiment, the modulator is a PGC-1β polypeptide comprising the amino acid sequence of SEQ ID NO: 2, or a fragment thereof. In still another embodiment, the modulator includes a PGC-1β polypeptide comprising an amino acid sequence which is at least 60, 65, 70, 75, 80, 85, 90, or 95 percent identical to the amino acid sequence of SEQ ID NO: 2.

In another embodiment, the PGC-1β modulator is an isolated naturally occurring allelic variant of a polypeptide consisting of the amino acid sequence of SEQ ID NO:2, wherein the polypeptide is encoded by a nucleic acid molecule which hybridizes to a complement of a nucleic acid molecule consisting of SEQ ID NO: 1 at 6×SSC at 45° C., followed by one or more washes in 0.2×SSC, 0.1% SDS at 65° C.

In yet another embodiment, the PGC-1β modulator is capable of modulating PGC-1β nucleic acid expression. For example, the PGC-1β modulator includes a PGC-1β nucleic acid molecule, e.g., a PGC-1β nucleic acid molecule comprising the nucleotide sequence of SEQ ID NO:1, or a fragment thereof. In another embodiment, the PGC-1β modulator is ah antisense PGC-1β nucleic acid molecule, a ribozyme, or an RNA interfering agent, e.g., an siRNA molecule, which targets PGC-1β.

In still another embodiment, a PGC-1β modulator is capable of modulating the expression or activity of an SREBP transcription factor. In still a further embodiment, a PGC-1β, modulator is capable of modulating the expression or activity of lipogenic genes, e.g., FAS, SCD-1, HMG-CoA reductase, DGAT, and GPAT. In yet a further embodiment, a PGC-1β modulator is capable of modulating the expression or activity of a liver X receptor (LXR), e.g., LXRα target gene, e.g., PLTP, ABCA1 and ABCG1. PGC-1β modulators include, but are not limited to, small molecules, nucleic acid molecules, RNA interfering agents, e.g., siRNAs, antibodies, polypeptides, and peptides or peptidomimetics.

In another aspect, the invention provides a method of modulating lipid biosynthesis in a cell by contacting a cell, e.g., a hepatocyte, with a PGC-1β modulator such that lipid biosynthesis is modulated. In a preferred embodiment, lipid biosynthesis is modulated by an SREBP transcription factor, e.g., SREBP1a, SREBP1c or SREBP2. In another embodiment, the lipid is a triglyceride or cholesterol, e.g., VLDL or LDL cholesterol.

In yet another aspect, the invention provides a method for modulating lipid transport from a cell by contacting the cell with a PGC-1β modulator such that lipid transport is modulated. In one embodiment, lipid transport is modulated by LXR, e.g., LXRα.

In still another aspect, the invention provides a method for modulating lipid biosynthesis and lipid transport from a cell, e.g., a hepatocyte, by contacting the cell with a PGC-1β modulator such that lipid biosynthesis and lipid transport are modulated.

In still a further aspect, the invention provides a method of modulating at least one of lipid biosynthesis and lipid transport in a subject, e.g., a mammal, e.g., a human, dog, cat, horse, cow, or sheep, by administering to the subject a PGC-1β modulator. In one embodiment, the PGC-1β modulator is capable of modulating the ability of PGC-1β to bind to an SREBP transcription factor, e.g., SERBP1a, SREBP1c, and SREBP2. In another embodiment, the PGC-1β modulator is capable of modulating the ability of PGC-1β to bind to LXRα. In yet another embodiment, the lipid is a triglyceride or cholesterol, e.g., VLDL or LDL cholesterol. In still a further embodiment, the lipid biosynthesis and/or lipid transport is in the liver.

In another aspect, the invention provides a method of modulating at least one of plasma triglyceride level and plasma cholesterol level, e.g., VLDL or LDL, level in a subject by administering to the subject a PGC-1β modulator.

In yet another aspect, the invention provides methods for identifying a compound capable of treating or preventing a lipid-related disease or disorder comprising the step of assaying the ability of the compound to modulate PGC-1β nucleic acid expression or PGC-1β polypeptide activity.

In yet a further aspect, the invention provides methods for identifying a compound, capable of treating or preventing a lipid-related disease or disorder by assaying the ability of the compound to modulate PGC-1β nucleic acid expression or PGC-1β polypeptide activity. In one embodiment, a PGC-1β modulating compound is determined by detecting modulation in the expression or activity of lipogenic genes, e.g., FAS, SCD-1, HMG-CoA reductase, DGAT, and GPAT. In another embodiment, a PGC-1β modulating compound is determined by detecting modulation in the expression or activity of an SREBP transcription factor, e.g., SREBP1a, SREBP1c and SREBP2. In yet another embodiment, a PGC-1β modulating compound is determined by detecting modulation in the expression or activity of an LXR target gene, e.g., PLTP, ABCA1 and ABCG1. In yet a further embodiment, a PGC-1β modulating compound is determined by detecting modulation in at least one of plasma levels of cholesterol and plasma levels of triglycerides. In still a further embodiment, a PGC-1β modulating compound is determined by detecting modulation of cholesterol homeostasis.

In another aspect, the invention provides methods for identifying a compound capable of modulating triglyceride level and plasma cholesterol level in a subject by assaying the ability of the compound to modulate PGC-1β nucleic acid expression or PGC-1β polypeptide activity.

In yet another aspect, the invention provides methods for identifying a compound capable of modulating at least one of lipid biosynthesis and lipid transport by assaying the ability of the compound to modulate PGC-1β expression or activity. In one embodiment, the lipid is at least one of a triglyceride and cholesterol, e.g., VLDL or LDL cholesterol. In still a further embodiment, the lipid biosynthesis and/or lipid transport is in the liver.

In yet a further aspect, the invention provides a method of assessing the efficacy of a test compound for inhibiting a lipid-related disease or disorder in a subject, e.g., a human, by comparing the level of PGC-1β expression or activity in a first sample obtained from the subject and maintained in the presence of the test compound and the level of PGC-1β expression or activity in a second sample obtained from the subject and maintained in the absence of the test compound.

In another aspect, the invention provides a method of assessing the efficacy of a therapy for inhibiting a lipid-related disease or disorder in a subject by comparing the level of PGC-1β expression or activity in a first sample obtained from the subject prior to providing at least a portion of the therapy to the subject and the level of PGC-1β expression or activity in a second sample obtained from the subject following provision of the portion of the therapy.

In yet another aspect, the invention provides a method for assessing whether a subject is afflicted with a lipid-related disease or disorder or is at risk of developing a lipid-related disease or disorder by detecting PGC-1β expression or activity in a cell or tissue of a subject, e.g., a liver cell.

In still another aspect, the invention provides a method of classifying dietary constituents, by contacting a cell, e.g., a hepatocyte, with a sample containing at least one dietary constituent and measuring PGC-1β expression or activity. In one embodiment, an increase in PGC-1β expression or activity indicates the presence of a fatty acid, e.g., a trans fat or a saturated fat having a high atherogenic potential.

In still a further aspect, the present invention provides methods of detecting for the presence of an atherogenic fatty acid in a sample by contacting a cell, e.g., a hepatocyte, with a sample and measuring PGC-1β expression or activity, thereby detecting the presence of an atherogenic fatty acid in the sample. In one embodiment, an increase in the expression or activity of PGC-1β indicates the presence of an atherogenic fatty acid e.g., trans fat or a saturated fat in the sample.

BRIEF DESCRIPTION OF THE DRAWINGS

FIG. 1A depicts a cluster analysis of liver gene expression in response to high-fat feeding. FIG. 1A exemplifies genes involved in hepatic lipogenesis that are induced more than 1.8-fold in response to high-fat feeding. A representative probe set was used in generating the tree in the event multiple probe sets were available for a single gene. SREBP1c and PGC-1β were included in this lipogenic cluster. FIG. 1B depicts the real-time PCR analysis of total liver RNA from mice fed a high-fat diet for 1 day (hatched box) or 2 days (filled box). Relative mRNA abundance was calculated by normalization to the control chow values (open box); N=4;*: p<0.01. FIG. 1C depicts the real-time PCR analysis of total liver RNA from mice fed a control diet containing 0.07% cholesterol (open box) or a diet containing 2% cholesterol for 1 day (hatched box) or 2 days (filled box). Values were normalized to those from mice fed the control diet; N=4;*: p<0.02. FIG. 1D depicts the regulation of PGC-1β expression by free fatty acids in isolated hepatocytes. Primary hepatocytes were treated with 400 μM of various fatty acids for 4 hours. Total RNA was isolated and analyzed by realtime PCR using primers specific for PGC-1β (filled box) and PGC-1β (open box); *: p<0.01.

FIG. 2A depicts H2.35 mouse hepatoma cells that were transiently transfected with either the wild-type FAS promoter (FAS—700 luc) or the SRE mutant (FAS—700 ΔSRE luc) reporter constructs, in combination with SREBP1c in the presence or absence of the PGC-1s. FIG. 2B depicts transient transfection of FAS—700 luc reporter plasmid with SREBP2 in the presence or absence of the PGC-1s. FIG. 2C depicts chip analysis on SREBP target genes. Hepatoma cells were infected with adenoviruses for two days and harvested for CHIP analysis with anti-Flag antibody or control IgG (bottom). The precipitated genomic fragments were amplified using primers flanking SREs on the FAS and LDLR promoters or control GAPDH promoter. Genomic DNA from total chromatin lysates was included as an input control. FIG. 2D depicts the co-immunoprecipitation of PGC-1β and SREBP1c. Cultured 293 cells were transfected with plasmids as indicated. Total lysates from transfected cells were subjected to immunoprecipitation using antibodies specific for SREBP1c. Both lysates and precipitates were analyzed by immunoblotting with antibodies specific for SREBP1c or the Flag epitope tag. Arrows indicate the bands corresponding to Flag-PGC-1α (f-PGC-1α), Flag-PGC-1β (f-PGC-1) and SREBP1c. FIG. 2E depicts the mapping of PGC-1β domains that interact with SREBP1c. Glutathione beads containing immobilized GST (−) or GST-SREBP1c (+) were incubated with in vitro translated 35-S-labeled full length PGC-1β or truncated PGC-1β mutants. Shown in the left are in vitro translated PGC-1β mutants equivalent to 10% of input for the interaction assay. The numbers above the gel denote amino acid positions of the mutants. Note that a domain between amino acids 350 and 530 of PGC-1β is necessary for the docking of SREBP1c. FIG. 2F is a diagram of the structure of PGC-1α and PGC-1β showing that a domain unique for PGC-1β that provides the docking site for SREBP1c.

FIG. 3A depicts the hybridization analysis of total liver RNA from rats transduced with the control adenovirus (Ad-β-Gal), Ad-PGC-1β or Ad-PGC-1β. A probe specific for ribosomal protein 36B4 was included as a loading control. FIG. 3B further depicts the induction of hepatic mRNAs encoding enzymes in the cholesterol biosynthesis pathway by PGC-1β when compared to the high-fat fed mouse liver. The expression levels for high-fat fed mouse liver represent normalized values obtained from the Affymetrix™ arrays. The expression of these genes in response to PGC-1s was determined by realtime PCR analysis of total RNA from rat liver transduced with adenoviral vectors as indicated. PGC-1β is able induce the expression of multiple enzymes involved in cholesterol biosynthesis, which are also induced in response to high-fat feeding. FIG. 3C depicts the membrane and nuclear forms of rat SREBP1c protein. The results demonstrate that PGC-1β activity had no effect on the expression and processing of SREBP1c in rat liver.

FIG. 4D depicts an analysis of lipoprotein profiles. Plasma from rats transduced with the control Ad-β-Gal or Ad-PGC-1β was fractionated by FPLC. Triglyceride and cholesterol concentrations in each fraction were measured. FIG. 4E depicts relative lipid content in VLDL fractions which were calculated using areas under curve in panel (D). FIG. 4E illustrates a drastic increase in VLDL triglycerides and cholesterol in plasma from rats transduced with Ad-PGC-1β when compared to the control β-Gal.

FIG. 5A depicts plasma triglyceride concentrations in rats transduced with adenoviral vectors expressing control β-Gal, PGC-1β, dominant negative SREBP1c (DN), or the combination of PGC-1β and DN, *: p<0.0001 (PGC-1β versus β-Gal), **: p<0.02 (PGC-1β versus PGC-1β+DN). FIG. 5B depicts realtime PCR analysis of hepatic gene expression in adenovirally transduced rats, *:p<0.001 (PGC-1β versus PGC-1β+DN).

FIG. 6A depicts H2.35 hepatoma cells that were transiently transfected with 4×LXRE-luc in combination with plasmids. Transfected cells were treated with either vehicle DMSO (open box) or 10 μM of the LXR agonist T0901317 (filled box) for 24 hours before luciferase assay. FIG. 6B depicts H2.35 hepatoma cells that were transiently transfected with wild-type ABCA1 promoter reporter plasmid-(ABCA1-luc) or a mutant lacking the LXRE (ABCA1 ΔLXRE-luc) in combination with plasmids. Transfected cells were treated with vehicle or T0901317 as described in FIG. 6A. FIG. 6C depicts CHIP analysis on LXR target genes. H2.35 cells were infected with adenoviruses expressing GFP, flag-PGC-1α or flag-PGC-1β. Cells were treated with 10 μM of T0901317 for 3 hours before harvesting. PCR was performed on input or precipitated DNA using primers as indicated FIG. 6D depicts the interaction between LXRα and the N-termini of the PGC-1β proteins. In vitro translated LXRα was incubated with GST, or fusion proteins of GST and the N-termini of PGC-1s. The binding reactions were incubated in the presence (+) or absence (−) of 10 μM T0901317. Shown in the left is 10% of LXRα input for the reactions. FIG. 6E depicts the induction of endogenous LXR target genes by PGC-1α and PGC-1β. Real-time PCR analysis of total liver RNA isolated from rats transduced with Ad-β-Gal (open box), Ad-PGC-1α (hatched box) or Ad-PGC-1β (filled box). Primers specific for 18S rRNA were used as an internal control for normalization.

FIGS. 7A-H illustrate the requirement for PGC-1β in SREBP-mediated transcription. In particular, FIG. 7A depicts knockdown of PGC-1β protein levels by RNAi constructs. Cultured 293 cells were transiently transfected with PGC-1β expression plasmid (f-PGC-1β) in the presence of RNAi constructs or a vector control. Transfected cells were harvested for immunoblotting using a monoclonal antibody against the Flag epitope. Both RNAi constructs decrease PGC-1β protein levels compared to the vector control. FIG. 7F depicts knockdown of PGC-1β protein by adenoviral expression of RNAi. H2.35 hepatoma cells were infected with Ad-GFP or Ad-RNAi for two days and then infected with Ad-PGC-1β. Total lysates were prepared for immunoblotting analysis using antibodies raised against PGC-1β. FIG. 7G illustrates the requirement for PGC-1β in the induction of endogenous SREBP target genes. H2.35 hepatoma cells were infected with Ad-GFP (filled box) or Ad-RNAi (open box) for two days, and then infected with Ad-SREBP1c for 20 hours. Total RNA was isolated from infected cells and analyzed by real-time PCR using primers specific for the genes. FIG. 7H depicts the infection of H2.35 hepatoma cells with Ad-GFP (filled box) or Ad-RNAi (open box) for two days, followed by a treatment of 10 μM of T0901317 as indicated. Relative SREBP1c expression was determined by real-time PCR analysis and normalized to 18S rRNA.

FIG. 8A depicts the knockdown of endogenous PGC-1β in the livers from mice transduced with Ad-RNAi. 80 μg of liver lysates from mice receiving control or RNAi adenoviruses were subjected to immunoblotting analysis using PGC-1β antibody. FIG. 8B depicts hepatic gene expression in the mice transduced with control (filled box, n=5) or RNAi (open box, n=76) adenoviruses, *p<0.03. FIG. 8C depicts the concentrations of liver and plasma triglycerides in the mice transduced with control (filled box) or RNAi (open box) adenoviruses. Plasma triglyceride concentrations were measured before (chow) or after (HF) two days of high-fat feeding as indicated. *p<0.03; **p=0.0002. FIG. 8D depicts the concentrations of total and HDL/non-HDL plasma cholesterol in the mice transduced with control (filled box) or RNAi (open box) adenoviruses. HDL cholesterol was measured in animals after two days of high-fat feeding. Non-HDL cholesterol was calculated by subtracting HDL from total cholesterol. *p<0.03; **p=0.02.

DETAILED DESCRIPTION OF THE INVENTION

Figure 1:
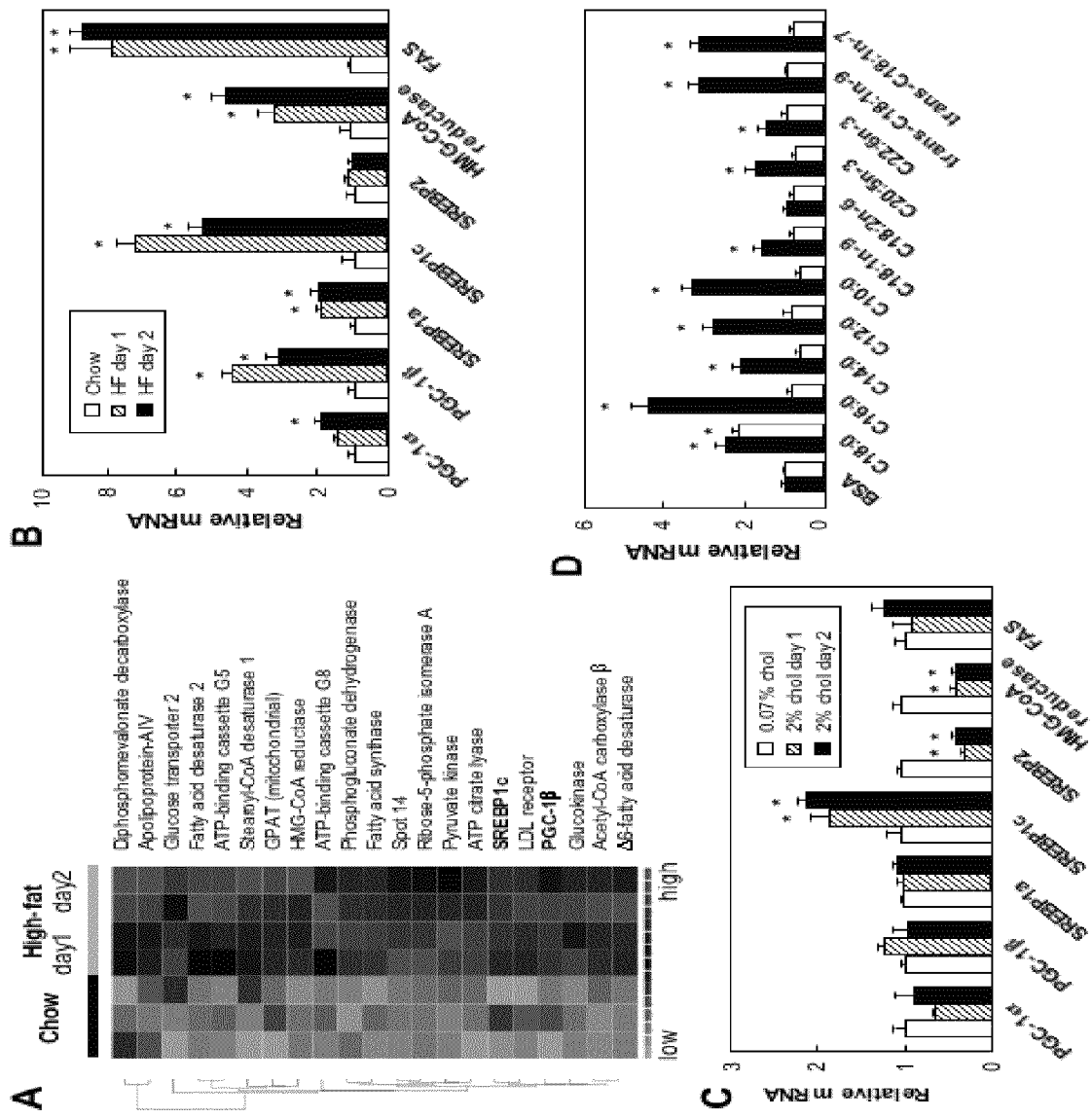
FIGS. 1A-D depict the induction of PGC-1β expression by dietary intake of saturated fats. In particular.

The present invention is based, at least in part, on the discovery that PGC-1β is involved in the regulation of lipid biosynthesis and lipid transport, and regulates the biosynthesis and transport of triglycerides and cholesterol, e.g., VLDL cholesterol and LDL cholesterol, e.g., in the liver. PGC-1β coactivates the SREBP transcription factors, e.g., SREBP1a, SREBP1c and SREBP2 to effect lipid biosynthesis and coactivates LXRα to effect lipid transport and secretion. Increased expression or activity of PGC-1β leads to increased levels of circulating triglycerides and cholesterol and decreased hepatic steatosis in a subject. Thus, the induction of PGC-1β is a key step linking the dietary intake of saturated and trans fats with the elevation of circulating cholesterol. Therefore, modulation of PGC-1β, e.g., modulation of the expression or activity of PGC-1β and/or the pathways controlled by PGC-1β, through genetic or pharmacological methods, modulates lipid biosynthesis, lipid transport, plasma triglyceride levels and plasma cholesterol levels to thereby treat and/or prevent a lipid-related disease or disorder in a subject, e.g., hyperlipidemia, hypertriglyceridemia, hypercholesterolemia, cardiovascular disease, obesity, and type II diabetes.

Accordingly, in one aspect, the invention provides methods for treating or preventing a lipid-related disease or disorder in a subject comprising administering to the subject a PGC-1β modulator. In another aspect, the invention provides methods for identifying a compound which modulates the expression or activity of PGC-1α. The methods include contacting PGC-1α or a cell expressing PGC-1α with a test compound and determining the effect of the test compound on the expression or activity of PGC-1α to thereby identify a compound which modulates, e.g., increases or decreases, PGC-1α expression or activity.

The present invention is also based on the discovery that PGC-1β is induced in liver and isolated hepatocytes by saturated fats and trans fatty acids, but not by cholesterol and unsaturated fatty acids. Thus, PGC-1β may be used to identify and classify dietary constituents in order to predict the effect of these constituents on blood lipid profiles in a subject. Accordingly, the present invention provides methods of classifying dietary constituents and atherogenic fatty acids by contacting a cell, e.g., a hepatocyte, with a sample containing dietary constituents or fatty acids and measuring modulation of PGC-1β expression or activity. In another aspect, the present invention provides methods of classifying dietary constituents and atherogenic fatty acids by administering a dietary constituent or atherogenic fatty acid to a subject, e.g., a mammal, and measuring modulation of PGC-1β expression or activity. An increase in PGC-1β expression or activity indicates the presence of a fatty acid, e.g., a trans fat or a saturated fat, which has a high atherogenic potential. Dietary constituents having a high atherogenic potential may cause an increase in lipid biosynthesis, lipid transport, triglyceride levels, and/or plasma cholesterol levels in a subject and also may lead to the development of a lipid-related disease or disorder in a subject. Methods for measuring modulation of PGC-1B expression or activity are set forth herein.

DEFINITIONS

As used herein, the term "modulator of PGC-1β expression or activity" includes a compound or agent that is capable of modulating or regulating PGC-1β expression or at least one PGC-1β activity, as described herein. A modulator of PGC-1β expression or activity can be an inducer of PGC-1β expression or activity or an inhibitor of PGC-1β expression or activity. As used herein, an "inducer or agonist of PGC-1β activity" agonizes, stimulates, enhances, and/or mimics a PGC-1β activity, either completely or partially. An "inducer or agonist of PGC-1β expression" increases, enhances, or stimulates PGC-1β expression, either completely or partially, directly or indirectly. As used herein, an "inhibitor or antagonist of PGC-1β activity" antagonizes, reduces, or blocks PGC-1β activity, either completely or partially. An "inhibitor or antagonist of PGC-1β expression" reduces or blocks PGC-1β expression, either completely or partially, directly or indirectly. Examples of PGC-1β inhibitors include small molecules, antisense PGC-1β nucleic acid molecules, ribozymes, siRNA molecules, and anti-PGC-1β antibodies. Examples of PGC-1β inducers include PGC-1β mimetics, e.g., peptidomimetics, small molecules, nucleic acid molecules encoding PGC-1β, and PGC-1β proteins or fragments thereof.

As used interchangeably herein, a "PGC-1β activity", "biological activity of PGC-1β" or "functional activity of PGC-1β" refers to an activity exerted by a PGC-1β polypeptide or nucleic acid molecule on a PGC-1β responsive molecule, cell, or tissue, as determined in vitro and/or in vivo, according to standard techniques. In an exemplary embodiment, a PGC-1β activity is the ability to modulate the expression or activity of lipogenic genes, e.g., FAS, SCD-1, HMG-CoA reductase, DGAT, and GPAT. In another embodiment, PGC-1β activity is the ability to modulate the expression or activity of LXR/RXR, LXRα, or an LXRα target gene, e.g., PLTP, ABCA1 and ABCG1. In yet another embodiment, PGC-1β activity is the ability to modulate expression or activity of an SREBP transcription factor, e.g., SREBP1a, SREBP1c and SREBP2. Instill another embodiment a PGC-1β activity is the ability to modulate lipid biosynthesis and/or lipid transport, e.g., in the liver. In another embodiment, PGC-1β activity is the ability to modulate plasma triglyceride levels and/or plasma cholesterol levels. In a still another embodiment, PGC-1β activity is the ability to modulate a lipid-related disease or disorder in a subject.

As used herein, the term "lipid-related disease or disorder" includes any disease, disorder, or condition which is caused by or related to dysfunction or deficiency of lipid metabolism, including, but not limited to, lipid biosynthesis, lipid transport, triglyceride levels, plasma levels, plasma cholesterol levels or misregulation or modulation of any lipid specific pathway or activity. Lipid-related diseases or disorders include obesity and obesity-related diseases and disorders such as obesity, impaired glucose tolerance (IGT), insulin resistance, atherosclerosis, atheromatous disease, heart disease, hypertension, stroke, Syndrome X, Noninsulin Dependent Diabetes Mellitus (NIDDM, or Type H diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, anorexia, and bulimia.

As used herein, the term "cholesterol level" refers to the level of serum cholesterol in a subject or the level of cholesterol forms such as HDL cholesterol, LDL, cholesterol, and VLDL cholesterol, etc.

As used herein, the term "low density lipoprotein" or "HDL" is defined in accordance with common usage of those of skill in the art. Generally, LDL refers to the lipid-protein complex which, when isolated by ultracentrifugation, is found in the density range d=1.019 to d=1.063.

As used herein, the term "high density lipoprotein" or "HDL" is defined in accordance with common usage of those of skill in the art. Generally "HDL" refers to a lipid-protein complex which, when isolated by ultracentrifugation, is found in the density range of d=1.063 to d=1.21.

As used herein, the term "dietary constituents" includes any component of food and drink consumed by an organism, e.g., a mammal. Dietary constituents include, but are not limited to, lipids including, for example, cholesterol, e.g., LDL, VLDL, and HDL, dietary fat, fatty acids, e.g., saturated fatty acids, unsaturated fatty acids, trans fatty acids, fiber, carbohydrate, protein, amino acids, vitamins and/or minerals.

As used herein, the term "treatment", is defined as the application or administration of a therapeutic agent to a patient, or application or administration of a therapeutic agent to an isolated tissue or cell line from a patient, who has a disease or disorder, a symptom of a disease or disorder or a predisposition toward a disease or disorder, with the purpose of curing, healing, alleviating, relieving, altering, remedying, ameliorating, improving or affecting the disease or disorder, the symptoms of disease or disorder, or the predisposition toward a disease or disorder. A therapeutic agent includes, but is not limited to, small molecules, peptides, peptidomimetics, nucleic acid molecules, antibodies, ribozymes, RNA interfering agents, e.g., siRNA molecules, and sense and antisense oligonucleotides described herein.

As used herein, the term "administering a treatment to an animal or cell" is intended to refer to dispensing, delivering or applying a treatment to an animal or cell. In terms of the therapeutic agent, the term "administering" is intended to refer to contacting or dispensing, delivering or applying the therapeutic agent to an animal by any suitable route for delivery of the therapeutic agent to the desired location in the animal, including delivery by either the parenteral or oral route, intramuscular injection, subcutaneous/intradermal injection, intravenous injection, buccal administration, transdermal delivery and administration by the intranasal or respiratory tract route.

As used herein, the term "transgenic animal" refers to a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "misexpression" includes a non-wild type pattern of gene expression. Expression as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g. a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "RNA interfering agent" is defined as any agent which interferes with or inhibits expression of a target gene, e.g., a marker of the invention, by RNA interference (RNAi). Such RNA interfering agents include, but are not limited to, nucleic acid molecules including RNA molecules which are homologous to the target gene, e.g., a marker of the invention, or a fragment thereof, short interfering RNA (siRNA), and small molecules which interfere with or inhibit expression of a target gene by RNA interference (RNAi).

As used herein, the term "RNA interference (RNAi)" is an evolutionary conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

As used herein, the term "short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501 incorporated be reference herein).

As used herein, the term "constitutive" promoter is a nucleotide sequence which, when operably linked with a polynucleotide which encodes or specifies a gene product, causes the gene product to be produced in a living human cell under most or all physiological conditions of the cell.

As used herein, the term "inducible" promoter is a nucleotide sequence which, when operably linked with a polynucleotide which encodes or specifies a gene product, causes the gene product to be produced in a living human cell substantially only when an inducer which corresponds to the promoter is present in the cell.

As used herein, the term "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

Various aspects of the invention are described in further detail in the following subsections:

I. Screening Assays:

The invention provides a method (also referred to herein as a "screening assay") for identifying modulators, i.e., candidate or test compounds or agents (e.g., peptides, peptidomimetics, small molecules (organic or inorganic) or other drugs) which bind to PGC-1β proteins, have a stimulatory or inhibitory effect on, for example, PGC-1β expression or PGC-1β activity, or have a stimulatory or inhibitory effect on, for example, the expression or activity of a PGC-1β substrate. Compounds identified using assays described herein may be useful for modulating PGC-1β expression or activity, e.g., decreasing PGC-1β expression or activity. Thus, these compounds would be useful for treating or preventing lipid-related diseases or disorders.

These assays are designed to identify compounds that bind to or interact with a PGC-1β protein, or bind to or interact with other intracellular or extracellular proteins that interact with or modulate a PGC-1β protein. Such compounds may include, but are not limited to peptides, antibodies, nucleic acid molecules, siRNA molecules, or small organic or inorganic compounds. Such compounds may also include other cellular proteins.

Compounds identified via assays such as those described herein may be useful, for example, modulating PGC-1β, e.g., by causing a decrease in PGC-1β expression or activity. Those activities include, for example, modulation of lipid transport, modulation of lipid biosynthesis, modulation of plasma triglyceride levels, and modulation of plasma cholesterol levels. Thus, these compounds would be useful for treating or preventing a lipid-related disease or disorder. In instances whereby decreased PGC-1β activity or expression is desired, compounds that interact with the PGC-1β protein may include compounds which inhibit or suppress the expression or activity of PGC-1β protein. Such compounds would bring about an effective decrease in the level of PGC-1β protein activity, thus, treating or preventing lipid-related diseases or disorders. For example, a partial antagonist or an antagonist administered in a dosage or for a length of time to decrease expression or activity of PGC-1β would act to decrease lipid transport and/or lipid biosynthesis, thereby decreasing plasma triglyceride levels and/or plasma cholesterol levels in a subject. Alternatively, in instances whereby increased PGC-1β activity or expression is desired, e.g., to treat or prevent an obesity-related diseases or disorders, e.g., cachexia, wasting, anorexia, or bulimia. Compounds that interact with the PGC-1β protein may include compounds which accentuate or amplify the expression or activity of PGC-1β protein. Such compounds would bring about an effective increase in the level of PGC-1β protein activity, thus acting as an inducer of an obesity-related disease or disorder, depending on the dosage of the compound and the length of time the compound is administered.

In one embodiment, the invention provides assays for screening candidate or test compounds which are substrates of or interact with a PGC-1β protein or polypeptide or biologically active portion thereof. In another embodiment, the invention provides assays for screening candidate or test compounds which bind to or modulate the activity of a PGC-1β protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a PGC-1β protein or biologically active portion thereof is contacted with a test compound and the ability of the test compound to modulate PGC-1β activity is determined. Determining the ability of the test compound to modulate PGC-1β activity can be accomplished by monitoring, for example, intracellular calcium, $IP_3$, cAMP, or diacylglycerol concentration, or the phosphorylation profile of intracellular proteins, or the level of transcription of downstream genes. The cell can be of mammalian origin, e.g., a liver cell. In one embodiment, compounds that interact with PGC-1β binding site can be screened for their ability to function as ligands, i.e., to bind to PGC-1β binding site and modulate transcription or modulate a signal transduction pathway. Identification of PGC-1β ligands, and measuring the activity of the ligand-PGC-1β complex, leads to the identification of modulators (e.g., antagonists or agonists) of this interaction. Such modulators may be useful in the treatment and prevention of a lipid-related disease or disorder modulation of PGC-1β, e.g., by causing decreased expression or activity of PGC-1β.

The ability of the test compound to modulate PGC-1β binding to a substrate or to bind to PGC-1β can also be determined. Determining the ability of the test compound to modulate PGC-1β binding to a substrate can be accomplished, for example, by coupling the PGC-1β substrate with a radioisotope or enzymatic label such that binding of the PGC-1β substrate to PGC-1β can be determined by detecting the labeled PGC-1β substrate in a complex. PGC-1β could also be coupled with a radioisotope or enzymatic label to monitor the ability of a test compound to modulate PGC-1β binding to a PGC-1β substrate in a complex. Determining the ability of the test compound to bind PGC-1β can be accomplished, for example, by coupling the compound with a radioisotope or enzymatic label such that binding of the compound to PGC-1β can be determined by detecting the labeled PGC-1β compound in a complex. For example, compounds (e.g., PGC-1β ligands or substrates) can be labeled with $^{125}I$, $^{35}S$, $^{14}C$, or $^{3}H$, either directly or indirectly, and the radioisotope detected by direct counting of radioemmission or by scintillation counting. Compounds can further be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PGC-1β ligand or substrate) to interact with PGC-1β without the labeling of any of the interactants. For example, a microphysiometer can be used to detect the interaction of a compound with PGC-1β without the labeling of either the compound or the PGC-1β (McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PGC-1β.

In another embodiment, an assay is a cell-based assay comprising contacting a cell expressing a PGC-1β target molecule (e.g., a PGC-1β substrate) with a test compound and determining the ability of the test compound to modulate (e.g., stimulate or inhibit) the activity of the PGC-1β target molecule. Determining the ability of the test compound to modulate the activity of a PGC-1β target molecule can be accomplished, for example, by determining the ability of the PGC-1β protein to bind to or interact with the PGC-1β target molecule.

Determining the ability of the PGC-1β protein or a biologically active fragment thereof, to bind to or interact with a PGC-1β target molecule can be accomplished by one of the methods described above for determining direct binding. In a preferred embodiment, determining the ability of the PGC-1β protein to bind to or interact with a PGC-1β target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression).

In yet another embodiment, an assay of the present invention is a cell-free assay in which a PGC-1β protein or biologically active portion thereof, is contacted with a test compound and the ability of the test compound to bind to the PGC-1β protein or biologically active portion thereof is determined. Preferred biologically active portions of the PGC-1β proteins to be used in assays of the present invention include fragments which participate in interactions with non-PGC-1β molecules, e.g., fragments with high surface probability scores. Binding of the test compound to the PGC-1β protein can be determined either directly or indirectly as described above. In a preferred embodiment, the assay includes contacting the PGC-1β protein or biologically active portion thereof with a known compound which binds PGC-1β to form an assay mixture, contacting the assay mixture with a test compound, and determining the ability of the test compound to interact with a PGC-1β protein, wherein determining the ability of the test compound to interact with a PGC-1β protein comprises determining the ability of the test compound to preferentially bind to PGC-1β or biologically active portion thereof as compared to the known compound. Compounds that modulate the interaction of PGC-1β with a known target protein may be useful in regulating the activity of a PGC-1β protein, especially a mutant PGC-1β protein.

In another embodiment, the assay is a cell-free assay in which a PGC-1β protein or biologically active portion thereof is contacted with a test compound and the ability of the test compound to modulate (e.g., stimulate or inhibit) the activity of the PGC-1β protein or biologically active portion thereof is determined. Determining the ability of the test compound to modulate the activity of a PGC-1β protein can be accomplished, for example, by determining the ability of the PGC-1β protein to bind to a PGC-1β target molecule by one of the methods described above for determining direct binding. Determining the ability of the PGC-1β protein to bind to a PGC-1β target molecule can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Cur. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, determining the ability of the test compound to modulate the activity of a PGC-1β protein can be accomplished by determining the ability of the PGC-1β protein to further modulate the activity of a downstream effector of a PGC-1β target molecule. For example, the activity of the effector molecule on an appropriate target can be determined or the binding of the effector to an appropriate target can be determined as previously described.

In yet another embodiment, the cell-free assay involves contacting a PGC-1β protein or biologically active portion thereof with a known compound which binds the PGC-1β protein to form an assay mixture, contacting the assay mixture with a test compound, and determining the ability of the test compound to interact with the PGC-1β protein, wherein determining the ability of the test compound to interact with the PGC-1β protein comprises determining the ability of the PGC-1β protein to preferentially bind to or modulate the activity of a PGC-1β target molecule.

In other embodiments of the above assay methods of the present invention, it may be desirable to immobilize either PGC-1β or its target molecule to facilitate separation of complexed from uncomplexed forms of one or both of the proteins, as well as to accommodate automation of the assay. Binding of a test compound to a PGC-1β protein, or interaction of a PGC-1β protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PGC-1β fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PGC-1β protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PGC-1β binding or activity determined using standard techniques.

Other techniques for immobilizing proteins on matrices can also be used in the screening assays of the invention. For example, either a PGC-1β protein or a PGC-1β target molecule can be immobilized utilizing conjugation of biotin and streptavidin. Biotinylated PGC-1β protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1β protein or target molecules but which do not interfere with binding of the PGC-1β protein to its target molecule can be derivatized to the wells of the plate, and unbound target or PGC-1β protein trapped in the wells by antibody conjugation. Methods for detecting such complexes, in addition to those described above for the GST-immobilized complexes, include immunodetection of complexes using antibodies reactive with the PGC-1β protein or target molecule, as well as enzyme-linked assays which rely on detecting an enzymatic activity associated with the PGC-1β protein or target molecule.

In another embodiment, modulators of PGC-1β expression are identified in a method wherein a cell is contacted with a candidate compound and the expression of PGC-1β mRNA or protein in the cell is determined. The level of expression of PGC-1β mRNA or protein in the presence of the candidate compound is compared to the level of expression of PGC-1β mRNA or protein in the absence of the candidate compound. The candidate compound can then be identified as a modulator of PGC-1β expression based on this comparison. For example, when expression of PGC-1β mRNA or protein is greater (statistically significantly greater) in the presence of the candidate compound than in its absence, the candidate compound is identified as a stimulator of PGC-1β mRNA or protein expression. Alternatively, when expression of PGC-1β mRNA or protein is less (statistically significantly less) in the presence of the candidate compound than in its absence, the candidate compound is identified as an inhibitor of PGC-1β mRNA or protein expression. The level of PGC-1β mRNA or protein expression in the cells can be determined by methods described herein for detecting PGC-1β mRNA or protein.

In yet another aspect of the invention, the PGC-1β proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with PGC-1β ("PGC-1β-binding proteins" or "PGC-1β-bp") and are involved in PGC-1β activity. Such PGC-1β-binding proteins are also likely to be involved in the propagation of signals by the PGC-1β proteins or PGC-1β targets as, for example, downstream elements of a PGC-1β-mediated signaling pathway. Alternatively, such PGC-1β-binding proteins are likely to be PGC-1β inhibitors.

The two-hybrid system is based on the modular nature of most transcription factors, which consist of separable DNA-binding and activation domains. Briefly, the assay utilizes two different DNA constructs. In one construct, the gene that codes for a PGC-1β protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PGC-1β-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PGC-1β protein.

In a further embodiment, assays may be devised through the use of the invention for the purpose of identifying compounds which modulate (e.g., affect either positively or negatively) interactions between PGC-1β and its substrates and/or binding partners. Such compounds can include, but are not limited to, molecules such as small molecules, antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a transcriptional coactivator, PGC-1β identified herein, the known binding partner and/or substrate of same, and the test compound. Test compounds can be supplied from any source.

The basic principle of the assay systems used to identify compounds that interfere with the interaction between PGC-1β and its binding partner involves preparing a reaction mixture containing PGC-1β and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of PGC-1β and its binding partner. Control reaction mixtures are incubated without the test compound or with a placebo. The formation of any complexes between PGC-1β and its binding partner is then detected. The formation of a complex in the control reaction, but less or no such formation in the reaction mixture containing the test compound, indicates that the compound interferes with the interaction of PGC-1β and its binding partner. Conversely, the formation of more complex in the presence of compound than in the control reaction indicates that the compound may enhance interaction of PGC-1β and its binding partner.

The assay for compounds that interfere with the interaction of PGC-1β with its binding partner may be conducted in a heterogeneous or homogeneous format. Heterogeneous assays involve anchoring either PGC-1β or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between PGC-1β and the binding partners (e.g., by competition) can be identified by conducting the reaction in the presence of the test substance, i.e., by adding the test substance to the reaction mixture prior to or simultaneously with PGC-1β and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either PGC-1β or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of PGC-1β or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/PGC-1β fusion proteins or glutathione-S-transferase/binding partner can be adsorbed onto glutathione sepharose beads (Sigma Chemical™, St. Louis, Mo.) or glutathione derivatized microtiter plates, which are then combined with the test compound or the test compound and either the non-adsorbed PGC-1β or its binding partner, and the mixture incubated under conditions conducive to complex formation (e.g., physiological conditions). Following incubation, the beads or microtiter plate wells are washed to remove any unbound assay components; the immobilized complex assessed either directly or indirectly, for example, as described above. Alternatively, the complexes can be dissociated from the matrix, and the level of PGC-1β binding or activity determined using standard techniques.

Other techniques for immobilizing proteins on matrices can also be used in the screening assays of the invention. For example, either PGC-1β or PGC-1β binding partner can be immobilized utilizing conjugation of biotin and streptavidin. Biotinylated PGC-1β protein or target molecules can be prepared from biotin-NHS (N-hydroxy-succinimide) using techniques known in the art (e.g., biotinylation kit, Pierce Chemicals™, Rockford, Ill.), and immobilized in the wells of streptavidin-coated 96 well plates (Pierce Chemicals™). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format; for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J. Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between PGC-1β and its binding partner.

Also within the scope of the present invention are methods for direct detection of interactions between PGC-1β and its natural binding partner and/or a test compound in a homogeneous or heterogeneous assay system without further sample manipulation. For example, the technique of fluorescence energy transfer may be utilized (see, e.g. Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g. PGC-1β or test compound) such that its emitted fluorescent energy will be absorbed by a fluorescent label on a second, 'acceptor' molecule (e.g., PGC-1β or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between PGC-1β and its binding partner can be identified in controlled assays.

In another embodiment, modulators of PGC-1β expression are identified in a method wherein a cell is contacted with a candidate compound and the expression of mRNA or protein, corresponding to a PGC-1β in the cell, is determined. The level of expression of mRNA or protein in the presence of the candidate compound is compared to the level of expression of mRNA or protein in the absence of the candidate compound. The candidate compound can then be identified as a modulator of PGC-1β expression based on this comparison. For example, when expression of PGC-1β mRNA or protein is greater (statistically significantly greater) in the presence of the candidate compound than in its absence, the candidate compound is identified as a stimulator of PGC-1β mRNA or protein expression. Conversely, when expression of PGC-1β mRNA or protein is less (statistically significantly less) in the presence of the candidate compound than in its absence, the candidate compound is identified as an inhibitor of PGC-1β mRNA or protein expression. The level of PGC-1β mRNA or protein expression in the cells can be determined by methods described herein for detecting PGC-1β mRNA or protein.

In another aspect, the invention pertains to a combination of two or more of the assays described herein. For example, a modulating agent can be identified using a cell-based or a cell free assay, and the ability of the agent to modulate the activity of a PGC-1β protein can be confirmed in vivo, e.g., in an animal such as an animal model for a lipid-related disease or disorder, as described herein, or described in, for example, Sathasivam K et al. *Philos Trans R Soc Lond B Biol Sci.* 1999 Jun. 29; 354(1386):963-9; Bates G P, et al. *Hum Mol. Genet.* 1997; 6(10):1633-7; Shaw C A et al *Neurosci Biobehav Rev.* 2003 October; 27(6):493-505; Menalled L B *Trends Pharmacol Sci.* 2002 January; 23(1):32-9; Legare M E et al. *Genet Mol. Res.* 2003 Sep. 30; 2(3):288-94; Oiwa Y *J Neurosurg.* 2003 January; 98(1):136-44; and Bard F et al. *Nat. Med.* 2000 August; 6(8):916-9, the contents of which are incorporated by reference herein.

This invention further pertains to novel agents identified by the above-described screening assays. Accordingly, it is within the scope of this invention to further use an agent identified as described herein in an appropriate animal model. For example, an agent identified as described herein (e.g., a small molecule, an antisense PGC-1β nucleic acid molecule, a PGC-1β-specific antibody, or a PGC-1β-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for a compound capable of treating or preventing a lipid-related disease or disorder comprising the ability of the compound to modulate PGC-1β nucleic acid expression or PGC-1β polypeptide activity, thereby identifying a compound capable of treating or preventing a lipid-related disease or disorder. Cell-based and animal model-based assays for the identification of compounds exhibiting such an ability to treat or prevent a lipid-related disease or disorder described herein.

In one aspect, cell-based systems, as described herein, may be used to identify compounds which may act to modulate PGC-1β nucleic acid expression or PGC-1 polypeptide activity or treat lipid-related diseases or disorders. For example, such cell systems may be exposed to a compound, suspected of exhibiting an ability to modulate PGC-1β or treat or prevent a lipid-related disease or disorder, at a sufficient concentration and for a time sufficient to elicit such an amelioration of disease symptoms in the exposed cells. After exposure, the cells are examined to determine whether one or more of the disease phenotypes, e.g., hypertriglyceridemia, for example, has been altered to, resemble a more normal or more wild type disease phenotype.

In addition, animal-based disease systems, such as those described herein, may be used to identify compounds which may act to modulate PGC-1β nucleic acid expression or PGC-1β polypeptide activity or a lipid-related disease or disorder. Such animal models may be used as test substrates for the identification of drugs, pharmaceuticals, therapies, and interventions which may be effective in modulating PGC-1β, treating or preventing a lipid-related disease or disorder e.g., hypertriglyceridemia.

In one embodiment, compounds which are capable of treating or preventing a lipid-related disease or disorder are identified by assaying the ability of the compound to modulate PGC-1β nucleic acid expression or PGC-1β polypeptide activity. Compounds which are capable of modulating PGC-1β nucleic acid expression or PGC-1β polypeptide activity may be identified by detecting modulation in the expression or activity of lipogenic genes, e.g., FAS, SCD-1, HMG-CoA reductase, DGAT, or GPAT.

In still another embodiment, compounds which are capable of treating or preventing a lipid-related disease or disorder are identified by assaying the ability of the compound to modulate the expression or activity of LXRα target gene, e.g., PLTP, ABCA1 and ABCG1.

In yet another embodiment, compounds which are capable of treating or preventing a lipid-related disease or disorder are identified by assaying the ability of the compound to modulate the expression or activity of an SREBP transcription factor, e.g., SREBP1a, SREBP1c and SREBP2.

Additionally, gene expression patterns may be utilized to assess the ability of a compound to modulate PGC-1β e.g., by causing decreased PGC-1β expression or activity. Thus, these compounds would be useful for treating, preventing, or assessing a lipid-related disease or disorder. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Gene expression profiles may be generated, for example, by utilizing a differential display procedure, Northern analysis and/or RT-PCR.

In one embodiment, PGC-1β gene sequences may be used as probes and/or PCR primers for the generation and corroboration of such gene expression profiles.

Gene expression-profiles may be characterized for known states within the cell and/or animal-based model systems. Subsequently, these known gene expression profiles may be compared to ascertain the effect a test compound has to modify such gene expression profiles, and to cause the profile to more closely resemble that of a more desirable profile.

II. Methods of Treatment:

The present invention provides for both prophylactic and therapeutic methods of treating or preventing a lipid-related disease or disorder in a subject, e.g., a human, at risk of (or susceptible to) a lipid-related disease or disorder, by administering to said subject a PGC-113 modulator, such that the lipid-related disease or disorder is treated or prevented. In a preferred embodiment, which includes both prophylactic and therapeutic methods, the PGC-1β modulator is administered by in a pharmaceutically acceptable formulation.

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring a subject's prophylactic or therapeutic treatment with either the PGC-1β molecules of the present invention or PGC-1β modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for treating or preventing a lipid-related disease or disorder by administering to a subject an agent which modulates PGC-1β expression or PGC-1β activity. The invention also provides methods for modulating lipid transport, lipid biosynthesis, plasma triglyceride levels and plasma cholesterol levels in a subject. Subjects at risk for a lipid-related disease or disorder can be identified by, for example, any or a combination of the diagnostic or prognostic assays described herein. Administration of a prophylactic agent can occur prior to the manifestation of symptoms characteristic of a lipid-related disease or disorder, such that the lipid-related disease or disorder or symptom thereof, is prevented or, alternatively, delayed in its progression. Depending on the type of PGC-1β aberrancy, for example, a PGC-1β agonist or PGC-1β antagonist agent can be used for treating the subject. The appropriate agent can be determined based on screening assays described herein.

B. Therapeutic Methods

The present invention provides methods for modulating PGC-1β in a subject by administering a PGC-1β modulator to either induce or inhibit PGC-1β expression or activity. In one embodiment, PGC-1β expression or activity is decreased by administering an inhibitor or antagonist of PGC-1β expression or activity, thereby modulating lipid transport, lipid biosynthesis, plasma triglyceride levels and plasma cholesterol levels in a subject and treating or preventing a lipid-related disease or disorder.

Accordingly, another aspect of the invention pertains to methods of modulating PGC-1β expression or activity for therapeutic purposes and for use in treatment of a lipid-related disease or disorder. In one embodiment, the modulatory method of the invention involves contacting a cell with a PGC-1β or agent that modulates one or more of the activities of PGC-1β protein activity associated with a lipid-related disease or disorder (e.g., modulation of lipid biosynthesis, lipid transport, plasma triglyceride levels, plasma cholesterol levels). An agent that modulates PGC-1β protein activity can be an agent as described herein, such as a nucleic acid or a protein, an siRNA targeting PGC-1β mRNA, a naturally-occurring target molecule of a PGC-1β protein (e.g., a PGC-1β ligand or substrate), a PGC-1β antibody, a PGC-1β agonist or antagonist, a peptidomimetic of a PGC-1β agonist or antagonist, or other small molecule. In one embodiment, the agent stimulates one or more PGC-1β activities. Examples of such stimulatory agents include active PGC-1β protein, a nucleic acid molecule encoding PGC-1β, or a small molecule agonist, or mimetic, e.g., a peptidomimetic. In another embodiment, the agent inhibits one or more PGC-1β activities. Examples of such inhibitory agents include antisense PGC-1β nucleic acid molecules, siRNA molecules, anti-PGC-1β antibodies, small molecules, and PGC-1β inhibitors. These modulatory methods can be performed in vitro (e.g., by culturing the cell with the agent) or, alternatively, in vivo (e.g., by administering the agent to a subject). In one embodiment, the method involves administering an agent (e.g., an agent identified by a screening assay described herein), or combination of agents that modulates (e.g., upregulates or downregulates) PGC-1β expression or activity. In another embodiment, the method involves administering a PGC-1β protein or nucleic acid molecule as therapy to compensate for reduced, aberrant, or unwanted PGC-1β expression or activity.

A reduction of PGC-1β activity is desirable in situations in which a decrease in PGC-1β activity is likely to have a beneficial effect, e.g., for the treatment or prevention of a lipid-related disease or disorder. Likewise, a stimulation of PGC-1β activity is desirable in situations in which an increase in PGC-1β activity is likely to have a beneficial effect, e.g., to treat or prevent obesity-related diseases or disorders, e.g., cachexia, wasting, anorexia, or bulimia.

(i) Methods for Decreasing PGC-1β Expression or Activity

Decreasing PGC-1β expression or activity leads to treatment or prevention of a lipid-related disease or disorder, therefore providing a method for treating and/or preventing a lipid-related disease or disorder, e.g., hyperlipidemia, hypertriglyceridemia, hypercholesterolemia, cardiovascular disease, obesity, and type II diabetes. A variety of techniques may be used to decrease the expression, synthesis, or activity of PGC-1β.

For example, compounds such as those identified through assays described herein, which exhibit inhibitory activity, may be used in accordance with the invention. Such molecules may include, but are not limited to, small organic molecules, siRNA molecules, peptides, antibodies, and the like.

For example, compounds can be administered that compete with the endogenous ligand for the PGC-1β protein. The resulting reduction in the amount of ligand-bound PGC-1β protein will modulate endothelial cell physiology. Compounds that can be particularly useful for this purpose include, for example, soluble proteins or peptides, such as peptides comprising one or more of the extracellular domains, or portions and/or analogs thereof, of the PGC-1β protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the PGC-1β receptor site, but do not activate the protein, (e.g., receptor-ligand antagonists) can be effective in inhibiting PGC-1β protein activity.

Further, antisense and ribozyme molecules and siRNA molecules which inhibit expression of the PGC-1β gene may also be used in accordance with the invention to inhibit aberrant PGC-1β gene activity. Still further, triple helix molecules may be utilized in inhibiting aberrant PGC-1β gene activity.

The antisense nucleic acid molecules used in the methods of the invention are typically administered to a subject or generated in situ such that they hybridize with or bind to cellular mRNA and/or genomic DNA encoding a PGC-1β protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, an antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave PGC-1β mRNA transcripts thereby to inhibit translation of PGC-1β mRNA. A ribozyme having specificity for a PGC-1-encoding nucleic acid can be designed based upon the nucleotide sequence of a PGC-1β cDNA disclosed herein (i.e., SEQ ID NO: 1). For example, a derivative of a Tetrahymena L-19 IVS RNA can be constructed in which the nucleotide sequence of the active site is complementary to the nucleotide sequence to be cleaved in a PGC-1β-encoding mRNA (see, for example, Cech et al. U.S. Pat. No. 4,987,071; and Cech et al. U.S. Pat. No. 5,116,742). Alternatively, PGC-1β mRNA can be used to select a catalytic RNA having a specific ribonuclease activity from a pool of RNA molecules (see, for example, Bartel, D. and Szostak, J. W. (1993) *Science* 261:1411-1418).

PGC-1β gene expression can also be inhibited by targeting nucleotide sequences complementary to the regulatory region of the PGC-1β (e.g., the PGC-1β promoter and/or enhancers) to form triple helical structures that prevent transcription of the PGC-1β gene in target cells (see, for example, Helene, C. (1991) *Anticancer Drug Des.* 6(6):569-84; Helene, C. et al. (1992) *Ann. N.Y. Acad. Sci.* 660:27-36; and -Maher, L. J. (1992) *Bioassays* 14(12):807-15).

An RNA interfering agent, e.g., an siRNA molecule, which is targeted to PGC-1β, can also be used in order to inhibit expression of PGC-1β, e.g., through degradation or specific post-transcriptional gene silencing (PTGS) of the messenger RNA (mRNA) of PGC-1β.

Antibodies that are both specific for the PGC-1β protein and interfere with its activity may also be used to modulate or inhibit PGC-1β protein function. Such antibodies may be generated using standard techniques described herein, against the PGC-1β protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889-7893

(ii) Methods for Increasing PGC-1β Expression, Synthesis, or Activity

As discussed above, increasing PGC-1β expression or activity may be desirable in certain situations, e.g., to treat or prevent obesity-related diseases or disorders, e.g., cachexia, wasting, AHS-related weight loss, anorexia, and bulimia. A variety of techniques may be used to increase the expression, synthesis, or activity of PGC-1β genes and/or proteins. For example, a PGC-1β protein may be administered to a subject. Any of the techniques discussed below may be used for such administration. One of skill in the art will readily know how to determine the concentration of effective, non-toxic doses of the PGC-1β protein, utilizing techniques such as those described below.

Additionally, RNA sequences encoding a PGC-1β protein may be directly administered to a subject, at a concentration sufficient to produce a level of PGC-1β protein such that PGC-1β is modulated. Any of the techniques discussed below, which achieve intracellular administration of compounds, such as, for example, liposome administration, may be used for the administration of such RNA molecules. The RNA molecules may be produced, for example, by recombinant techniques such as those described herein. Other pharmaceutical compositions, medications, or therapeutics may be used in combination with the PGC-1β agonists described herein. Further, subjects may be treated by gene replacement therapy, resulting in permanent modulation of PGC-1β. One or more copies of a PGC-1β gene, or a portion thereof, that directs the production of a normal PGC-1β protein with PGC-1β function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of PGC-1β gene sequences into human cells. Furthermore, expression or activity of transcriptional activators which act upon PGC-1β may be increased to thereby increasing expression and activity of PGC-1β. Small molecules which induce PGC-1β expression or activity, either directly or indirectly may also be used. In one embodiment, a small molecule functions to disrupt a protein-protein interaction between PGC-1β and a target molecule or ligand, thereby modulating, e.g., increasing or decreasing the activity of PGC-1β.

Cells, preferably, autologous cells, containing PGC-1β expressing gene sequences may then be introduced or reintroduced into the subject. Such cell replacement techniques may be preferred, for example, when the gene product is a secreted, extracellular gene product.

C. Pharmaceutical Compositions

The methods of the invention involve administering to a subject an agent which modulates PGC-1β expression or activity (e.g., an agent identified by a screening assay described herein), or a combination of such agents. The agents which modulate PGC-1β activity can be administered to a subject using pharmaceutical compositions suitable for such administration. Such compositions typically comprise the agent (e.g., small molecules, nucleic acid molecule, protein, siRNA or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates PGC-1β activity (e.g., a fragment of a PGC-1β protein or an anti-PGC-1β antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate PGC-1β activity can also be prepared in the form of suppositories (e.g., with conventional suppository bases such as cocoa butter and other glycerides) or retention enemas for rectal delivery.

In one embodiment, the agents that modulate PGC-1β activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc., Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates PGC-1β activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such PGC-1β modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a small molecules, nucleic acid molecule, protein, siRNA or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable; and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a PGC-1β molecule, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated, e.g., the intended use of the agonist or antagonize.

The invention also encompasses RNA interfering agents, e.g., siRNA molecules which target PGC-1β. As defined herein, a therapeutically effective amount of an RNA interfering agent, e.g., siRNA, (i.e., an effective dosage) ranges from about 0.001 to 3,000 mg/kg body weight, preferably about 0.01 to 2500 mg/kg body weight, more preferably about 0.1 to 2000, about 0.1 to 1000 mg/kg body weight, 0.1 to 500 mg/kg body weight, 0.1 to 100 mg/kg body weight, 0.1 to 50 mg/kg body weight, 0.1 to 25 mg/kg body weight, and even more preferably about 1 to 10 mg/kg, 2 to 9 mg/kg, 3 to 8 mg/kg, 4 to 7 mg/kg, or 5 to 6 mg/kg body weight. Treatment of a subject with a therapeutically effective amount of an RNA interfering agent can include a single treatment or, preferably, can include a series of treatments. In a preferred example, a subject is treated with an RNA interfering agent in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or -homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiane platinum (II) DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PGC-1β protein and/or nucleic acid expression as well as PGC-1β activity, in the context of a biological sample (e.g., blood, serum, fluid, cells, e.g., hepatocytes, or tissue, e.g., liver tissue) to thereby determine whether an individual is afflicted with lipid-related disease or disorder lipid-related disease or disorder has a risk of developing a lipid-related disease or disorder. The invention also provides for prognostic (or predictive) assays for determining whether an individual is at risk of developing a lipid-related disease or disorder. For example, mutations in a PGC-1β gene can be assayed for in a biological sample. Such assays can be used for prognostic or predictive purpose to thereby phophylactically treat an individual prior to the onset of a lipid-related disease or disorder.

One particular embodiment includes a method for assessing whether a subject is afflicted with a lipid-related disease or disorder has a risk of developing a lipid-related disease or disorder comprising detecting the expression of the PGC-1β gene or the activity of PGC-1β in a cell or tissue sample of a subject, wherein an increase in the expression of the PGC-1β gene or an increase in the activity of PGC-1β indicates the presence of a lipid-related disease or disorder or the risk of developing a lipid-related disease or disorder in the subject. In this embodiment, subject samples tested are, for example, (e.g., blood, serum, fluid, cells, e.g., hepatocytes, or tissue, e.g., liver tissue)

Another aspect of the invention pertains to monitoring the influence of PGC-1β modulators on the expression or activity of PGC-1β in clinical trials.

These and other agents are described in further detail in the following sections.

A. Prognostic and Diagnostic Assays

To determine whether a subject is afflicted with a lipid-related disease or disorder or has a risk of developing a lipid-related disease or disorder, a biological sample may be obtained from a subject and the biological sample may be contacted with a compound or an agent capable of detecting a PGC-1β protein or nucleic acid (e.g., mRNA or genomic DNA) that encodes a PGC-1β protein, in the biological sample.

A preferred agent for detecting PGC-1βmRNA or genomic DNA is a labeled nucleic acid probe capable of hybridizing to PGC-1β mRNA or genomic DNA. The nucleic acid probe can be, for example, the PGC-1β nucleic acid set forth in SEQ ID NO: 1, or a portion thereof, such as an oligonucleotide of at least 15, 20, 25, 30, 25, 40, 45, 50, 100, 250 or 500 nucleotides in length and sufficient to specifically hybridize under stringent conditions to PGC-1β mRNA or genomic DNA. Other suitable probes for use in the diagnostic assays of the invention are described herein.

The term "biological sample" is intended to include tissues, cells, and biological fluids isolated from a subject, as well as tissues, cells, and fluids present within a subject, (e.g., blood, serum, fluid, cells, e.g., hepatocytes, or tissue, e.g., liver tissue). That is, the detection method of the invention can be used to detect PGC-1β mRNA, protein, or genomic DNA in a biological sample in vitro as well as in vivo. For example, in vitro techniques for detection of PGC-1β mRNA include Northern hybridizations and in situ hybridizations. In vitro techniques for detection of PGC-1β protein include enzyme linked immunosorbent assays (ELISAs), Western blots, immunoprecipitations and immunofluorescence. In vitro techniques for detection of PGC-1β genomic DNA include Southern hybridizations. Furthermore, in vivo techniques for detection of PGC-1β protein include introducing into a subject a labeled anti-PGC-1β antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting PGC-1β protein, mRNA, or genomic DNA, such that the presence of PGC-1β protein, mRNA or genomic DNA is detected in the biological sample, and comparing the presence of PGC-1β protein, mRNA or genomic DNA in the control sample with the presence of PGC-1β protein, mRNA or genomic DNA in the test sample.

Analysis of one or more PGC-1β polymorphic regions in a subject can be useful for predicting whether a subject has or is likely to develop a lipid-related disease or disorder. In preferred embodiments, the methods of the invention can be characterized as comprising detecting, in a sample of cells from the subject, the presence or absence of a specific allelic variant of one or more polymorphic regions of a PGC-1β gene. The allelic differences can be: (i) a difference in the identity of at least one nucleotide or (ii) a difference in the number of nucleotides, which difference can be a single nucleotide or several nucleotides. The invention also provides methods for detecting differences in an PGC-1β gene such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. In a preferred embodiment of the invention, several probes capable of hybridizing specifically to allelic variants are attached to a solid phase support, e.g., a "chip". Oligonucleotides can be bound to a solid support by a variety of processes, including lithography. For example, a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism in the 5' upstream regulatory element can be determined in a single hybridization experiment.

In other detection methods, it is necessary to first amplify at least a portion of a PGC-1β gene prior to identifying the allelic variant. Amplification can be performed, e.g., by PCR and/or LCR (see Wu and Wallace, (1989) *Genomics* 4:560), according to methods known in the art. In one embodiment, genomic DNA of a cell is exposed to two PCR primers and amplification for a number of cycles sufficient to produce the required-amount of amplified DNA. In preferred embodiments, the primers are located between 150 and 350 base pairs apart.

Alternative amplification methods include: self sustained sequence replication (Guatelli, J. C. et al., 1990, *Proc. Natl. Acad. Sci. USA* 87:1874-1878), transcriptional amplification system (Kwoh, D. Y. et al., 1989, *Proc. Natl. Acad. Sci. USA* 86:1173-1177), Q-Beta Replicase (Lizardi, P. M. et al., 1988, *Bio/Technology* 6:1197), and self-sustained sequence replication (Guatelli et al., (1989) *Proc. Nat. Acad. Sci.* 87:1874), and nucleic acid based sequence amplification (NABSA), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of a PGC-1β gene and detect allelic variants, e.g., mutations, by comparing the sequence of the sample sequence with the corresponding reference (control) sequence. Exemplary sequencing reactions include those based on techniques developed by Maxam and Gilbert (*Proc. Natl. Acad Sci USA* (1977) 74:560) or Sanger (Sanger et al. (1977) *Proc. Nat. Acad. Sci.* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of a PGC-1β gene in DNA from a subject can be shown by restriction enzyme analysis. For example, a specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of an PGC-1β allelic variant with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al. (1988) *Proc. Natl Acad Sci USA* 85:4397; Saleeba et al (1992) *Methods Enzymol.* 217:286-295. In a preferred embodiment, the control or sample nucleic acid is labeled for detection.

In another embodiment, an allelic variant can be identified by denaturing high-performance liquid chromatography (DHPLC) (Oefner and Underhill, (1995) *Am. J. Human Gen.* 57:Suppl. A266). DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57:Suppl. A266). In general, PCR products are produced using PCR primers flanking the DNA of interest. DHPLC analysis is carried out and the resulting chromatograms are analyzed to identify base pair alterations or deletions based on specific chromatographic profiles (see O'Donovan et al. (1998) *Genomics* 52:44-49).

In other embodiments, alterations in electrophoretic mobility is used to identify the type of PGC-1β allelic variant. For example, single strand conformation polymorphism (SSCP) may be used to detect differences in electrophoretic mobility between mutant and wild type nucleic acids (Orita et al. (1989) *Proc Natl. Acad. Sci. USA* 86:2766; see also Cotton (1993) *Mutat Res* 285:125-144; and Hayashi (1992) *Genet Anal Tech Appl* 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265: 1275).

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163), Saiki et al (1989) *Proc. Natl cad. Sci USA* 86:6230; and Wallace et al. (1979) *Nucl. Acids Res.* 6:3543). Such allele specific oligonucleotide hybridization techniques may be used for the simultaneous detection of several nucleotide changes in different polymorphic regions of PGC-1β. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238; Newton et al. (1989) *Nucl. Acids Res.* 17:2503). This technique is also termed "PROBE" for Probe Oligo Base Extension. In addition, it may be desirable to introduce a novel restriction site in the region of the mutation to create cleavage-based detection (Gasparini et al. (1992) *Mol. Cell. Probes* 6:1).

In another embodiment, identification of the allelic variant is carried out using an oligonucleotide ligation assay (OLA), as described, e.g., in U.S. Pat. No. 4,998,617 and in Landegren, U. et al., (1988) *Science* 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., (1990) *Proc. Natl. Acad. Sci.* (U.S.A.) 87:8923-8927. In this method, PCR is used to achieve the exponential amplification of target DNA, which is then detected using OLA.

Several techniques based on this OLA method have been developed and can be used to detect specific allelic variants of a polymorphic region of an PGC-1β gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res* 24: 3728), OLA combined with PCR permits typing of two alleles in a single microtiter well. By marking each of the allele-specific primers with a unique hapten, i.e. digoxigenin and fluorescein, each OLA reaction can be detected by using, hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in a PGC-1β gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each subject. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide presents in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site (Cohen, D. et al. (French Patent 2,650, 840; PCT Application No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Application No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/ 02087) the method of Goelet, P. et al. is preferably a heterogeneous phase assay, in which the primer or the target molecule is immobilized to a solid phase.

Several primer-guided nucleotide incorporation procedures for assaying polymorphic sites in DNA have been described (Komher, J. S. et al, *Nucl. Acids. Res.* 17:7779-7784 (1989); Sokolov, B. P., *Nucl. Acids Res.* 18:3671 (1990); Syvanen, A.-C., et al., *Genomics* 8:684-692 (1990); Kuppuswamy, M. N. et al., *Proc. Natl. Acad. Sci.* (U.S.A.) 88:1143-1147 (1991); Prezant, T. R. et al., *Hum. Mutat.* 1:159-164 (1992); Ugozzoli, L. et al., *GATA* 9:107-112 (1992); Nyren, P. et al., *Anal. Biochem.* 208:171-175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., *Amer. J. Hum. Genet.* 52:46-59 (1993)).

For determining the identity of the allelic variant of a polymorphic region located in the coding region of a PGC-1β gene, yet other methods than those described above can be used. For example, identification of an allelic variant which encodes a mutated PGC-1β protein can be performed by using an antibody specifically recognizing the mutant protein in, e.g., immunohistochemistry or immunoprecipitation. Antibodies to wild-type PGC-1β or mutated forms of PGC-1β proteins can be prepared according to methods known in the art.

Alternatively, one can also measure an activity of a PGC-1β protein, such as binding to a PGC-1β ligand. Binding assays are known in the art and involve, e.g., obtaining cells from a subject, and performing binding experiments with a labeled lipid, to determine whether binding to the mutated form of the protein differs from binding to the wild-type of the protein.

Antibodies directed against reference or mutant PGC-1β polypeptides or allelic variant thereof, which are discussed above, may also be used in disease diagnostics and prognostics. Such diagnostic methods, may be used to detect abnormalities in the level of PGC-1β polypeptide expression, or abnormalities in the structure and/or tissue, cellular, or subcellular location of an PGC-1β polypeptide. Structural differences may include, for example, differences in the size, electronegativity, or antigenicity of the mutant PGC-1β polypeptide relative to the normal PGC-1β polypeptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al, 1989, supra, at Chapter 18. The protein detection and isolation methods employed herein may also be such as those described in Harlow and Lane, for example (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of PGC-1β polypeptides. In situ detection may be accomplished by removing a histological specimen from a subject, and applying thereto a labeled antibody of the present invention. The antibody (or fragment) is preferably applied by overlaying the labeled antibody (or fragment) onto a biological sample. Through the use of such a procedure, it is possible to determine not only the presence of the PGC-1β polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-PGC-1β polypeptide specific antibody is via linkage to an enzyme and use in an enzyme immunoassay (EIA) (Voller, "The Enzyme Linked Immunosorbent Assay (ELISA)", *Diagnostic Horizons* 2:1-7, 1978, Microbiological Associates Quarterly Publication, Walkersville, Md.; Voller, et al., *J. Clin. Pathol.* 31:507-520 (1978); Butler, *Meth. Enzymol.* 73:482-523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and acquorin.

If a polymorphic region is located in an exon, either in a coding or non-coding portion of the gene, the identity of the allelic variant can be determined by determining the molecular structure of the mRNA, pre-mRNA, or cDNA. The molecular structure can be determined using any of the above described methods for determining the molecular structure of the genomic DNA.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific PGC-1β allelic variant.

Sample nucleic acid to be analyzed by any of the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of subject tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

B. Diagnostic Assays for Classifying Fatty Acids

PGC-1β may be used to identify and classify dietary constituents in order to predict the effect of these constituents on blood lipid profiles in a subject. Accordingly, the present invention provides methods of classifying dietary constituents and atherogenic fatty acids by contacting a cell, e.g., a hepatocyte with a sample containing dietary constituents or fatty acids and measuring modulation of PGC-1β expression or activity. In another aspect, a dietary constituent or fatty acid to may be administered to a subject, e.g., a mammal, and modulation of PGC-1β, expression or activity measured.

An increase in PGC-1β expression or activity indicates the presence of a fatty acid, e.g., a trans fat or a saturated fat, which has a high atherogenic potential. Dietary constituents having a high atherogenic potential may cause an increase in lipid biosynthesis, lipid transport, triglyceride levels, and/or plasma cholesterol levels in a subject and also may lead to the development of a lipid-related disease or disorder in a subject. Methods for measuring modulation of PGC-1β expression or activity are described above. In one embodiment, a control sample which does not contain an atherogenic fatty acid or other compound which increases the expression or activity of PGC-1β is utilized.

C. Monitoring of Effects During Clinical Trials

The present invention further provides methods for determining the effectiveness of a PGC-1β modulator (e.g., a PGC-1β modulator identified herein) in treating or preventing a lipid-related disease or disorder or assessing risk of developing a lipid-related disease or disorder in a subject. For example, the effectiveness of a PGC-1β modulator in increasing or decreasing PGC-1β gene expression, protein levels, or in upregulating or down-regulating PGC-1β activity, can be monitored in clinical trials of subjects exhibiting increased or decreased PGC-1β gene expression, protein levels, or upregulated or downregulated PGC-1β activity. In such clinical trials, the expression or activity of a PGC-1β gene, and preferably, other genes that have been implicated in, for example, a PGC-1β pathway can be used as a "read out" or marker of the phenotype of a particular cell.

For example, and not by way of limitation, genes, including PGC-1β, that are modulated in cells by treatment with an agent which modulates PGC-1β activity (e.g., identified in a screening assay as described herein) can be identified. Thus, to study the effect of agents which modulate PGC-1β activity on subjects suffering a lipid-related disease or disorder, or agents to be used as a prophylactic, for example, a clinical trial, cells can be isolated and RNA prepared and analyzed for the levels of expression of PGC-1β and other genes implicated in PGC-1β activity or expression. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of PGC-1β or other genes. In this way, the gene expression pattern can serve as a marker, indicative of the physiological response of the cells to the agent which modulates PGC-1β activity. This response state may be determined before, and at various points during treatment of the individual with the agent which modulates PGC-1β activity.

In a preferred embodiment, the present invention provides a method for monitoring the effectiveness of treatment of a subject with an agent which modulates PGC-1β activity (e.g., an agonist, antagonist, peptidomimetic, protein, peptide, nucleic acid, siRNA, antibody or small molecule identified by the screening assays described herein) including the steps of (i) obtaining a pre-administration sample from a subject prior to administration of the agent; (ii) detecting the level of expression of a PGC-1β protein, mRNA, or genomic DNA in the pre-administration sample; (iii) obtaining one or more post-administration samples from the subject; (iv) detecting the level of expression or activity of the PGC-1β protein, mRNA, or genomic DNA in the post-administration samples; (v) comparing the level of expression or activity of the PGC-1β protein, mRNA, or genomic DNA in the pre-administration sample with the PGC-1β protein, mRNA, or genomic DNA in the post administration sample or samples; and (vi) altering the administration of the agent to the subject accordingly. For example, increased administration of the agent may be desirable to increase or decrease the expression or activity of PGC-1β to higher levels than detected, i.e., to increase the effectiveness of the agent. According to such an embodiment, PGC-1β expression or activity may be used as an indicator of the effectiveness of an agent, even in the absence of an observable phenotypic response.

IV. Recombinant Expression Vectors and Host Cells Used in the Methods of the Invention The methods of the invention (e.g., the screening assays and therapeutic and/or preventative methods described herein) include the use of vectors, preferably expression vectors, containing a nucleic acid encoding a PGC-1β protein (or a portion thereof). For example, in one embodiment, a vector containing a nucleic acid encoding a PGC-1β protein, or portion thereof, is used to deliver a PGC-1β protein, or portion thereof, to a subject, to treat or prevent a lipid-related disease or disorder in the subject. In one embodiment, the vector containing a nucleic acid encoding a PGC-1β protein, or portion thereof, is targeted to a specific cell type, organ or tissue, e.g., a hepatocyte as described herein.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g. tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PGC-1β proteins, mutant forms of PGC-1β proteins, fusion proteins, and the like).

The recombinant expression vectors to be used in the methods of the invention can be designed for expression of PGC-1β proteins in prokaryotic or eukaryotic cells. For example, PGC-1β proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion-protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PGC-1β activity assays, (e.g., direct assays or competitive assays described in detail below), or to generate antibodies specific for PGC-1β proteins. In a preferred embodiment, a PGC-1β fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include liver-specific promoters (e.g., the human phenylalanine hydroxylase (hPAH) gene promoter; Mancicni and Roy, (1996) Proc. Natl. Acad. Sci. USA. 93, 728-733); neuron-specific promoters (e.g., the neurofilament promoter; Byrne and Ruddle, 1989, *Proc. Natl. Acad. Sci. USA* 86:5473-5477), albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, EMBO J. 8:729-733) and immunoglobulins (Baneiji et al., 1983, Cell 33:729-740; Queen and Baltimore, 1983, Cell 33:741-748), pancreas-specific promoters (Edlund et al. 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1β mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagenud, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a PGC-1β nucleic acid molecule of the invention is introduced, e.g., a PGC-1β nucleic acid molecule within a recombinant expression vector or a PGC-1β nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PGC-1β protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sanbrook et al. (*Molecular Cloning. A Laboratory Manual. 2nd, ed., Cold Spring Harbor Laboratory*, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a PGC-1β protein. Accordingly, the invention further provides methods for producing a PGC-1β protein using the host cells of the invention. In one embodiment, the method comprises culturing the host cell of the invention (into which a recombinant expression vector encoding a PGC-1β protein has been introduced) in a suitable medium such that a PGC-1β protein is produced. In another embodiment, the method further comprises isolating a PGC-1β protein from the medium or the host cell.

The host cells of the invention can also be used to produce nonhuman transgenic animals. For example, in one embodiment, a host cell of the invention is a fertilized oocyte or an embryonic stem cell into which sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of PGC-1β, for identifying and/or evaluating modulators of PGC-1β polypeptide activity, as well as in pre-clinical testing of therapeutics or diagnostic molecules, for marker discovery or evaluation, e.g., therapeutic and diagnostic marker discovery or evaluation, or as surrogates of drug efficacy and specificity.

A transgenic animal of the invention can be created by introducing a nucleic acid encoding a polypeptide corresponding to PGC-1β into the male pronuclei of a fertilized oocyte, e.g. by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage PI. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

V. Isolated Nucleic Acid Molecules Used in the Methods of the Invention

The nucleotide sequence of the isolated human PGC-1β cDNA and the predicted amino acid sequence of the human PGC-1β polypeptide are shown in SEQ ID NOs:1 and 2, respectively. The nucleotide and amino acid sequences of human PGC-1β are also described in GenBank Accession No. GI: 31543391.

The methods of the invention include the use of isolated nucleic acid molecules that encode PGC-1β proteins or biologically active portions thereof, as well as nucleic acid fragments sufficient for use as hybridization probes to identify PGC-1β-encoding nucleic acid molecules (e.g., PGC-1β mRNA) and fragments for use as PCR primers for the amplification or mutation of PGC-1β nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:1, or a portion thereof, can be isolated using standard molecular biology techniques and the sequence information provided herein. Using all or portion of the nucleic acid sequence of SEQ ID NO:1 as a hybridization probe, PGC-1β nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to PGC-1β nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1, a complement of the nucleotide sequence shown in SEQ ID NO:1, or a portion of any of these nucleotide sequences. A nucleic acid molecule which is complementary to the nucleotide sequence shown in SEQ ID NO:1, is one which is sufficiently complementary to the nucleotide sequence shown in SEQ ID NO:1 such that it can hybridize to the nucleotide sequence shown in SEQ ID NO:1 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:1 or a portion of any of this nucleotide sequence.

Moreover, the nucleic acid molecules used in the methods of the invention can comprise only a portion of the nucleic acid sequence of SEQ ID NO:1, for example, a fragment which can be used as a probe or primer or a fragment encoding a portion of a PGC-113 protein, e.g., a biologically active portion of a PGC-1β protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 of an anti-sense sequence of SEQ ID NO:1 or of a naturally occurring allelic variant or mutant of SEQ ID NO:1. In one embodiment, a nucleic acid molecule used in the methods of the present invention comprises a nucleotide sequence which is greater than 100, 100-200, 200-300, 300-400, 400-500, 500-600, 600-700, 700-800, 800-900, 900-1000, 1000-1100, 1100-1200, 1200-1300, or more nucleotides in length and hybridizes under stringent hybridization conditions to a nucleic acid molecule of SEQ ID NO:1.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.1 SM NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% G+C)-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PGC-1β protein, such as by measuring a level of a PGC-1β-encoding nucleic acid in a sample of cells from a subject e.g., detecting PGC-1β mRNA levels or determining whether a genomic PGC-1β gene has been mutated or deleted.

The methods of the invention further encompass the use of nucleic acid molecules that differ from the nucleotide sequence shown in SEQ ID NO:1 due to degeneracy of the genetic code and thus encode the same PGC-1β proteins as those encoded by the nucleotide sequence shown in SEQ ID NO:1. In another embodiment, an isolated nucleic acid molecule included in the methods of the invention has a nucleotide sequence encoding a protein having an amino acid sequence shown in SEQ ID NO:2.

The methods of the invention further include the use of allelic variants of human PGC-1β, e.g., functional and non-functional allelic variants. Functional allelic variants are naturally occurring amino acid sequence variants of the human PGC-1β protein that maintain a PGC-1β activity. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the human PGC-1β protein that do not have a PGC-1β activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

The methods of the present invention may further use non-human orthologues of the human PGC-1β protein. Orthologues of the human PGC-1β protein are proteins that are isolated from non-human organisms and possess the same PGC-1β activity.

The methods of the present invention further include the use of nucleic acid molecules comprising the nucleotide sequence of SEQ ID NO:1 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of PGC-1β (e.g., the sequence of SEQ ID NO:2) without altering the biological activity, whereas an "essential" amino acid residue is required for biological activity. For example, amino acid residues that are conserved among the PGC-1β proteins of the present invention and other members of the PGC-1 family are not likely to be amenable to alteration.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid-residues. A "conservative amino acid substitution" is one in which the amino acid residue is replaced with an amino acid residue having a similar side chain. Families of amino acid residues having-similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chain (e.g., threonine, valine, isoleucine) and aromatic side chains (e.g., tyrosine, phenylalanine, tryptophan, histidine). Thus, a predicted nonessential amino acid residue in a PGC-1β protein is preferably replaced with another amino acid residue from the same side chain family. Alternatively, in another embodiment, mutations can be introduced randomly along all or part of a PGC-1β coding sequence, such as by saturation mutagenesis, and the resultant mutants can be screened for PGC-1β biological activity to identify mutants that retain activity. Following mutagenesis of SEQ ID NO:1 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:1. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1β coding strand, or to only a portion thereof. In one embodiment, an antisense nucleic acid molecule is antisense to a "coding region" of the coding strand of a nucleotide sequence encoding a PGC-1β. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PGC-1β. The term "noncoding region" refers to 5' and 3' sequences which flank the coding region that are not translated into amino acids (also referred to as 5' and 3' untranslated regions).

Given the coding strand sequences encoding PGC-1β disclosed herein, antisense nucleic acids of the invention can be designed according to the rules of Watson and Crick base pairing. The antisense nucleic acid molecule can be complementary to the entire coding region of PGC-1β mRNA, but more preferably is an oligonucleotide which is antisense to only a portion of the coding or noncoding region of PGC-1β mRNA. For example, the antisense oligonucleotide can be complementary to the region surrounding the translation start site of PGC-1β mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules used in the methods of the invention are further described above, in section IV.

In yet another embodiment, the PGC-1β nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670-675.

PNAs of PGC-1β nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of PGC-1β nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of PGC-1β can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PGC-1β nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3'PNA segment (Peterser, K. H. et al. (1975) *Bioorganic Med. Chem. Lett.* 5: 1119-11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556, Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

VI. Isolated PGC-1β Proteins and Anti-PGC-1β Antibodies Used in the Methods of the Invention The methods of the invention include the use of isolated PGC-1β proteins, and biologically active portions thereof, as well as polypeptide fragments suitable for use as immunogens to raise anti-PGC-1β antibodies. In one embodiment, native PGC-1β proteins can be isolated from cells or tissue sources by an appropriate purification scheme using standard protein purification techniques. In another embodiment, PGC-1β proteins are produced by recombinant DNA techniques. Alternative to recombinant expression, a PGC-1β protein or polypeptide can be synthesized chemically using standard peptide synthesis techniques.

As used herein, a "biologically active portion" of a PGC-1β protein includes a fragment of a PGC-1β protein having a PGC-1β activity. Biologically active portions of a PGC-1β protein include peptides comprising amino acid sequences sufficiently identical to or derived from the amino acid sequence of the PGC-1β protein, e.g., the amino acid sequence shown in SEQ ID NO:2, which include fewer amino acids than the full length PGC-1β proteins, and exhibit at least one activity of a PGC-1β protein. Typically, biologically active portions comprise a domain or motif with at least one activity of the PGC-1β protein (e.g., the N-terminal region of the PGC-1β protein that is believed to be involved in the regulation of apoptotic activity). A biologically active portion of a PGC-1β protein can be a polypeptide which is, for example, 25, 50, 75, 100, 125, 150, 175, 200, 250, 300 or more amino acids in length. Biologically active portions of a PGC-1β protein can be used as targets for developing agents which modulate a PGC-1β activity.

In a preferred embodiment, the PGC-1β protein used in the methods of the invention has an amino acid sequence shown in SEQ ID NO:2. In other embodiments, the PGC-1β protein is substantially identical to SEQ ID NO:2, and retains the functional activity of the protein of SEQ ID NO:2, yet differs in amino acid sequence due to natural allelic variation of mutagenesis, as described in detail in subsection V above. Accordingly, in another embodiment, the PGC-1β protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PGC-1β amino acid sequence of SEQ ID NO:2 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at the Genetics Computer Group website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the Genetics Computer Group website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11-17 (1988)) which has been incorporated into the ALIGN program (version 2.0 or 2.0 U), using a PAM120 weight residue table, a gap length penalty of 12 and a gap penalty of 4.

The methods of the invention may also use PGC-1β chimeric or fusion proteins. As used herein, a PGC-1β "chimeric protein" or "fusion protein" comprises a PGC-10 polypeptide operatively linked to a non-PGC-1β polypeptide. An "PGC-1β polypeptide" refers to a polypeptide having an amino acid sequence corresponding to a PGC-1β molecule, whereas a "non-PGC-1β polypeptide" refers to a polypeptide having an amino acid sequence corresponding to a protein which is not substantially homologous to the PGC-1β protein, e.g., a protein which is different from the PGC-1β, protein and which is derived from the same or a different organism. Within a PGC-1β fusion protein the PGC-1β polypeptide can correspond to all or a portion of a PGC-1β protein. In a preferred embodiment, a PGC-1β fusion protein comprises at least one biologically active portion of a PGC-1β protein. In another preferred embodiment, a PGC-1β fusion protein comprises at least two biologically active portions of a PGC-1β protein. Within the fusion protein, the term "operatively linked" is intended to indicate that the PGC-1β polypeptide and the non-PGC-1β polypeptide are fused in-frame to each other. The non-PGC-1β polypeptide can be fused to the N-terminus or C-terminus of the PGC-1β polypeptide.

For example, in one embodiment, the fusion protein is a GST-PGC-1β fusion protein in which the PGC-1β sequences are fused to the C-terminus of the GST sequences. Such fusion proteins can facilitate the purification of recombinant PGC-1β.

In another embodiment, this fusion protein is a PGC-1β protein containing a heterologous signal sequence at its N-terminus. In certain host cells (e.g., mammalian host cells), expression and/or secretion of PGC-1β can be decreased through use of a heterologous signal sequence.

The PGC-1β fusion proteins used in the methods of the invention can be incorporated into pharmaceutical compositions and administered to a subject in vivo. The PGC-1β fusion proteins can be used to affect the bioavailability of a PGC-1β substrate. Use of PGC-1β fusion proteins may be useful therapeutically for the treatment of disorders caused by, for example, (i) aberrant modification or mutation of a gene encoding a PGC-1β protein; (ii) mis-regulation of the PGC-1β gene; and (iii) aberrant post-translational modification of a PGC-1β protein.

Moreover, the PGC-1β-fusion proteins used in the methods of the invention can be used as immunogens to produce anti-PGC-1ββ antibodies in a subject, to purify PGC-1β ligands and in screening assays to identify molecules which inhibit the interaction of PGC-1β, with a PGC-1β substrate.

Preferably, a PGC-1β chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PGC-1β-encoding nucleic acid can be cloned into such an expression vector such that the fusion moiety is linked in-frame to the PGC-1β protein.

The present invention also pertains to the use of variants of the PGC-1β proteins which function as either PGC-1β agonists (mimetics) or as PGC-1β antagonists. Variants of the PGC-1β proteins can be generated by mutagenesis, e.g., discrete point mutation or truncation of a PGC-1β protein. An agonist of the PGC-1β proteins can retain substantially the same, or a subset, of the biological activities of the naturally occurring form of a PGC-1β protein. An antagonist of a PGC-1β protein can inhibit one or more of the activities of the naturally occurring form of the PGC-1β protein by, for example, competitively modulating a PGC-1β-mediated activity of a PGC-1β protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PGC-1β protein.

In one embodiment, variants of a PGC-1β protein which function as either PGC-1β agonists (mimetics) or as PGC-1β antagonists can be identified by screening combinatorial libraries of mutants, e.g., truncation mutants, of a PGC-1β protein for PGC-1β protein agonist or antagonist activity. In one embodiment, a variegated library of PGC-1β variants is generated by combinatorial mutagenesis at the nucleic acid level and is encoded by a variegated gene library. A variegated library of PGC-1β variants can be produced by, for example, enzymatically ligating a mixture of synthetic oligonucleotides into gene sequences such that a degenerate set of potential PGC-1β sequences is expressible as individual polypeptides, or alternatively, as a set of larger fusion proteins (e.g., for phage display) containing the set of PGC-1β sequences therein. There are a variety of methods which can be used to produce libraries of potential PGC-1β variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1β sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a PGC-1β protein coding sequence can be used to generate a variegated population of PGC-1β fragments for screening and subsequent selection of variants of a PGC-1β protein. In one embodiment, a library of coding sequence fragments can be generated by treating a double stranded PCR fragment of a PGC-1β coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1β protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1β proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1β variants (Arkin and Yourvan (1992) *Proc. Natl. Acad. Sci. USA* 89:7811-7815; Delgrave et al. (1993) *Protein Engineering* 6(3):327-331).

The methods of the present invention further include the use of anti-PGC-1β antibodies. An isolated PGC-1β protein, or a portion or fragment thereof, can be used as an immunogen to generate antibodies that bind PGC-1β using standard techniques for polyclonal and monoclonal antibody preparation. A full-length PGC-1β protein can be used or, alternatively, antigenic peptide fragments of PGC-1β can be used as immunogens. The antigenic peptide of PGC-1β comprises at least 8 amino acid residues of the amino acid sequence shown in SEQ ID NO:2 and encompasses an epitope of PGC-1β such that an antibody raised against the peptide forms a specific immune complex with the PGC-1β protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PGC-1β that are located on the surface of the protein, e.g., hydrophilic regions, as well as regions with high antigenicity.

A PGC-1β immunogen is typically used to prepare antibodies by immunizing a suitable subject, (e.g., rabbit, goat, mouse, or other mammal) with the immunogen. An appropriate immunogenic preparation can contain, for example, recombinantly expressed PGC-1β protein or a chemically synthesized PGC-1β polypeptide. The preparation can further include an adjuvant, such as Freund's complete or incomplete adjuvant, or similar immunostimulatory agent. Immunization of a suitable subject with an immunogenic PGC-1β preparation induces a polyclonal anti-PGC-1β antibody response.

The term "antibody" as used herein refers to immuoglobulin molecules and immunologically active portions of immunoglobulin molecules, i.e., molecules that contain an antigen binding site which specifically binds (immunoreacts with) an antigen, such as a PGC-1β. Examples of immunologically active portions of immunoglobulin molecules include F(ab) and F(ab')₂ fragments which can be generated by treating the antibody with an enzyme such as pepsin. The invention provides polyclonal and monoclonal antibodies that bind PGC-1β molecules. The term "monoclonal antibody" or "monoclonal antibody composition", as used herein, refers to a population of antibody molecules that contain only one species of an antigen binding site capable of immunoreacting with a particular epitope of PGC-1β. A monoclonal antibody composition thus typically displays a single binding affinity for a particular PGC-1β protein with which it immunoreacts.

Polyclonal anti-PGC-1β antibodies can be prepared as described above by immunizing a suitable subject with a PGC-1β immunogen. The anti-PGC-1β antibody titer in the immunized subject can be monitored over time by standard techniques, such as with an enzyme linked immunosorbent assay (ELISA) using immobilized PGC-1β. If desired, the antibody molecules directed against PGC-1β can be isolated from the mammal (e.g., from the blood) and further purified by well known techniques, such as protein A chromatography to obtain the IgG fraction. At an appropriate time after immunization, e.g., when the anti-PGC-1β antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with a PGC-1β immunogen as described above, and the culture supernatants of the resulting hybridoma cells are screened to identify a hybridoma producing a monoclonal antibody that binds PGC-1β.

Any of the many well known protocols used for fusing lymphocytes and immortalized cell lines can be applied for the purpose of generating an anti-PGC-1β monoclonal antibody (see, e.g., G. Galre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1β, e.g., using a standard ELISA assay.

Alternative to preparing monoclonal antibody-secreting hybridomas, a monoclonal anti-PGC-1β antibody can be identified and isolated by screening a recombinant combinatorial immunoglobulin library (e.g., an antibody phage display library) with PGC-1β to thereby isolate immunoglobulin library members that bind PGC-1β. Kits for generating and screening phage display libraries are commercially available (e.g., the Pharmacia Recombinant Phage Antibody System, Catalog No. 27-9400-01; and the Stratagene SurfZP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT international Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Puiblication No. WO 90/02809; Fuchs et al (1991) Bio/Technology 9:1370-1372; Hay et al. (1992) *Hum. Antibod. Hybridomas* 3:81-85; Huse et al: (1989) *Science* 246: 1275-1281; Griffiths et al. (1993) *EMBO J.* 12:725-734; Hawkins et al. (1992) *J. Mol. Biol.* 226:889-896; Clarkson et al (1991) *Nature* 352:624-628; Gram et al (1992) *Proc. Natl. Acad. Sci. USA* 89:3576-3580; Garrad et al (1991) *Bio/Technology* 9:1373-1377; Hoogenboom et al (1991) *Nuc. Acid Res.* 19:4133-4137; Barbas et al. (1991) *Proc. Natl. Acad. Sci. USA* 88:7978-7982; and McCafferty et at (1990) *Nature* 348: 552-554.

Additionally, recombinant anti-PGC-1β antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559; Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PGC-1β antibody can be used to detect PGC-1β protein (e.g., in a cellular lysate or cell supernatant) in order to evaluate the abundance and pattern of expression of the PGC-1β protein. Anti-PGC-1β antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include -streptavidin/biotin and avidin/biotin; examples of suitable fluorescent materials include umbelliferone, fluorescein, fluorescein isothiodyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}I$, $^{131}I$, $^{35}S$ or $^{3}H$.

This invention is further illustrated by the following Exemplification which should not be construed as limiting. The contents of all references, sequences, Figures, GenBank Accession Numbers, and published patent applications cited throughout this application are hereby incorporated by reference.

EXAMPLES

Materials and Methods

The following materials and methods were used for the experiments described below.

High-Fat Feeding and Array Analysis

Animals were fed a standard rodent chow and housed in a controlled environment with twelve-hour light and dark cycles. For high-fat feeding, three-month old male C57/B16J mice were switched to a diet containing 58% fat-derived calorie (D12331, Research Diets™) for 24 or 48 hours. For high-cholesterol feeding, two groups of mice were fed a base diet supplemented with either 0.07% or 2% cholesterol for 24 or 48 hours. Liver was dissected and immediately frozen for RNA isolation. The feeding experiments were repeated three times with four mice per group for each dietary treatment.

Liver RNA isolated from three chow-fed and four high-fat fed (two for 24 and 48 hours each) mice was used for global expression analysis. Affymetrix array hybridization and scanning were performed by the Core Facility at Dana-Farber Cancer Institute using Murine 430 2.0 chips (Affymetrix™). Array data were analyzed with d-CHIP array analysis program (Li and Wong (2001) *Proc. Natl. Acad. Sci. USA* 98, 31-36).

Free Fatty Acid Treatments

Primary hepatocytes were isolated following perfusion of whole liver first with perfusion buffer (Hank's Balanced Saline, HBSS) and then a collagenase solution (HBSS with 1% BSA and 0.05% collagenase). Dispersed cells were resuspended and seeded onto collagen-coated plates in DMEM supplemented with 10% FBS in the presence of 1 mM sodium pyruvate, 1 μM dexamethasone and 50 nM insulin. The cells were subsequently maintained in DMEM supplemented with 0.1% BSA and 1 mM sodium pyruvate for 24 hours before treatments. Free fatty acids were dissolved in ethanol as 100 mM stock solutions for further dilution in DMEM supplemented with 0.5% BSA to a final concentration of 400 μM. Hepatocytes were treated for 4 hours before RNA isolation and analysis.

Adenoviral Transduction

Male Wistar rats (Charles River Laboratories™) were fed a high-fat diet (TD96001, Harlan Taklad) for ten weeks. Animals were anesthetized with Nembutal and transduced with purified adenoviruses via tail vein injection (1×1012 viral particles per rat). Liver toxicity was monitored by plasma alanine aminotransferase and aspartate aminotransferase levels as determined by ALT/AST assay kit (505-OP, Sigma™). Plasma and liver were harvested six days following adenoviral transduction for gene expression and lipid analysis.

Analysis of Liver and Plasma Lipids

Liver triglycerides were extracted using chloroform/methanol (2:1) mix, dried in fume hood overnight, and dissolved in a solution containing 60% butanol and 40% of the Triton-X114/methanol mix (2:1). Liver and plasma triglyceride concentrations were measured using a calorimetric assay kit (337, Sigma™). Total plasma cholesterol was determined using the Infinity cholesterol reagent (401, Sigma™). For lipoprotein analysis, 300 μl of plasma was fractionated by FPLC. Concentrations of triglycerides and cholesterol in each fraction were determined as described above.

RNA Isolation and Analysis

Total RNA was isolated from liver or cultured hepatocytes using Trizol reagent (Invitrogen™). For real-time PCR analysis, cDNA was synthesized by reverse transcription using random primers and subjected to PCR amplification with genespecific primers in the presence of Cybergreen (Biorad™). Relative abundance of mRNA was calculated after normalization to 18S ribosomal RNA. Sequences for the primers used in this study are shown in Table 1. For hybridization, 20 μg of total RNA was resolved on a formaldehyde gel, transferred to nylon membrane and hybridized with 32P-labeled gene-specific probes. Hybridization to ribosomal protein 36B4 was included as loading control.

TABLE 1

Primers used for RNA Isolation and Analysis

| Gene | Primers |
| --- | --- |
| PGC-1 α (mouse) | agccgtgaccactgacaacgag (SEQ ID NO: 3) gctgcatggttctgagtgctaag (SEQ ID NO: 4) |
| PGC-1β (mouse) | ctccaggagactgaatccagag (SEQ ID NO: 5) cttgactactgtctgtgaggc (SEQ ID NO: 6) |
| SREBP1a (mouse) | cgccatggacgagctggccttc (SEQ ID NO: 7) gggaagtcactgtcttggttg (SEQ ID NO: 8) |
| SREBP1c (mouse) | atcggcgcggaagctgtcggg (SEQ ID NO: 9) gggaagtcactgtcttggttg (SEQ ID NO: 8) |
| SREBP2 (mouse) | tcagcaccgctccgcagacgag (SEQ ID NO: 10) taccgtctgcacctgctgctgg (SEQ ID NO: 11) |
| FAS (mouse) | ggttacactgtgctaggtgttg (SEQ ID NO: 12) tccaggcgcatgaggctcagc (SEQ ID NO: 13) |
| SREBP1a (Rat) | cgccatggacgagctggccttc (SEQ ID NO: 7) gggaagtcactgtcttggttg (SEQ ID NO: 8) |
| SREBP1c (Rat) | atcggcgcggaagctgtcggg (SEQ ID NO: 9) gggaagtcactgtcttggttg (SEQ ID NO: 8) |
| SREBP2 (Rat) | gcaaagcctcgtgacatcct (SEQ ID NO: 14) tgtggtgtagcgactgtctg (SEQ ID NO: 15) |
| HMG-CoA synthase1 (Rat) | tctctgcctgactgtggttc (SEQ ID NO: 16) ttcccagactcctcaaacag (SEQ ID NO: 17) |
| HMG-CoA reductase (Rat) | cacgctcacagtcgctggatag (SEQ ID NO: 18) cacttgctcgatgtccatgctg (SEQ ID NO: 19) |
| Mevalonate kinase (Rat) | gttgtcagaagtcctgctggtg (SEQ ID NO: 20) ggccacatcccagacctgctta (SEQ ID NO: 21) |

TABLE 1-continued

Primers used for RNA Isolation and Analysis

| Gene | Primers |
|---|---|
| Phosphomevalonate kinase (Rat) | gctgcagagcagacttggaggt (SEQ ID NO: 22)<br>ttccggcagaagaagcctgggt (SEQ ID NO: 23) |
| Mevalonate PP (Rat) | tgaacggtcgtgaggaggacgt (SEQ ID NO: 24)<br>caaggtataggctaggcaggcg (SEQ ID NO: 25) |
| Decarboxylase (Rat) | cagattatcattgaagtgactg (SEQ ID NO: 26)<br>gcttcactgcatctgggtgatc (SEQ ID NO: 27) |
| GPP synthase (Rat) | cagattatcattgaagtgactg (SEQ ID NO: 28)<br>gcttcactgcatctgggtgatc (SEQ ID NO: 29) |
| IPP isomerase (Rat) | gctcctgttacagcagagatcg (SEQ ID NO: 30)<br>gctccgcctttaagcgcttctg (SEQ ID NO: 31) |
| Squalene synthase (Rat) | gtgatcgctgacatctgtcac (SEQ ID NO: 32)<br>gaataggcgagaaaggccgattc (SEQ ID NO: 33) |
| Squalene epoxidase (Rat) | cctaccgctgtcgccatcgaaa (SEQ ID NO: 34)<br>ccgttaacgtcgtctctgacag (SEQ ID NO: 35) |
| Lanosterol synthase (Rat) | aagttctggctggctgtcctga (SEQ ID NO: 36)<br>cacttagccgagtggcgtagca (SEQ ID NO: 37) |
| Cyp51 (Rat) | atcgcctgcgccttcacgctta (SEQ ID NO: 38)<br>gttgtcagccgaccgtagaact (SEQ ID NO: 39) |
| 7-DHCR (Rat) | cctggcttcctgacttctgcca (SEQ ID NO: 40)<br>caggatgttggcacaccatagc (SEQ ID NO: 41) |
| 24-DHCR (Rat) | cctgcatgaggcagctggaga (SEQ ID NO: 42)<br>tcagtgcctcgcagccttgcagat (SEQ ID NO: 43) |
| LDL receptor (Rat) | cgagtgcccggatggctccgat (SEQ ID NO: 44)<br>catccgagccattttcacagtc (SEQ ID NO: 45) |
| ATP5j (Rat) | gttctgcagaggatcttcaggc (SEQ ID NO: 46)<br>gtcctccagatgcctgtcgctt (SEQ ID NO: 47) |
| SCD-1 (Rat) | cctcatcattgccaacaccatg (SEQ ID NO: 48)<br>tgtttgcgcacaagcagccaac (SEQ ID NO: 49) |
| FAS (Rat) | caggaactgaacggcattactc (SEQ ID NO: 50)<br>cattttctagggataacagcac (SEQ ID NO: 51) |

TABLE 1-continued

Primers used for RNA Isolation and Analysis

| Gene | Primers |
|---|---|
| PLTP (Rat) | agtctgcgctggagtctctggc (SEQ ID NO: 52)<br>caacagtgacgaagcctgcatg (SEQ ID NO: 53) |
| ABCA1 (Rat) | gccatcagttcattcctgaatg (SEQ ID NO: 54)<br>acctccgagagctgctgcttg (SEQ ID NO: 55) |
| ABCG1 (Rat) | actgcagcatcgtgtactgg (SEQ ID NO: 56)<br>gggatggtgtcaaagctgac (SEQ ID NO: 57) |
| ABCG8 (Rat) | atgcgcctgcccaagaccttc (SEQ ID NO: 58)<br>ccgatgctcactcttcggcgc (SEQ ID NO: 59) |

Transient Transfection

Mouse H2.35 hepatoma cells (CRL-1995, ATCC) were maintained in DMEM supplemented with 4% fetal bovine serum in the presence of 0.2 µM dexamethasone. Transient transfection was performed using Superfect (Qiagen™). In a typical experiment, 100 ng of reporter plasmids were mixed with 20-50 ng of expression constructs for transcription factors in the presence or absence of 0.5-1.0 µg of PGC-1 expression or RNAi constructs. Equal amounts of DNA were used for all transfection combinations by adding appropriate vector DNA. For LXR agonist treatments, T0901317 (Cayman Chemical™) was added to a final concentration of 10 µM 20 hours before luciferase assay. All transfection experiments were repeated at least three times in triplicate.

Chromatin Immunopercipitation

H2.35 hepatoma cells were infected with Ad-GFP, Ad-flag-PGC-1βc or Ad-PGC-1βB in the absence or presence of Ad-SREBP1c for 2 days. Cells were harvested following brief fixation with 10% formalin for preparation of sheared chromatin. Immunoprecipitation was performed using anti-flag or IgG control antibodies. The precipitates were reverse cross-linked for DNA isolation and PCR analysis.

Protein Interaction Assays

Physical association of PGC-1β and SREBP1c in cells was examined by coimmunoprecipitation. Briefly, H2.35 hepatoma cells were infected with Ad-SREBP1c, Ad-Flag-PGC-1β, Ad-Flag-PGC-1β alone or in combination as indicated. Nuclei were isolated from infected cells 48 hours following infection and extracted in a lysis buffer containing 20 mM HEPES (pH 7.9), 400 mM NaCl, 1.5 mM MgCl2, 0.5 mM DTT, 0.2 mM EDTA, 15% glycerol and 1 mM PMSF. Immunoprecipitation was performed in the lysis buffer supplemented with 1.5% Triton X-100 and 0.2 mg/ml BSA using polyclonal antibodies against SREBP1 (sc-8984, Santa Cruz Biotechnology™). PGC-1s in the complex were revealed by immunoblotting using a monoclonal antibody against the Flag epitope (M2, Sigma™).

For in vitro interaction assays, glutathione beads containing immobilized GST or GST-SREBP1c (1-471) were incubated with in vitro translated 35S-labeled full length or truncated mutants of PGC-1β in a binding buffer containing 20 mM HEPES (pH=7.2), 80 mM KCl, 150 mM NaCl, 0.05% NP-40, 5% glycerol and 0.5 mM DTT. The beads were washed in the same buffer four times. Proteins associated with the beads were analyzed by SDS-PAGE followed by autoradiography. For detecting LXR/PGC-1β interaction, immobilized GST or GST-PGC-1β (N-terminus) was incubated with in vitro translated 35S-labeled LXRα and processed as described above.

PGC-1β RNAi Vectors

The RNAi constructs for PGC-1β were generated using two sequences in the coding region of PGC-1β: 5'-GATATC-CTCTGTGATGTTA-3' (SEQ ID NO: 60) and 5'-GTACG-GAACTGCATAAGCA-3' (SEQ ID NO: 61). Oligonucleotides containing these sequences were subcloned into the pSUPER-retro vector under the control of the polymerase III H1-RNA promoter. For transient transfection, 1.0 μg of pSUPER vector or PGC-1β RNAi constructs were used in combination with 100 ng of reporter plasmids and 50 ng of expression constructs for appropriate transcription factors.

PGC-1β RNAi adenoviruses were generated using the expression cassettes derived from the pSUPER vectors. For knockdown experiments, H2.35 hepatoma cells were infected with either Ad-GFP or Ad-PGC-1β RNAi adenoviruses for 48 hours before incubation with Ad-SREBP1c. Total RNA were harvested from infected cells 20 hours following Ad-SREBP1c infection and analyzed by real-time PCR.

Adenoviral transduction in mice was performed by tail vein injection at $1.5 \times 10^{11}$ viral particles per mouse (three-month old C57B1/6 males). After four days, the animals were switched to a high-fat diet for two more days. Plasma samples were collected before and after high-fat feeding and assayed for triglyceride and cholesterol concentrations. HDL cholesterol was measured using an automated ACE Clinical Chemistry System (ALFA Wassermann™, N.J.). Liver was dissected at the end of high-fat feeding for gene expression and lipid analysis.

Example 1

Stimulation of a Program of Hepatic Lipogenesis by High-Fat Feeding

Figure 2:
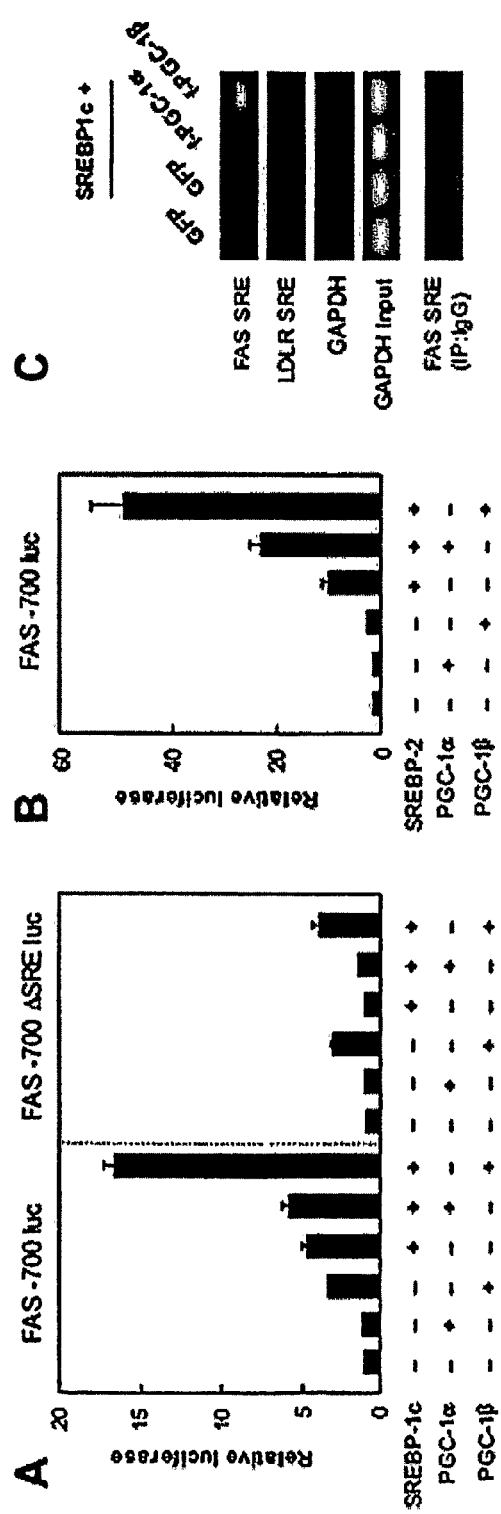
FIGS. 2 A-F depict the coactivation of the SREBP family of transcription factors by PGC-1β. In particular.
Figure 2:
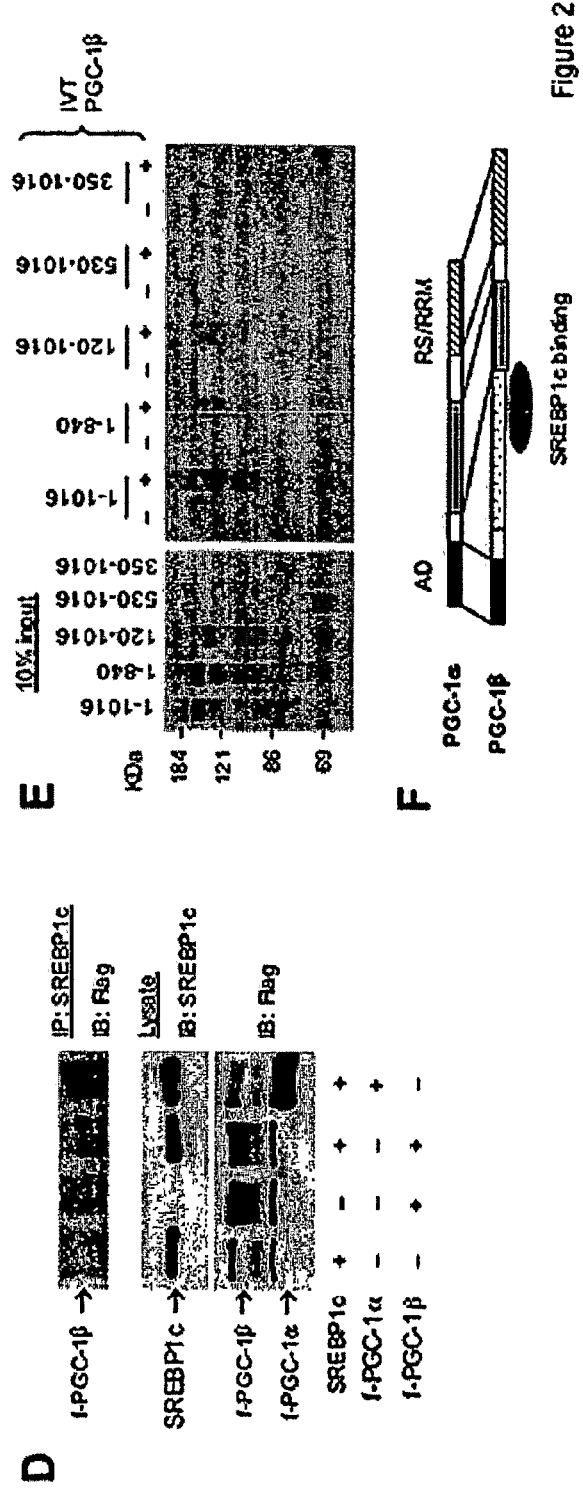

Mice were fed a diet rich in saturated fats but with little or no cholesterol (58% fat, mainly from hydrogenated coconut oil; D 12331, Research Diets™). Because these diets are known to bring about many chronic effects, such as insulin resistance and obesity, the experiment focused only on early changes. Mice were switched from standard rodent chow to the high-fat diet for 1 and 2 days, and hepatic gene expression was examined with Affymetrix™ arrays. Results obtained from clustering analysis revealed that the expression of a large number of genes involved in de novo lipid synthesis are strongly induced following this short-term high-fat feeding, including those responsible for fatty acid, cholesterol and triglyceride synthesis (FIG. 1A). The expression of mRNAs encoding glucose transporter 2, several enzymes in the glycolysis and pentose phosphate-pathways and those involved lipid trafficking, are also coordinately increased. mRNA levels for many enzymes in the cholesterol synthesis pathway, such as HMG-CoA reductase, phosphomevalonate kinase and lanosterol synthase, are also significantly elevated in response to dietary saturated fats. The activation of this hepatic lipogenic program is further accompanied by an increased expression of two potentially important hepatic transcriptional regulators, SREBP1c, a central regulator of lipogenic gene expression, and PGC-1β, a transcription coactivator in the PGC-1 family (FIG. 1A). The mRNA level of SREBP1c is elevated more than 7-fold at day 1 of high-fat feeding, as determined by quantitative real-time PCR analysis (FIG. 1B). The expression of SREBP1a is also induced approximately 2-fold. In contrast, SREBP2 expression remains unchanged. Unlike PGC-1α, which is only slightly induced by the dietary switch, the expression of PGC-1β mRNA is stimulated more than 4-fold in response to high-fat feeding, paralleling that of SREBP1c (FIG. 2B). Several-fold induction of mRNA for lipogenic genes, such as fatty acid synthase (FAS) and HMG-CoA reductase, is also shown by real-time PCR analysis (FIG. 1B). The expression of PGC-1β is not altered in skeletal muscles and white adipose tissue under these conditions.

To examine whether dietary cholesterol had any impact on the expression of SREBPs and PGC-1β mice were fed a control diet containing 0.07% cholesterol or a similar diet containing 2% cholesterol. The results demonstrate that a high cholesterol feeding suppresses the hepatic expression of mRNA encoding SREBP2, a transcriptional regulator of cholesterol biosynthesis, along with the expression of HMGCoA reductase (FIG. 1C). The expression of PGC-1β is not altered by dietary cholesterol content while SREBP1c mRNA is slightly increased in response to the high-cholesterol diet (FIG. 1C). The mRNA level of several lipogenic enzymes including FAS, stearoyl-CoA desaturase 1 (SCD-1) and glucose kinase (GK) remains largely unchanged. These results demonstrate that dietary saturated fats and cholesterol have distinct effects on the expression of mRNA for the SREBPs and PGC-1β, as well as genes involved in hepatic fatty acid and cholesterol synthesis. This induction of the genetic program of hepatic lipogenesis following acute intake of a high saturated fat diet was not previously observed.

Previous studies have demonstrated that fatty acids, especially polyunsaturated species, suppress both the expression of SREBP1c and the generation of cleaved, nuclear isoforms (Hannah et al. (2001) J. Biol. Chem. 276, 4365-4327). To determine whether dietary fats have a direct impact on PGC-1β expression, primary hepatocytes were treated with various saturated, unsaturated and trans fatty acids and the levels of PGC-1β mRNA by realtime PCR analysis was examined. While monounsaturated (oleic acid, $C_{18:1}$n-9) and polyunsaturated (linoleic acid, $C_{18:2}$n-6, EPA, $C_{20:5}$n-3, and arachidonic acid, $C_{20:4}$n-6) only slightly induce PGC-1β expression, saturated fatty acids of varying chain length ($C_{10}$:0 to $C_{18}$:0) elevate PGC-1β mRNA levels much more strongly (FIG. 1D). Trans fatty acids such as elaidic acid (trans-$C_{18:1}$n-9) and trans-vaccenic acid (trans-$C_{18:1}$n-7), abundantly present in hydrogenated vegetable oil and dairy products, respectively, also robustly induced the expression of PGC-1α (3.2-fold). In contrast, fatty acid treatments have no effect on the expression of PGC-1α mRNA under these conditions, except stearic acid ($C_{18}$:0), which also induces PGC-1β mRNA 2.2-fold (FIG. 1D). These results indicate that certain fatty acids, especially saturated and trans fatty acids, directly stimulates PGC-1β expression in a cell-autonomous manner.

Example 2

Coactivation of the SREBP Family of Transcription Factors by PGC-1β

PGC-1β has been shown to strongly coactivate several transcription factors, including nuclear receptors such as PPARβ and ERRs, and to a lesser extent, HNF4α (Kamei et al. (2003) Proc. Natl. Acad. Sci. USA 100, 12378-12383; Lin et al. (2002a) Nature 418, 797-801; Lin et al., (2003) J. Biol. Chem. 278, 30843-30848). PGC-1β also coactivates NRF-1, which is not a nuclear receptor. Co-induction of PGC-1β and SREBP 1c in the liver of high-fat fed mice suggests that PGC-1β might modulate the transcriptional activity of SREBP1c and influence the expression of its target genes. To examine this theory, hepatoma cells were transiently transfected with a luciferase reporter under the control of the FAS promoter; this construct contained a functional SREBP binding site and is highly responsive to the SREBPs (Joseph et al. (2002) *J. Biol. Chem.* 277, 11019-11025; Magana and Osborne (1996) *J. Biol. Chem.* 271, 32689-32694; Tontonoz et al. (1993) *Mol. Cell. Biol.* 13, 4753-4759). The results demonstrate that SREBP1c expression is enhanced from the luciferase reporter gene by approximately 5-fold in transiently transfected H2.35 mouse hepatoma cells (FIG. 2A). PGC-1β greatly augments the transcriptional activity of SREBP1c on the FAS promoter, as shown by a 17-fold increase in the luciferase activity compared to the basal levels. In contrast, PGC-1α shows a minimal effect on the induction of reporter gene activity by SREBP1c. A mutation of the SREBP binding site on the promoter completely abolishes its activation by both SREBP1c alone and the combination of SREBP1c and PGC-1β, suggesting that PGC-1β coactivates SREBP1c through the SRE on this promoter. PGC-1β also strongly increases the activity of SREBP2 and SREBP1a in these coactivation assays (FIG. 2B).

To determine whether PGC-1β was recruited to SREs present in the promoter/enhancer region of endogenous SREBP target genes, chromatin immunoprecipitation (CHIP) assay was performed. As shown in FIG. 2C, PGC-1β, but not PGC-1α, is present in proximity to the SRE on the FAS promoter. The recruitment of PGC-1β to SREBP binding sites depends on their promoter context; PGC-1β is not recruited to the SRE on the LDLR promoter. No PCR product was detected when control IgG was used in the immunoprecipitations (FIG. 2C). These results demonstrate that SREBP1c is able to directly recruit PGC-1β to the proximity of its binding sites on the target promoters. In fact, these two proteins physically interact with each other in cells as shown by co-immunoprecipitation assays. SREBP1c interacts with and precipitates PGC-1β, but not PGC-1β, when these proteins are co-expressed in hepatoma cells (FIG. 2D). This is observed despite the fact that the expression level of PGC-1β is higher than that of PGC-1β. In order to identify domains of PGC-1β that could interact with SREBP1c, a fusion protein was utilized between GST and the processed form of SREBP1c. Full length PGC-1β interacts well with SREBP1c (FIG. 2E), and an analysis of PGC-1β mutants reveals that a domain (amino acid 350-530) unique for PGC-1β, but absent in PGC-1α, is required for interaction between SREBP1c and PGC-1β (FIG. 2E-F). The results demonstrate that PGC-1β, but not PGC-1α, coactivates the SREBP family of transcription factors by direct physical association.

Example 3

Activation of Hepatic Lipogenesis and Hyperlipidemia by PGC-1β

Figure 3:
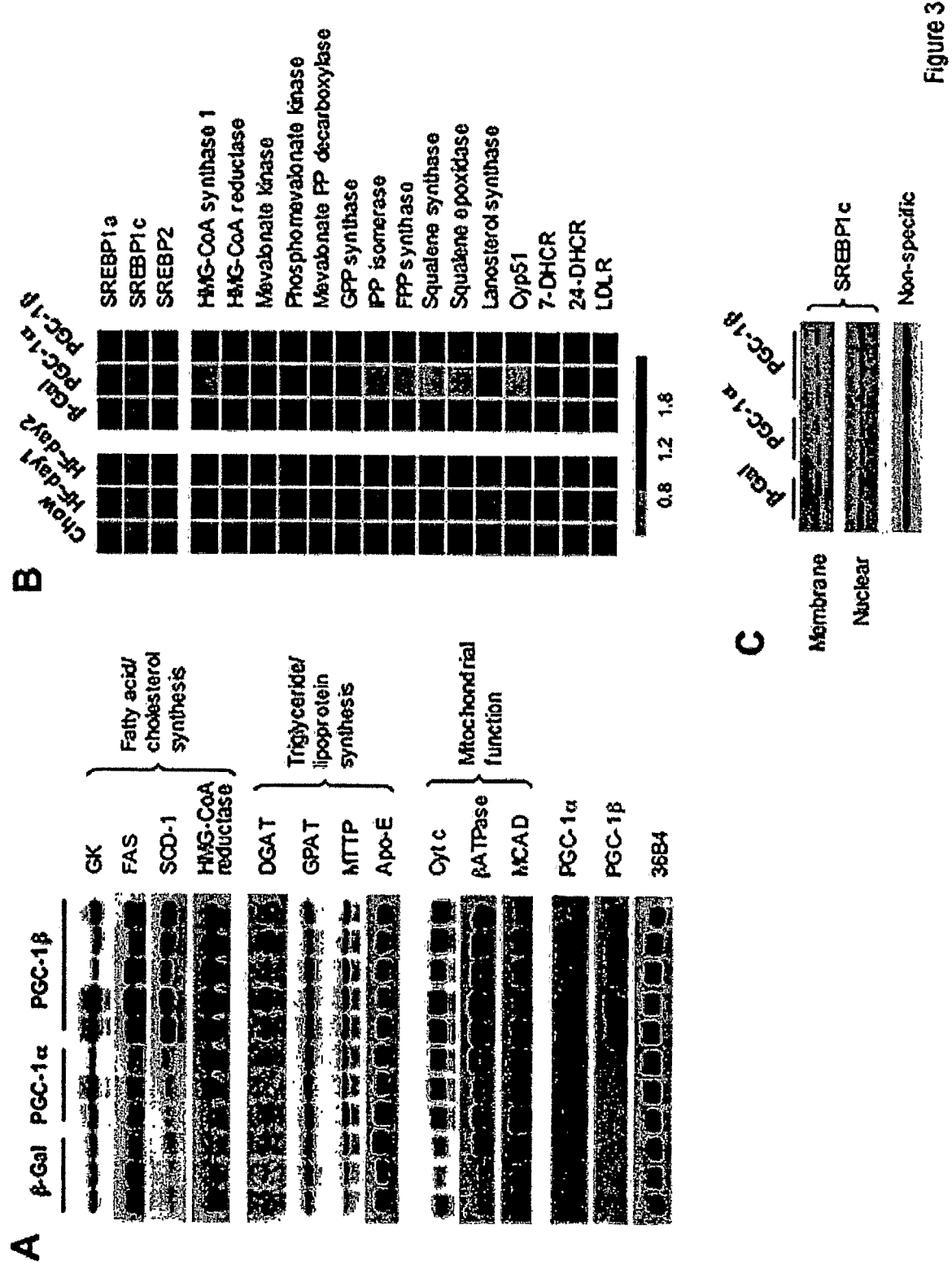
FIGS. 3 A-C depict the induction of mRNAs encoding enzymes in the pathways of fatty acid and cholesterol biosynthesis by PGC-1β. In particular.

To examine the effects of PGC-1β on the expression of endogenous lipogenic genes, rats via tail vein injections were infused with recombinant adenoviruses expressing β-galactosidase (β-Gal), PGC-1α or PGC-1β. Adenovirus almost exclusively infected hepatocytes when introduced through the tail vein. The results demonstrate that both PGC-1β and PGC-1α stimulate the expression of lipogenic genes such as cytochrome c, βATPase and medium chain acyl-CoA dehydrogenase (MCAD) when ectopically expressed in liver (FIG. 3A). In addition to the induction of lipogenic genes, PGC-1β also powerfully stimulates the expression of genes involved in lipid synthesis, such as FAS, SCD-1, HMG-CoA reductase, DGAT and GPAT, all of which are well-known SREBP targets. In contrast, PGC-1α has little or no effect on the expression of these genes. The expression of microsomal triglyceride transfer protein (MTTP), a gene that regulates VLDL secretion and has a mutation in familial abetalipoproteinemia, is induced by both PGC-1α and PGC-1β. Gene expression analysis by real-time PCR reveal that in addition to modulating HMG-CoA reductase, PGC-1β also increases mRNA level of multiple enzymes in the cholesterol synthesis pathway, while PGC-1α has much weaker effects (FIG. 3B). In fact, many of these PGC-1β target genes are also highly induced in response to high-fat feeding, which demonstrate that PGC-1β is a key factor in mediating the effects of dietary saturated fats on hepatic lipogenesis including cholesterol biosynthesis. In addition, the expression of LDLR, a classic SREBP target, is not elevated by PGC-1β. This induction of SREBP target genes by PGC-1β does not appear to be due to increased levels of SREBP transcription factors as shown by mRNA and protein analysis (FIG. 3B-C). Rather, these results are consistent with the observation that PGC-1β coactivates SREBPs through direct physical association and augmentation of their transcriptional activity.

Figure 4:
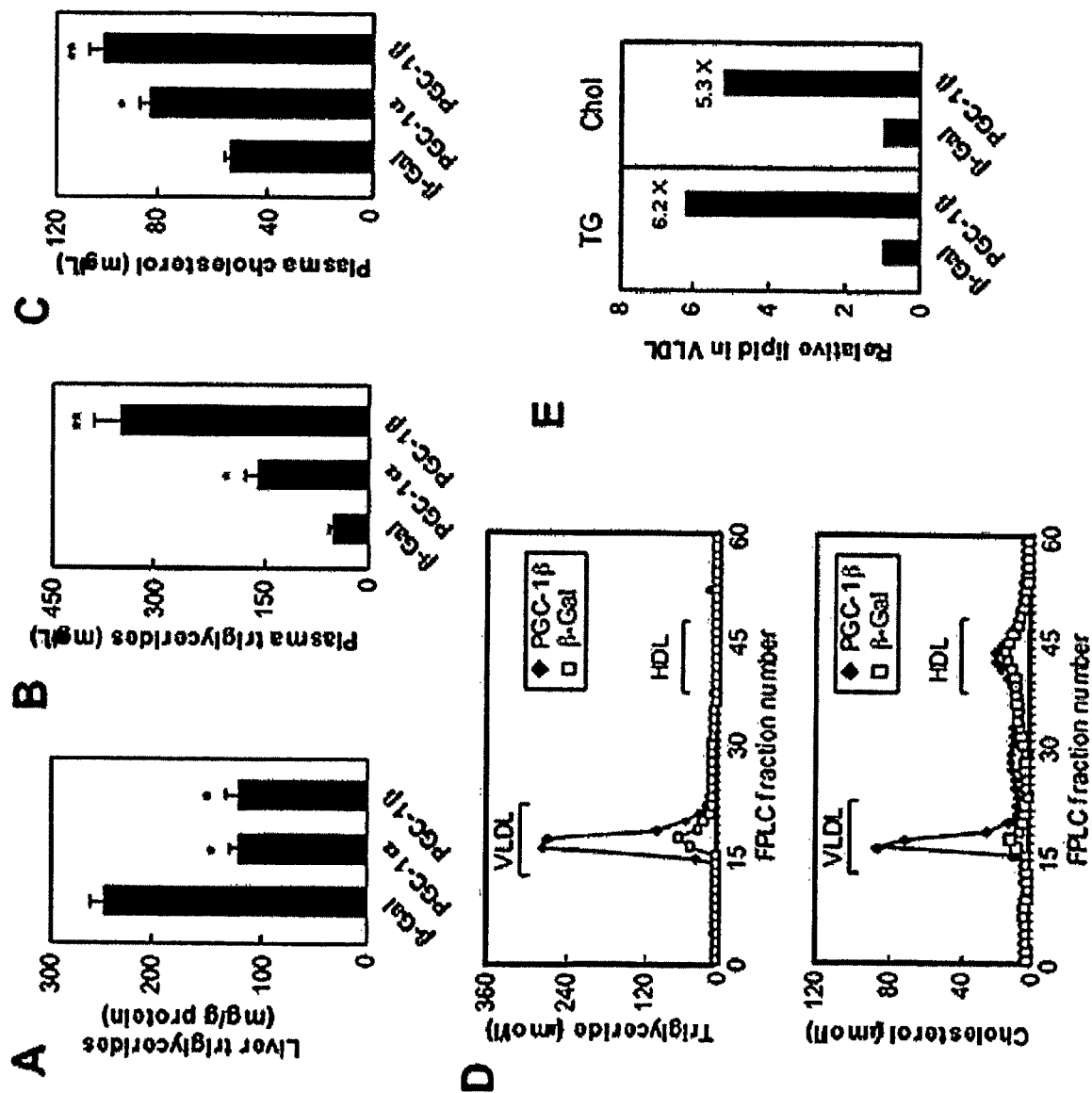
FIGS. 4 A-E depict the induction of hyperlipidemia by PGC-1β. Rats were transduced via tail vein injection with adenoviruses. In particular, FIGS. A-C depict liver triglycerides (A), plasma triglycerides (B), and total plasma cholesterol (C) in rats transduced with Ad-β-Gal, Ad-PGC-1α or Ad-PGC-1β. (A)*: p<0.0003; (B)*: p<0.0001, **: p<0.007; (C)*: p<0.0004, **: p<10-6.

Transgenic expression of SREBP in mouse liver is shown to activate lipogenic gene expression and increase the rate of fatty acid and cholesterol synthesis. The bulk of lipids, however, accumulates in liver and fails to be exported to peripheral tissues for storage and utilization (Horton et al. (1998) *J. Clin. Invest.* 101, 2331-2339; Shimano et al. (1996) *J. Clin. Invest.* 98, 1575-1584; Shimano et al. (1997) *J. Clin. Invest.* 99, 846-854). Plasma triglyceride levels are actually reduced in the transgenic mice when compared to wild type controls, probably due to increased LDLR levels in liver (Shimano et al. (1997) *J. Clin. Invest.* 99, 846-854). To assess the impact of PGC-1β on systemic lipid homeostasis, lipid levels in liver and plasma were examined following adenoviral transduction in ad lib high-fat fed rats. In light of the previous results with SREBP expression, adenoviral mediates PGC-1β expression in liver lowered hepatic triglyceride content by more than 50% in these rats (FIG. 4A). This decrease in hepatic lipid storage is explained by an increase in lipid export from this organ as PGC-1β expression in liver caused profound plasma hypertriglyceridemia in rats, with plasma triglyceride concentrations elevated more than 6-fold when compared to control rats receiving Ad-β-Gal (FIG. 4B). Similar increase in plasma triglycerides is also observed in chow-fed rats, while the anti-steatotic effect of PGC-1β is not as pronounced due to much less lipid accumulation in the liver from those animals. PGC-1α also lowered liver triglyceride content while slightly raising plasma triglyceride levels (FIG. 4A-B). Analysis of plasma cholesterol indicated that total cholesterol increased by approximately 55% and 200% by PGC-1α and PGC-1β, respectively (FIG. 4C). The increase in plasma cholesterol is mainly a result of accumulation of cholesterol in the VLDL fractions as shown by FPLC analysis of lipoprotein profiles (FIG. 4D). In fact, the level of triglycerides and cholesterol in VLDL is increased 6.2- and 5.3-fold, respectively, in response to PGC-1β compared to the β-Gal control (FIG. 4E). In contrast, the level of HDL cholesterol is largely unaffected. This is significant in light of the fact that VLDL cholesterol is the precursor of LDL cholesterol. The results strongly demonstrate that although PGC-1β coactivates the SREBPs and increases the expression of the lipogenic genes that are targets of the SREBPs; this coactivator also modulates lipid transport pathways that lead to changes in the balance between hepatic and plasma lipids.

Figure 5:
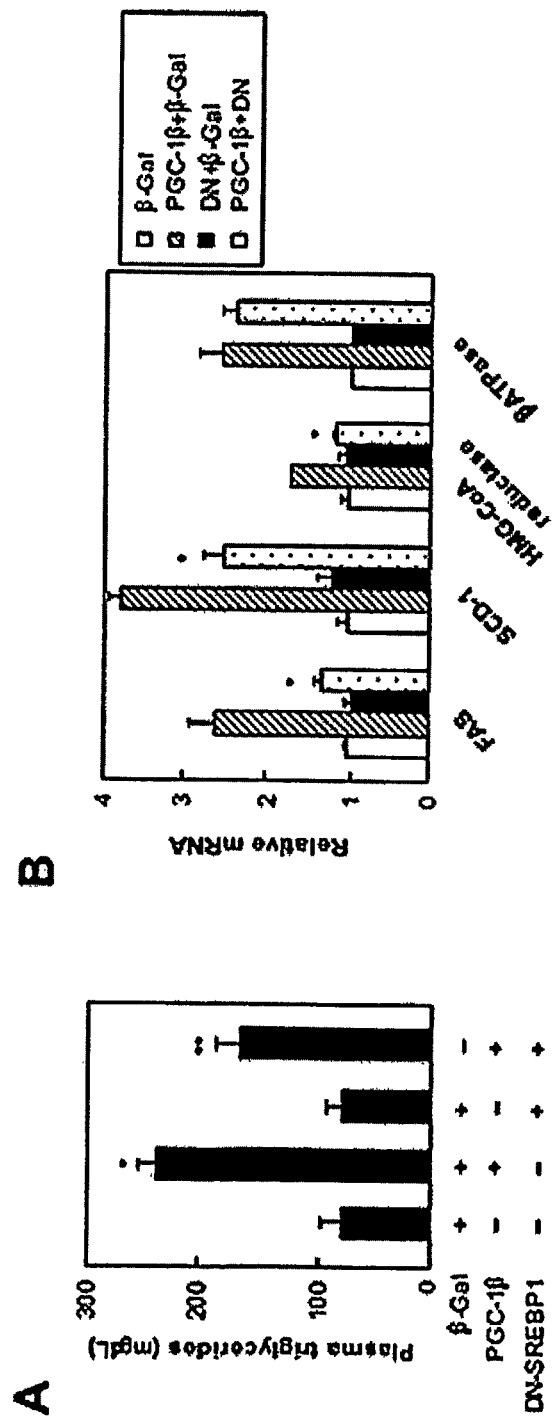
FIGS. 5 A-B illustrate the requirement of the SREBP activity in the hepatic effects of PGC-1β. In particular.

To determine whether SREBP is necessary for mediating the effects of PGC-1β on lipogenic gene expression, rats were infused with Ad-PGC-1β in combination with a well-characterized dominant negative mutant of SREBP (Foretz et al. (1999) *Proc. Natl. Acad. Sci. USA* 96, 12737-12742; Kim and Spiegelman (1996) *Genes Dev.* 10, 1096-1107). Equal titers ($1.2 \times 10^{12}$ viral particles) of adenoviruses were delivered into rats via tail vein injection. As shown in FIG. 5A, while DN-SREBP alone had no effect on the levels of plasma triglycerides compared to β-Gal controls, the DN mutant significantly diminishes hypertriglyceridemia caused by PGC-1β. Consistent with these results, the induction of several lipogenic genes, such as FAS, SCD-1 and HMG-CoA reductase, are also reduced when rats are transduced with both Ad-PGC-1β, and Ad-DN-SREBP (FIG. 5B). In contrast, the induction of βATPase, a mitochondrial gene not known to be regulated by SREBP, is not affected by DN-SREBP, either alone or in the presence of PGC-1β. These results indicate that at least a significant portion of the effects of PGC-1β on lipogenic gene expression is mediated through the SREBP family of transcription factors.

Example 4

Modulation of the LXRβ Pathway by Both PGC-1α and PGC-1β

Figure 9:
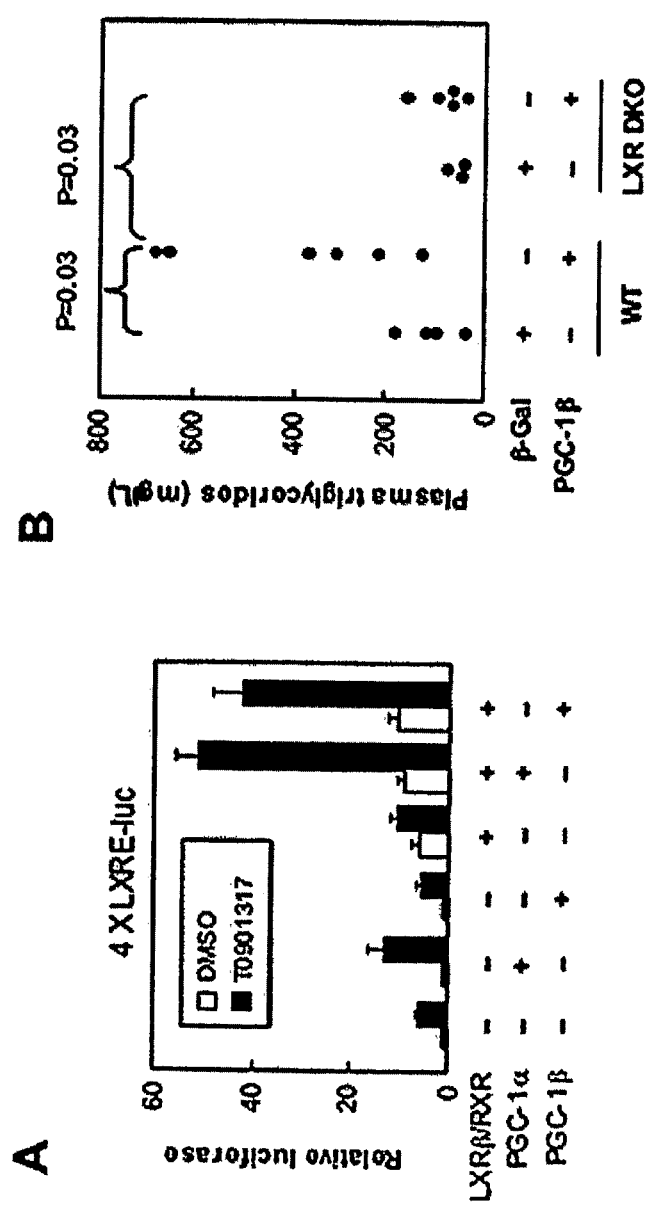
FIG. 9A depicts the coactivation of LXRβ by PGC-1α and PGC-1β. In particular, H2.35 hepatoma cells were transiently transfected with plasmids as indicated. After 24 hours, the cells were treated with 10 μM of T0901317 for 16 hours before luciferase assay.
FIG. 9B depicts the requirement of LXRα and LXRβ in mediating hyperlipidemic effect of PGC-1β in vivo. In particular, wild type or LXRα/β-deficient (LXR DKO) mice were transduced with adenoviruses expressing control β-Gal or PGC-1β. Plasma triglyceride concentrations were measured 5 days following viral transduction. Note that PGC-1β fails to elevate plasma triglyceride levels in the absence of LXRs.
Figure 10:
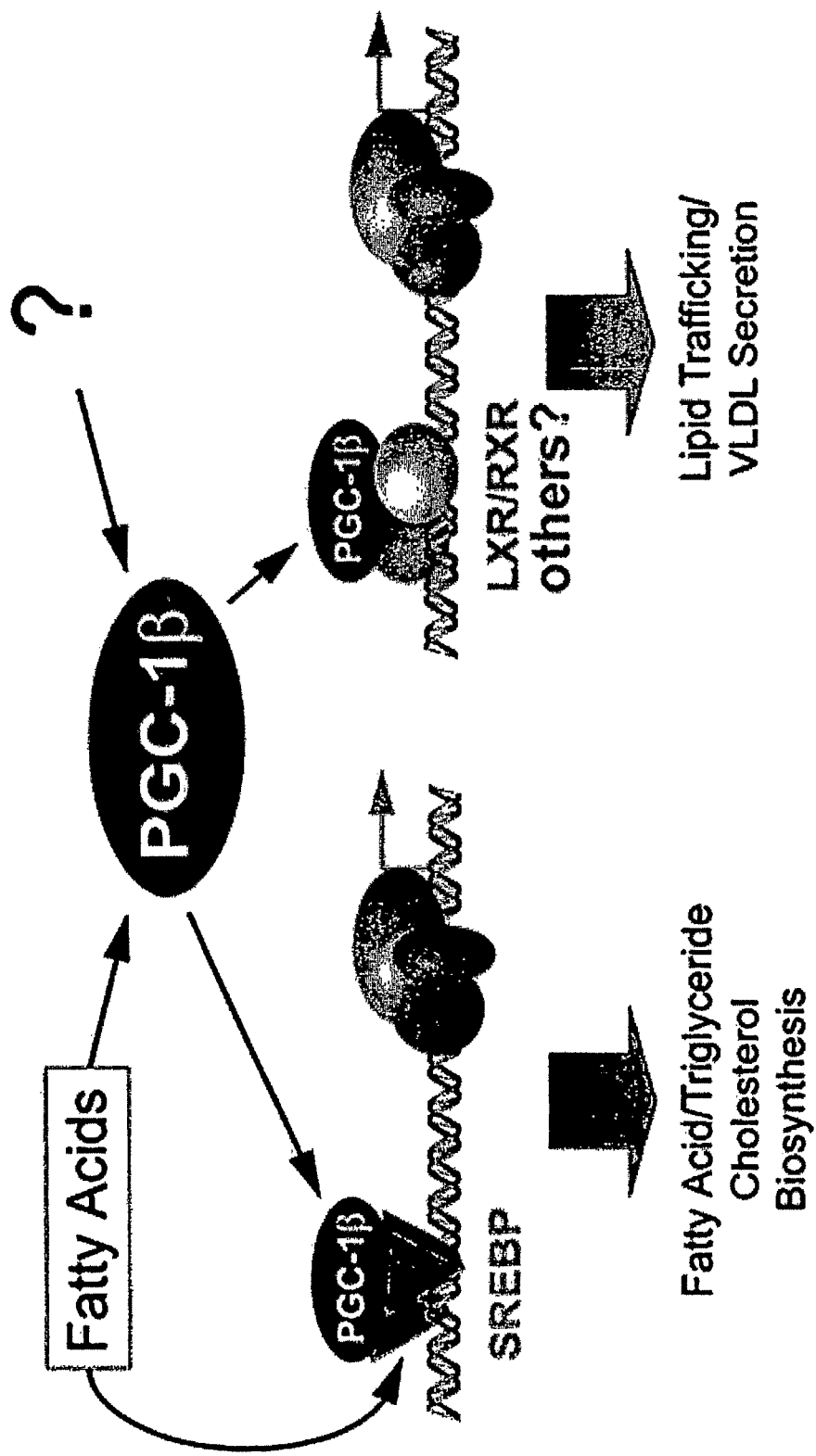
FIG. 10 illustrates the coordination of lipid synthesis and lipoprotein secretion through transcriptional coactivation by PGC-10. PGC-1β stimulates hepatic lipid synthesis by coactivating the SREBP family of transcription factors. PGC-1β also activates lipoprotein secretion through its coactivation of transcription factors including LXR.

As shown in Example 3, PGC-1β induces a drastic increase in the levels of VLDL triglycerides and cholesterol, suggesting a role for PGC-1β in enhancing hepatic lipid transport and VLDL secretion. Indeed, hypertriglyceridemia induced by PGC-1β is reminiscent of that caused in animals by the activation of liver-X receptor (LXR) with an agonist ligand (Grefhorst et al. (2002) *J. Biol. Chem.* 277, 34182-34190; Schultz et al. (2000) *Genes Dev.* 14, 2831-2838). LXRα is highly expressed in liver, adipose tissue, gut and macrophage. Activation of LXRα has been shown to play an important role in the regulation of lipid export and reverse cholesterol transport in macrophages (Chawla et al. (2001) *Mol. Cell.* 7, 161-171). To determine whether PGC-1β affects transcriptional activity of LXRα, a reporter plasmid that contains multimerized LXR binding sites (4 XLXRE-luc) was cotransfected with PGC-1α and PGC-1β. As shown in FIG. 6A, PGC-1β strongly augments the activation of reporter gene expression by LXRα and RXRβ in a ligand dependent manner. The combination of LXRα/RXRβ and PGC-1β increased luciferase activity by more than 240-fold when compared to the basal level in the presence of LXRα ligand. Similarly, both PGC-1 coactivators are able to augment the transcriptional activity of LXRβ when assayed on this reporter construct (FIG. 9A). The effects of PGC-1β on reporter gene expression was also seen when no exogenous LXR or RXRβ were added, probably reflecting the presence of endogenous LXR and RXR in H2.35 hepatoma cells. An examination of whether PGC-1α and -1β coactivate LXRα on endogenous promoters was performed. Cotransfection of PGC-1s increases the promoter activity of the ATP binding cassette transporter A1 (ABCA1) by approximately 2-3 fold compared to LXRα/RXRβ alone (FIG. 6B). A mutation of the LXR binding site on the promoter completely abolishes its regulation by LXR and PGC-1s, indicating that LXR binding to its response element on the ABCA1 promoter: is required for mediating effects of the PGC-1s. In fact, both PGC-1β and PGC-1β are recruited to the proximity of the LXREs present on the promoters of CYP7a1 and ABCA1, known LXR target genes (FIG. 6C). Furthermore, these two coactivators are able to directly bind LXRα in an in vitro interaction assay (FIG. 6D). The N-termini of both PGC-1s (PGC-1α N400 and PGC-1β N350), which contain the conserved LXXLL motif involved in nuclear receptor binding, is sufficient to interact with LXRα. The interaction between PGC-1β and LXRα appears to be more ligand dependent than PGC-1α. Deletion of a small region that contains the conserved LXXLL motif (PGC-1β N350) reduced the binding between PGC-1β and LXR and completely abolishes the effects of ligand (FIG. 6D).

To determine whether the PGC-1 coactivators regulate the expression of endogenous LXR target genes, the mRNA level of several genes known to be LXRα targets were measured by real-time PCR analysis of RNA isolated from adenovirally transduced rat liver. Consistent with the reporter gene assays, both PGC-1 coactivators induce the mRNA expression for CYP7a1 phospholipids transfer protein (PLTP), ABCA1 and ABCG1, with CYP7α1 being most responsive to ectopic expression of both PGC-1α and PGC-1β (FIG. 6E). In addition, the expression of ABCG8 is not altered in response to PGC-1s while ABCG5 is slightly reduced by PGC-1 (FIG. 6E). Therefore, in contrast to the regulation of genes involved in fatty acid and cholesterol synthesis which are solely PGC-1β targets, both PGC-1α and PGC-1β appear to activate the expression of LXR target genes.

Since mice deficient in the LXRs are known to express SREBP I c very poorly (Repa et al., (2000) *Genes Dev* 14, 2819-2830) it is not possible to genetically determine the role of the LXRs in the PGC-1β responses independent of SREBP1c. However, introduction of adenoviral PGC-1β into mice lacking both LXRα and LXRβ shows a complete loss of the hyperlipidemic response shown in wild type animals, consistent with a role of the LXRs in this pathway (FIG. 9B).

Example 5

Requirement for PGC-1β in the Transcriptional Activity of SREBPs

Figure 7:
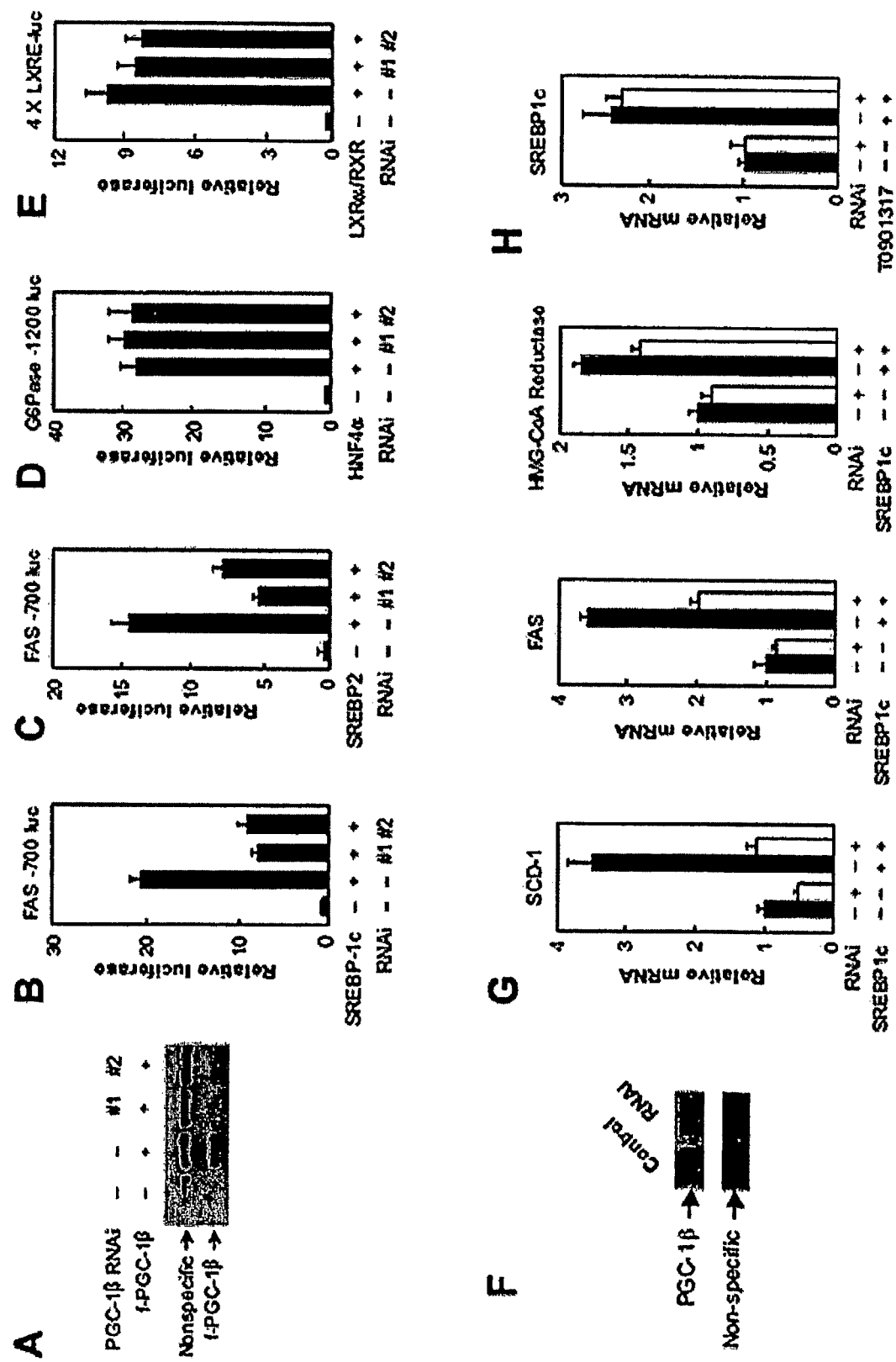
FIGS. 7 B-E depict hepatoma cells that were transiently transfected with FAS—700 luc (B-C), G6Pase −1200 luc (D) or 4×LXRE-luc (E) in combination with plasmids. For RNAi, either a vector control or RNAi constructs directed toward PGC-1β were included in the transfection experiments. Luciferase activity was measured 48 hours after transfection.

The fact that PGC-1β is highly induced along with SREBP1a/1c in response to high-fat feeding suggests that the concentration of PGC-1β in hepatocytes is a necessary and limiting factor for SREBP activity. To examine this theory, RNAi vectors (SEQ ID NO 60 and SEQ ID NO:61) were constructed that specifically knock down PGC-1β levels in cells. As shown in FIG. 7A, both RNAi vectors directed toward PGC-1β reduces the protein level of PGC-1β by 60-90% when tested in transient transfection assays compared to the control vector. To determine whether PGC-1β is required for SREBP function, the effect of PGC-1β RNAi on SREBP transcriptional activity in transient transfections was analyzed. SREBP1c strongly augments FAS promoter activity when assessed in transfected hepatoma cells (FIG. 7B). Activation of the FAS promoter by SREBP1c is reduced more than 60% by PGC-1β RNAi constructs compared to the control vector or a vector expression random RNAi sequence. A very similar reduction of SREBP transcriptional activity is also observed with these RNAs, when combined with SREBP2 and SREBP1a (FIG. 7C). These PGC-1β RNAi vectors have little or no effect on the regulation of G6Pase promoter activity by PGC-1α and HNF4α (FIG. 7D). These RNAi vectors also do not alter LXRα/RXRα transcriptional activity when assayed on a reporter containing multimerized LXR responsive elements (FIG. 7E), due to the presence of PGC-1α and/or other coactivator proteins for LXRs in hepatocytes. The data strongly indicate that PGC-1β activity is required for the full transcriptional effects of SREBPs on the FAS promoter.

Figure 6:
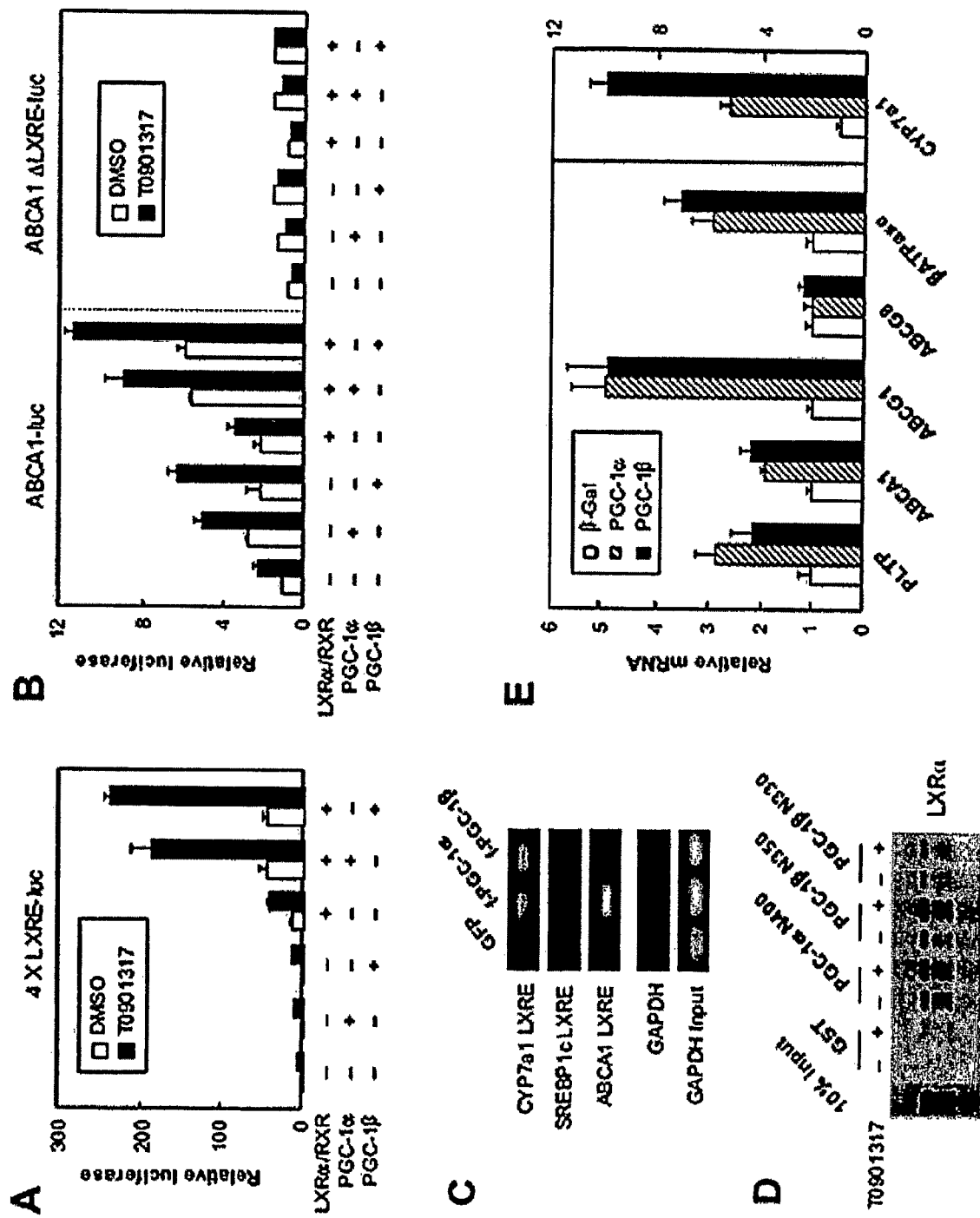
FIG. 6A-E illustrate the coactivation of LXRα by PGC-1α and PGC-1β. In particular.

To determine whether PGC-1β is required for the expression of endogenous SREBP1c targets, an adenoviral RNAi vector (Ad-RNAi) using the RNAi directed toward PGC-1β (SEQ ID NO: 60) was constructed and its effect examined on the expression of lipogenic genes. As shown in FIG. 7F, infection of hepatoma cells with this Ad-RNAi reduces endogenous PGC-1β protein by approximately 80% in these H2.35 cells. No effect on PGC1-α was detected. As shown in FIG. 7G, SREBP1c expression in hepatoma cells strongly stimulates mRNA abundance of several lipogenic genes such as SCD-1 (3.5-fold), FAS (3.6-fold), HMG-CoA reductase (1.8-fold) and LDLR (2.4-fold). Hepatoma cells infected with the Ad-RNAi directed toward PGC-1β reduces basal mRNA levels of SCD-1 (50%), but not FAS and HMG-CoA reductase. The induction of all these genes in response to SREBP c, however, is greatly impaired in the cells infected with Ad-RNAi compared to the control GFP. Notably, while the induction of FAS and HMG-CoA reductase is reduced more than 50%, the expression of SCD-1 mRNA is reduced to near the basal level even in the presence of SREBP1c. In contrast, the induction of the LXR target genes, such as SREBP1c, is not affected by PGC-1β knockdown (FIG. 7H), reflecting the observation that PGC-1β is also capable of co-activating LXR and stimulating the expression of its targets (FIG. 6).

Figure 8:
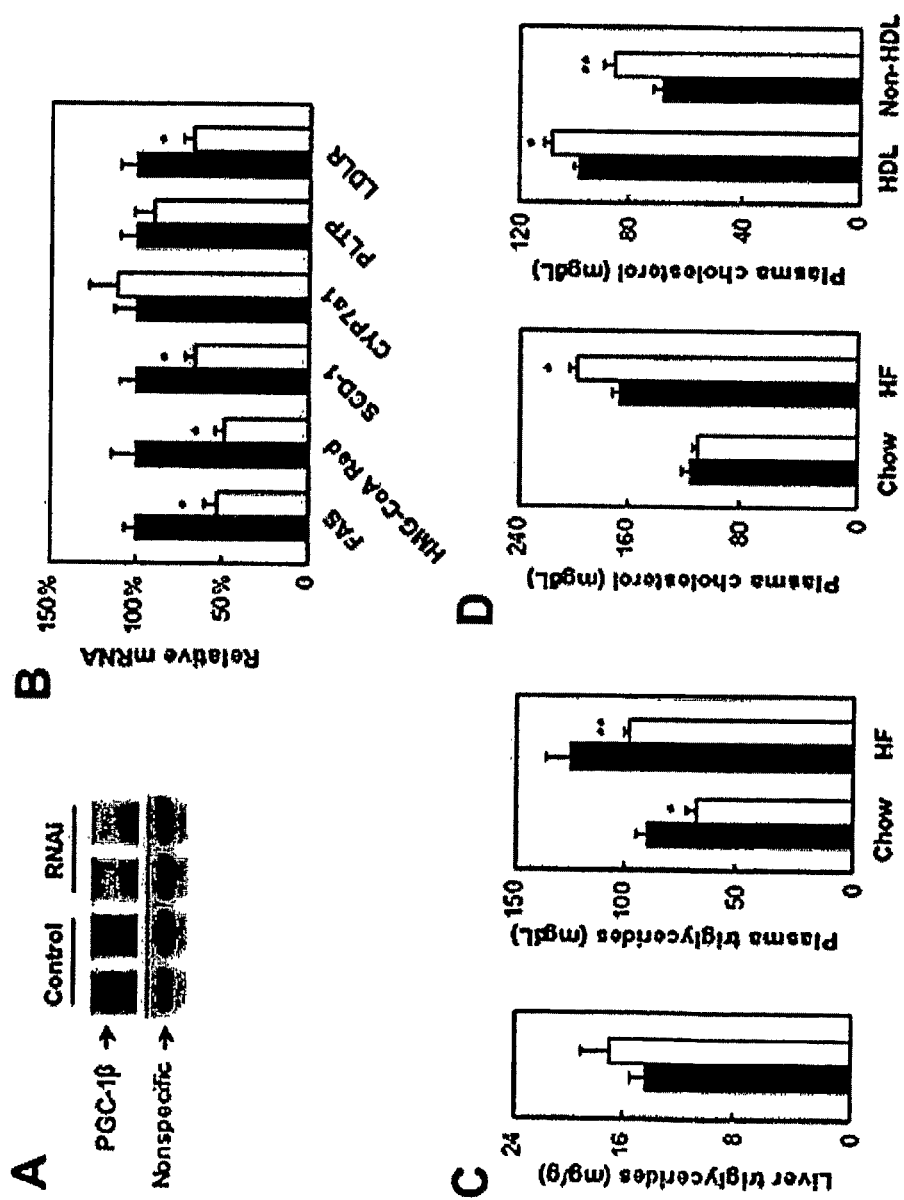
FIG. 8 A-D illustrate the requirement of PGC-1β for lipogenic gene expression and lipid homeostasis in vivo. In particular.

To examine whether PGC-1β is required for the activation of lipogenic gene expression in vivo, especially in the context of high-fat feeding, mice with Ad-RNAi were transduced against PGC-1β, or a control random RNAi for four days and then switched animals to a high-fat diet for two days. Results demonstrate that the Ad-RNAi directed against PGC-1β greatly reduced endogenous PGC-1β protein in the liver (FIG. 8A). Analysis of hepatic gene expression indicates that the mRNA level of several key lipogenic enzymes, including FAS, SCD-1 and HMG-CoA reductase, is significantly decreased in the liver from mice receiving Ad-RNAi compared to the control RNAi vector (FIG. 8B). The expression of CYP7a1 and PLTP is similar between the two groups. In addition, the mRNA level of LDLR is also reduced by approximately 40% in response to PGC-1β knockdown, indicating that this coactivator may be a limiting factor, directly or indirectly, for optimal expression of LDLR in the liver. These results illustrate that PGC-1β is indeed necessary for the full activation of the lipogenic program activated by the SREBPs, and perhaps other as yet undefined transcription factors, in the mouse liver.

Circulating lipid levels in the mice transduced with the RNAi against PGC-1β were also examined. Consistent with a key role of PGC-1β in the regulation of lipoprotein synthesis and secretion, plasma triglyceride concentration is significantly reduced (15%) in Ad-RNAi transduced mice when Led either chow or a high-fat diet (FIG. 8C). Hepatic triglyceride levels tend to be higher in the RNAi group, but the difference does not reach statistical significance. Results demonstrate that plasma cholesterol level is increased in mice following high-fat feeding (FIG. 8D). Total plasma cholesterol concentration is slightly but significantly higher in Ad-RNAi transduced mice following high fat feeding. This is due to an increase in both HDL and non-HDL cholesterol (FIG. 8D). This may also be a result of, at least in part, the decreased expression of LDLR observed when PGC-1βB is knocked down in live animals (FIG. 8B).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for treating a lipid-related disease or disorder in a subject in need thereof comprising the step of administering to the subject a peroxisome proliferator-activated receptor gamma coactivator 1β (PGC-1β) modulator, wherein the PGC-1β modulator specifically modulates PGC-1β expression or activity, such that the lipid-related disease or disorder is treated, and wherein the PGC-1β modulator is a nucleic acid.

2. The method of claim 1, wherein the PGC-1β modulator decreases PGC-1β expression or activity.

3. The method of claim 1, wherein the lipid-related disease or disorder is indicated by elevated levels of VLDL cholesterol or LDL cholesterol.

4. The method of claim 1, wherein the lipid-related disease or disorder is indicated by elevated levels of triglycerides.

5. The method of claim 1, wherein the lipid-related disease or disorder is selected from the group consisting of hyperlipidemia, hypertriglyceridemia, hypercholesterolemia, cardiovascular disease, obesity, and type II diabetes.

6. The method of claim 1, wherein the subject is a mammal.

7. The method of claim 6, wherein the subject is a human.

8. The method of claim 6, wherein the subject is selected from the group consisting of a dog, cat, horse, cow, and sheep.

9. The method of claim 1, wherein the modulator is administered in a pharmaceutically acceptable formulation.

10. The method of claim 1, wherein the modulator is capable of modulating PGC-1β nucleic acid expression.

11. The method of claim 10, wherein the modulator is an antisense PGC-1β nucleic acid molecule.

12. The method of claim 10, wherein the modulator is a ribozyme.

13. The method of claim 10, wherein the modulator is an RNA interfering agent.

14. The method of claim 13, wherein the RNA interfering agent is an siRNA molecule targeting PGC-1β.

15. The method of claim 10, wherein the PGC-1β modulator comprises the nucleotide sequence of SEQ ID NO: 1, or a fragment thereof.

16. The method of claim 1, wherein the PGC-1β modulator modulates the expression or activity of an SREBP transcription factor.

17. The method of claim 1, wherein the PGC-1β modulator modulates the expression or activity of a lipogenic gene.

18. The method of claim 17, wherein the lipogenic gene is selected from the group consisting of FAS, SCD-1, HMG-CoA reductase, DGAT, and GPAT.

19. The method of claim 1, wherein the PGC-1β modulator modulates the expression or activity of an LXRα target gene.

20. The method of claim 19, wherein the LXRα target gene is selected from the group consisting of PLTP, ABCA1, and ABCG1.

21. A method of modulating lipid biosynthesis in a hepatocyte cell contacting the cell with a PGC-1β modulator such that lipid biosynthesis is modulated, wherein the PGC-1β modulator is a nucleic acid.

22. The method of claim 21, wherein the lipid biosynthesis is modulated by an SREBP transcription factor.

23. The method of claim 22, wherein the SREBP transcription factor is selected from the group consisting of SREBP1a, SREBP1c and SREBP2.

24. The method of claim 21, wherein the lipid is at least one of a triglyceride and cholesterol.

25. The method of claim 24, wherein the cholesterol is VLDL cholesterol or LDL cholesterol.

26. A method of modulating lipid transport from a hepatocyte cell contacting the cell with a PGC-1β modulator such that lipid transport is modulated, wherein the PGC-1β modulator is a nucleic acid.

27. The method of claim 26, wherein the lipid transport is modulated by LXRα.

28. The method of claim 26, wherein the lipid is cholesterol or triglyceride.

29. The method of claim 28, wherein the cholesterol is VLDL cholesterol or LDL cholesterol.

30. A method of modulating lipid biosynthesis and lipid transport in a hepatocyte cell comprising the step of contacting the cell with a PGC-1β modulator such that lipid biosynthesis and lipid transport are modulated, wherein the PGC-1β modulator is a nucleic acid.

31. A method of modulating at least one of lipid biosynthesis and lipid transport in a subject in need thereof comprising the step of administering to the subject a PGC-1β modulator, such that at least one of lipid biosynthesis and lipid transport is modulated, wherein the PGC-1β modulator is a nucleic acid.

32. The method of claim 31, wherein the PGC-1β modulator modulates the ability of PGC-1β to bind to an SREBP transcription factor.

33. The method of claim 32, wherein the SREBP transcription factor is selected from the group consisting of SREBP1a, SREBP1c and SREBP2.

34. The method of claim 31, wherein the PGC-1β modulator modulates the ability of PGC-1β to bind to LXRα.

35. The method of claim 31, wherein the lipid is at least one of a triglyceride and cholesterol.

36. The method of claim 31, wherein the lipid biosynthesis and/or the lipid transport is in the liver.

37. A method of modulating at least one of plasma triglyceride level and plasma cholesterol level in a subject in need thereof cholesterol level in a subject, comprising the step of administering to the subject a PGC-1β modulator, such that at least one of plasma triglyceride level and plasma cholesterol level is modulated, wherein the PGC-1β modulator is a nucleic acid.

38. The method of claim 37, wherein the cholesterol is VLDL cholesterol or LDL cholesterol.

* * * * *